United States Patent
Blake et al.

(10) Patent No.: US 9,469,861 B2
(45) Date of Patent: Oct. 18, 2016

(54) CELL-FREE PREPARATION OF CARBAPENEMS

(75) Inventors: William Jeremy Blake, Jamaica Plain, MA (US); Daniel Klein-Marcuschamer, San Francisco, CA (US)

(73) Assignee: GreenLight Biosciences, Inc., Medford, MA (US)

( * ) Notice: Subject to any disclaimer, the term of this patent is extended or adjusted under 35 U.S.C. 154(b) by 184 days.

(21) Appl. No.: 13/606,911

(22) Filed: Sep. 7, 2012

(65) Prior Publication Data

US 2013/0065878 A1 Mar. 14, 2013

Related U.S. Application Data

(60) Provisional application No. 61/533,039, filed on Sep. 9, 2011.

(51) Int. Cl.
| | |
|---|---|
| C12P 17/18 | (2006.01) |
| C12N 15/52 | (2006.01) |
| C12N 9/12 | (2006.01) |
| C12N 9/00 | (2006.01) |
| C12N 9/02 | (2006.01) |
| C12N 9/06 | (2006.01) |

(52) U.S. Cl.
CPC ........... *C12P 17/184* (2013.01); *C12N 9/0008* (2013.01); *C12N 9/0026* (2013.01); *C12N 9/1217* (2013.01); *C12N 9/93* (2013.01); *C12N 15/52* (2013.01); *C12Y 102/01041* (2013.01); *C12Y 105/99008* (2013.01); *C12Y 207/02011* (2013.01); *C12Y 603/04016* (2013.01); *C12Y 603/05005* (2013.01); *Y02P 20/52* (2015.11)

(58) Field of Classification Search
CPC .. C12N 15/52; C12N 9/0008; C12N 9/0026; C12N 9/1217; C12N 9/93; C12P 17/184; C12Y 105/99008; C12Y 207/02011
See application file for complete search history.

(56) References Cited

U.S. PATENT DOCUMENTS

| | | |
|---|---|---|
| 3,684,652 A | 8/1972 | Nakayama et al. |
| 3,950,357 A | 4/1976 | Kahan et al. |
| RE28,886 E | 6/1976 | Nakayama et al. |
| 4,006,060 A | 2/1977 | Kahan et al. |
| 4,194,047 A | 3/1980 | Christensen et al. |
| 4,248,966 A | 2/1981 | Demain et al. |
| 4,266,034 A | 5/1981 | Patel |
| 4,270,537 A | 6/1981 | Romaine |
| 4,292,436 A | 9/1981 | Liu et al. |
| 4,329,481 A | 5/1982 | Liu et al. |
| 4,374,772 A | 2/1983 | Hazen et al. |
| 4,438,201 A | 3/1984 | Kubo et al. |
| 4,458,066 A | 7/1984 | Caruthers et al. |
| 4,460,689 A | 7/1984 | Foor et al. |
| 4,596,556 A | 6/1986 | Morrow et al. |
| 4,790,824 A | 12/1988 | Morrow et al. |
| 4,886,499 A | 12/1989 | Cirelli et al. |
| 4,940,460 A | 7/1990 | Casey et al. |
| 4,941,880 A | 7/1990 | Burns |
| 4,946,783 A | 8/1990 | Beckwith et al. |
| 4,950,603 A | 8/1990 | Ingolia et al. |
| 5,001,055 A | 3/1991 | Imahori et al. |
| 5,015,235 A | 5/1991 | Crossman |
| 5,064,413 A | 11/1991 | McKinnon et al. |
| 5,070,020 A | 12/1991 | Ingolia et al. |
| 5,141,496 A | 8/1992 | Dalto et al. |
| 5,190,521 A | 3/1993 | Hubbard et al. |
| 5,312,335 A | 5/1994 | McKinnon et al. |
| 5,319,122 A | 6/1994 | Friedman |
| 5,328,483 A | 7/1994 | Jacoby |
| 5,334,144 A | 8/1994 | Alchas et al. |
| 5,339,163 A | 8/1994 | Homma et al. |
| 5,383,851 A | 1/1995 | McKinnon et al. |

(Continued)

FOREIGN PATENT DOCUMENTS

| | | |
|---|---|---|
| EP | 0 377 295 A1 | 7/1990 |
| EP | 0 444 775 A1 | 9/1991 |
| EP | 0 553 821 A1 | 8/1993 |
| EP | 1 433 856 A1 | 6/2004 |
| EP | 1 502 956 A1 | 2/2005 |
| EP | 1 939 210 A1 | 7/2008 |
| EP | 2 204 453 A1 | 7/2010 |
| GB | 2 018 822 A | 10/1979 |
| JP | S61-260895 A | 11/1986 |
| JP | S61-7788 A | 1/1988 |

(Continued)

OTHER PUBLICATIONS

U.S. Appl. No. 13/606,911, filed Sep. 7, 2012, Blake et al.

(Continued)

*Primary Examiner* — Marsha Tsay
(74) *Attorney, Agent, or Firm* — Wolf, Greenfield & Sacks, P.C.

(57) ABSTRACT

Provided herein are cell-free systems for generating carbapenems, e.g., a compound of the Formula (I):

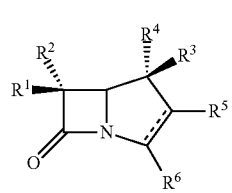

(I)

or salts thereof; wherein ----, $R^1$, $R^2$, $R^3$, $R^4$, $R^5$, and $R^6$ are defined herein. Also provided are pharmaceutical compositions comprising a compound generated by the inventive cell-free system, and use of these compounds and compositions for the treatment of bacterial infections.

21 Claims, 27 Drawing Sheets

(56) References Cited

U.S. PATENT DOCUMENTS

| | | |
|---|---|---|
| 5,417,662 A | 5/1995 | Hjertman et al. |
| 5,436,131 A | 7/1995 | Condra et al. |
| 5,466,220 A | 11/1995 | Brenneman |
| 5,480,381 A | 1/1996 | Weston |
| 5,503,627 A | 4/1996 | McKinnon et al. |
| 5,520,639 A | 5/1996 | Peterson et al. |
| 5,527,288 A | 6/1996 | Gross et al. |
| 5,569,189 A | 10/1996 | Parsons |
| 5,593,856 A | 1/1997 | Choi et al. |
| 5,599,302 A | 2/1997 | Lilley et al. |
| 5,649,912 A | 7/1997 | Peterson |
| 5,665,566 A | 9/1997 | Lavallie |
| 5,672,497 A | 9/1997 | Cox et al. |
| 5,704,911 A | 1/1998 | Parsons |
| 5,871,922 A | 2/1999 | Salmond et al. |
| 5,893,397 A | 4/1999 | Peterson et al. |
| 5,993,412 A | 11/1999 | Deily et al. |
| 6,168,931 B1 | 1/2001 | Swartz et al. |
| 6,387,667 B1 | 5/2002 | Maruyama et al. |
| 6,440,688 B1 | 8/2002 | Bruce et al. |
| 6,472,169 B1 | 10/2002 | Frost et al. |
| 6,531,299 B1 | 3/2003 | Khosla et al. |
| 6,746,859 B1 | 6/2004 | LaVallie |
| 6,921,659 B2 | 7/2005 | Joly |
| 6,994,986 B2 | 2/2006 | Swartz et al. |
| 7,041,479 B2 | 5/2006 | Swartz et al. |
| 7,223,390 B2 | 5/2007 | Brown |
| 7,226,767 B2 | 6/2007 | Maruyama et al. |
| 7,312,049 B2 | 12/2007 | Calhoun et al. |
| 7,338,789 B2 | 3/2008 | Swartz et al. |
| 7,341,852 B2 | 3/2008 | Voloshin et al. |
| 7,351,563 B2 | 4/2008 | Swartz et al. |
| 8,859,247 B2 | 10/2014 | Koltermann et al. |
| 8,916,358 B2 | 12/2014 | Swartz |
| 8,956,833 B2 | 2/2015 | Swartz |
| 2002/0058303 A1 | 5/2002 | Swartz et al. |
| 2002/0127633 A1 | 9/2002 | Dilley et al. |
| 2002/0160459 A1 | 10/2002 | Berry et al. |
| 2003/0022178 A1 | 1/2003 | Schneewind et al. |
| 2003/0040086 A1 | 2/2003 | Dodge et al. |
| 2003/0113778 A1 | 6/2003 | Schulte et al. |
| 2004/0002103 A1 | 1/2004 | Short |
| 2004/0038250 A1 | 2/2004 | Nunez et al. |
| 2004/0091976 A1 | 5/2004 | Deng et al. |
| 2004/0209321 A1 | 10/2004 | Swartz et al. |
| 2005/0054044 A1 | 3/2005 | Swartz et al. |
| 2006/0234358 A1 | 10/2006 | Anderlei et al. |
| 2006/0281148 A1 | 12/2006 | Swartz et al. |
| 2007/0111283 A1 | 5/2007 | Cannon et al. |
| 2007/0154983 A1 | 7/2007 | Calhoun et al. |
| 2007/0161092 A1 | 7/2007 | Townsend et al. |
| 2007/0202198 A1 | 8/2007 | Purcell |
| 2008/0131925 A1 | 6/2008 | Berk et al. |
| 2009/0053779 A1 | 2/2009 | Lee et al. |
| 2009/0124012 A1 | 5/2009 | Nikolsky et al. |
| 2009/0155867 A1 | 6/2009 | Soucaille |
| 2009/0275096 A1 | 11/2009 | Burgard et al. |
| 2009/0275097 A1 | 11/2009 | Sun et al. |
| 2009/0312539 A1 | 12/2009 | Gnanaprakasam et al. |
| 2009/0325245 A1 | 12/2009 | Soucaille et al. |
| 2010/0120105 A1 | 5/2010 | Anthony et al. |
| 2010/0143997 A1 | 6/2010 | Buelter et al. |
| 2010/0291653 A1 | 11/2010 | Ness et al. |
| 2011/0008867 A1 | 1/2011 | Zarur et al. |
| 2011/0099670 A1 | 4/2011 | Koops et al. |
| 2011/0124069 A1 | 5/2011 | Mampel et al. |
| 2011/0262946 A1 | 10/2011 | Roy et al. |
| 2011/0269198 A1 | 11/2011 | Klein-Marcuschamer |
| 2011/0275116 A1 | 11/2011 | Swartz |
| 2012/0052547 A1 | 3/2012 | Swartz |
| 2012/0070870 A1 | 3/2012 | Way et al. |
| 2014/0193869 A1 | 7/2014 | Blake et al. |
| 2015/0037868 A1 | 2/2015 | Blake et al. |
| 2015/0064751 A1 | 3/2015 | Swartz |
| 2015/0191753 A1 | 7/2015 | Swartz |
| 2016/0115558 A1 | 4/2016 | Swartz |

FOREIGN PATENT DOCUMENTS

| | | |
|---|---|---|
| JP | H01-228473 A | 9/1989 |
| JP | H07-298893 A | 11/1995 |
| JP | H08-502176 A | 3/1996 |
| JP | H08-196284 A | 8/1996 |
| JP | 2002-535008 A | 10/2002 |
| WO | WO 97/13537 A1 | 4/1997 |
| WO | WO 97/37705 A1 | 10/1997 |
| WO | WO 98/07690 A1 | 2/1998 |
| WO | WO 99/34850 A1 | 7/1999 |
| WO | WO 00/03581 A1 | 1/2000 |
| WO | 00/44923 A1 | 8/2000 |
| WO | WO 00/55353 A1 | 9/2000 |
| WO | 03/038117 A2 | 5/2003 |
| WO | WO 2005/030949 A1 | 4/2005 |
| WO | WO 2005/098048 A1 | 10/2005 |
| WO | WO 2006/001382 A1 | 1/2006 |
| WO | WO 2006/090385 A2 | 8/2006 |
| WO | WO 2007/053655 A2 | 5/2007 |
| WO | WO 2007/137144 A2 | 11/2007 |
| WO | WO 2008/002661 A2 | 1/2008 |
| WO | WO 2008/002663 A2 | 1/2008 |
| WO | WO 2008/002673 A2 | 1/2008 |
| WO | WO 2008/066583 A2 | 6/2008 |
| WO | WO 2008/088884 A2 | 7/2008 |
| WO | WO 2008/094546 A2 | 8/2008 |
| WO | WO 2010/046713 A2 | 4/2010 |
| WO | WO 2010/074760 A1 | 7/2010 |
| WO | WO 2010/077806 A1 | 7/2010 |
| WO | WO 2011/017560 A1 | 2/2011 |
| WO | WO 2011/072287 A2 | 6/2011 |
| WO | WO 2011/140516 A2 | 11/2011 |
| WO | WO 2012/030980 A1 | 3/2012 |
| WO | WO 2012/135902 A1 | 10/2012 |
| WO | WO 2014/197655 A1 | 12/2014 |

OTHER PUBLICATIONS

U.S. Appl. No. 13/102,967, filed May 6, 2011, Swartz.
U.S. Appl. No. 13/223,042, filed Aug. 31, 2011, Swartz.
U.S. Appl. No. 13/132,721, filed Jul. 12, 2011, Klein-Marcuschamer.
U.S. Appl. No. 12/644,998, filed Dec. 22, 2009, Zarur et al.
PCT/US2012/054195, Apr. 12, 2013, Report International Search Report and Written Opinion.
PCT/US2012/054195, Mar. 20, 2014, International Preliminary Report on Patentability.
PCT/US2011/049997, Mar. 14, 2013, International Preliminary Report on Patentability.
Bodner et al., Definition of the common and divergent steps in carbapenem β-lactam antibiotic biosynthesis. Chembiochem. Sep, 19, 2011;12(14):2159-65. doi: 10.1002/cbic.201100366. Epub Aug. 24, 2011.
Bujara et al., Optimization of a blueprint for in vitro glycolysis by metabolic real-time analysis. Nat Chem Biol. May 2011;7(5):271-7. doi: 10.1038/nchembio.541. Epub Mar. 20, 2011.
Hamed et al., Crotonase catalysis enables flexible production of functionalized prolines and carbapenams. J Am Chem Soc. Jan. 11, 2012;134(1):471-9. doi: 10.1021/ja208318d. Epub Dec. 14, 2011.
Hamed et al., The enzymes of β-lactam biosynthesis. Nat Prod Rep. Jan. 2013;30(1):21-107. doi: 10.1039/c2np20065a.
Swartz, Transforming biochemical engineering with cell-free biology. AIChE J. 2012;58(1):5-13.
Ward et al., Genomic insights into methanotrophy: the complete genome sequence of Methylococcus capsulatus (Bath). PLOS Biology. 2004;2(10):1616-28.
PCT/US2011/035639, Sep. 12, 2011, Invitation to Pay Additional Fees.
PCT/US2011/035639, Nov. 18, 2011, International Search Report and Written Opinion.

(56) References Cited

OTHER PUBLICATIONS

PCT/US2011/035639, Nov. 22, 2012, International Preliminary Report on Patentability.
PCT/US2011/049997, Dec. 13, 2011, International Search Report and Written Opinion.
EP 09836804.6, Jun. 4, 2012, Extended European Search Report.
PCT/US2009/067841, Mar. 22, 2010, International Search Report and Written Opinion.
PCT/US2009/067841, Jun. 30, 2011, International Preliminary Report on Patentability.
PCT/US2009/006704, Mar. 3, 2010, International Search Report and Written Opinion.
PCT/US2009/006704, Jul. 7, 2011, International Preliminary Report on Patentability.
Invitation to Pay Additional Fees for PCT/US2011/035639 mailed Sep. 12, 2011.
International Search Report and Written Opinion for PCT/US2011/035639 mailed Nov. 18, 2011.
International Preliminary Report on Patentability for PCT/US2011/035639 mailed Nov. 22, 2012.
International Search Report and Written Opinion for PCT/US2011/049997 mailed Dec. 13, 2011.
Extended European Search Report for EP 09836804.6 mailed Jun. 4, 2012.
International Search Report and Written Opinion for PCT/US2009/067841 mailed Mar. 22, 2010.
International Preliminary Report on Patentability for PCT/US2009/067841 mailed Jun. 30, 2011.
International Search Report and Written Opinion for PCT/US2009/006704 mailed Mar. 3, 2010.
International Preliminary Report on Patentabilityfor PCT/US2009/006704 mailed Jul. 7, 2011.
Office Action mailed Jul. 2, 2012 for U.S. Appl. No. 12/644,998.
GENBANK Submission; NIH/NCBI, Accession No. AAB59985; Ling et al.; Nov. 24, 1994.
GENBANK Submission; NIH/NCBI, Accession No. AAC73225; Blattner et al.; Sep. 1, 2011.
GENBANK Submission; NIH/NCBI, Accession No. AAC73226; Blattner et al.; Sep. 1, 2011.
GENBANK Submission; NIH/NCBI, Accession No. AAC73296; Blattner et al.; Sep. 1, 2011.
GENBANK Submission; NIH/NCBI, Accession No. AAC73346; Blattner et al.; Sep. 1, 2011.
GENBANK Submission; NIH/NCBI, Accession No. AAC73347; Blattner et al.; Sep. 1, 2011.
GENBANK Submission; NIH/NCBI, Accession No. AAC73842; Blattner et al.; Sep. 1, 2011.
GENBANK Submission; NIH/NCBI, Accession No. AAC73957; Blattner et al.; Sep. 1, 2011.
GENBANK Submission; NIH/NCBI, Accession No. AAC74746; Blattner et al.; Sep. 1, 2011.
GENBANK Submission; NIH/NCBI, Accession No. AAC74849; Blattner et al.; Sep. 1, 2011.
GENBANK Submission; NIH/NCBI, Accession No. AAC74924; Blattner et al.; Sep. 1, 2011.
GENBANK Submission; NIH/NCBI, Accession No. AAC75447; Blattner et al.; Sep. 1, 2011.
GENBANK Submission; NIH/NCBI, Accession No. AAC75821; Blattner et al.; Sep. 1, 2011.
GENBANK Submission; NIH/NCBI, Accession No. AAC75962; Blattner et al.; Sep. 1, 2011.
GENBANK Submission; NIH/NCBI, Accession No. AAC75963; Blattner et al.; Sep. 1, 2011.
GENBANK Submission; NIH/NCBI, Accession No. AAC76849; Blattner et al.; Sep. 1, 2011.
GENBANK Submission; NIH/NCBI, Accession No. AAC76898; Blattner et al.; Sep. 1, 2011.
GENBANK Submission; NIH/NCBI, Accession No. AAC76901; Blattner et al.; Sep. 1, 2011.
GENBANK Submission; NIH/NCBI, Accession No. AAC76995; Blattner et al.; Sep. 1, 2011.
GENBANK Submission; NIH/NCBI, Accession No. AAD38229; McGowan et al.; Jul. 14, 1999.
GENBANK Submission; NIH/NCBI, Accession No. AAD38230; McGowan et al.; Jul. 14, 1999.
GENBANK Submission; NIH/NCBI, Accession No. AAD38231; McGowan et al.; Jul. 14, 1999.
GENBANK Submission; NIH/NCBI, Accession No. ABA79923; Copeland et al.; Nov. 21, 2011.
GENBANK Submission; NIH/NCBI, Accession No. ACJ71669; Erb et al.; Dec. 10, 2008.
GENBANK Submission; NIH/NCBI, Accession No. AEW99093; Ou et al.; Dec. 29, 2011.
GENBANK Submission; NIH/NCBI, Accession No. AEW99097; Ou et al.; Dec. 29, 2011.
GENBANK Submission; NIH/NCBI, Accession No. AEW99098; Ou et al.; Dec. 29, 2011.
GENBANK Submission; NIH/NCBI, Accession No. BAA22406; Mori et al.; Sep. 20, 1997.
GENBANK Submission; NIH/NCBI, Accession No. BAB67276; Kawarabayasi et al.; Aug. 17, 2011.
GENBANK Submission; NIH/NCBI, Accession No. CAD18973; Nunez et al.; Apr. 15, 2005.
GENBANK Submission; NIH/NCBI, Accession No. CAD18975; Nunez et al.; Apr. 15, 2005.
GENBANK Submission; NIH/NCBI, Accession No. CAD18981; Nunez et al.; Apr. 15, 2005.
GENBANK Submission; NIH/NCBI, Accession No. CAD18985; Nunez et al.; Apr. 15, 2005.
GENBANK Submission; NIH/NCBI, Accession No. CAD18990; Nunez et al.; Apr. 15, 2005.
UniProtKB/Swiss-Prot; Accession No. P28269; Yonaha et al.; Jul. 11, 2012.
[No Author Listed] Biolistic® Particle Delivery System Bibliography. Bio-Rad Technical Bulletin #1687. Bio-Rad Laboratories. 12 pages.
[No Author Listed] Biapenem. Drugs Fut. 1994;19(7):631-637.
Adams et al., Hindered dialkylamino nucleoside phosphite reagents in the synthesis of two DNA 51-mers. J Am Chem Soc. 1983;105(3):661-3.
Alber et al., Malonyl-coenzyme A reductase in the modified 3-hydroxypropionate cycle for autotrophic carbon fixation in archaeal *Metallosphaera* and *Sulfolobus* spp. J Bacteriol. Dec. 2006;188(24):8551-9. Epub Oct. 13, 2006.
Allain, Cell-free ethanol production: the future of fuel ethanol? J Chem Technol Biotechnol. 2007;82:117-20.
Alper et al., Tuning genetic control through promoter engineering. Proc Natl Acad Sci U S A. Sep. 6, 2005;102(36):12678-83. Epub Aug. 25, 2005.
Alves-Pereira et al., CDP-alcohol hydrolase, a very efficient activity of the 5'-nucleotidase/udp-sugar hydrolase encoded by the usha gene of *Yersinia intermedia* and *Escherichia coli*. J Bacteriol. Sep. 15, 2008;190(18):6153-61. Published ahead of print Jul. 18, 2008 , doi:10.1128/JB.00658-08.
Anthony et al., Optimization of the mevalonate-based isoprenoid biosynthetic pathway in *Escherichia coli* for production of the anti-malarial drug precursor amorpha-4,11-diene. Metab Eng. Jan. 2009;11(1):13-9. Epub Aug. 12, 2008.
Atsumi et al., Metabolic engineering of *Escherichia coli* for 1-butanol production. Metab Eng. Nov. 2008;10(6):305-11. Epub Sep. 14, 2007.
Atsumi et al., Non-fermentative pathways for synthesis of branched-chain higher alcohols as biofuels. Nature. Jan. 3, 2008;451(7174):86-9.
Bateson et al., Olivanic acid analogues. Part 6. Biomimetic synthesis of (±)-PS-5, (±)-6-Epi-PS-5, and (±)-benzyl MM22381. J Chem Soc Perkin Trans 1. 1990;1793-1801.
Baum et al., beta-Galactosidase containing a human immunodeficiency virus protease cleavage site is cleaved and inactivated by human immunodeficiency virus protease. Proc Natl Acad Sci U S A. Dec. 1990;87(24):10023-7.

(56) References Cited

OTHER PUBLICATIONS

Beaucage et al., Deoxynucleoside phosphoramidites—A new class of key intermediates for deoxypolynucleotide synthesis. Tetra Lett. 1981;22(20):1859-62.

Belousov et al., Sequence-specific targeting and covalent modification of human genomic DNA. Nucleic Acids Res. Sep. 1, 1997;25(17):3440-4.

Benton et al., Screening lambdagt recombinant clones by hybridization to single plaques in situ. Science. Apr. 8, 1977;196(4286):180-2.

Berge et al., Pharmaceutical salts. J Pharmaceut Sci. Jan. 1977;66(1):1-19.

Blommers et al., Effects of the introduction of L-nucleotides into DNA. Solution structure of the heterochiral duplex d(G-C-G-(L)T-G-C-G).d(C-G-C-A-C-G-C) studied by NMR spectroscopy. Biochemistry. Jun. 28, 1994;33(25):7886-96.

Bodner et al., Non-heme iron oxygenases generate natural structural diversity in carbapenem antibiotics. J Am Chem Soc. Jan. 13, 2010;132(1):12-3.

Boiteux et al., Design of glycolysis. Philos Trans R Soc Lond B Biol Sci. Jun. 26, 1981;293(1063):5-22.

Bongaerts et al., Metabolic engineering for microbial production of aromatic amino acids and derived compounds. Metab Eng. Oct. 2001;3(4):289-300.

Boyer et al., Cell-free synthesis and maturation of [FeFe] hydrogenases. Biotechnol Bioeng. Jan. 1, 2008;99(1):59-67.

Bradley, Star role for bacteria in controlling flu pandemic? Nat Rev Drug Discov. Dec. 2005;4(12):945-6.

Brown et al., Chemical synthesis and cloning of a tyrosine tRNA gene. Methods Enzymol. 1979;68:109-51.

Buist et al., Different subcellular locations of secretome components of Gram-positive bacteria. Microbiology. Oct. 2006;152(Pt 10):2867-74.

Calhoun et al., An economical method for cell-free protein synthesis using glucose and nucleoside monophosphates. Biotechnol Prog. Jul.-Aug. 2005;21(4):1146-53.

Calhoun et al., Energizing cell-free protein synthesis with glucose metabolism. Biotechnol Bioeng. Jun. 5, 2005;90(5):606-13.

Calhoun et al., Energy systems for ATP regeneration in cell-free protein synthesis reactions. Methods in Molecular Biology. In vitro transcription and translation protocols. 375(2):3-17.

Calhoun et al., Total amino acid stabilization during cell-free protein synthesis reactions. J Biotechnol. May 17, 2006;123(2):193-203. Epub Jan. 26, 2006.

Campbell et al., The CTP:phosphocholine cytidylyltransferase encoded by the licC gene of *Streptococcus pneumoniae*: cloning, expression, purification, and characterization. Biochim Biophys Acta. Dec. 30, 2001;1534(2-3):85-95.

Chandran et al., Phosphoenolpyruvate availability and the biosynthesis of shikimic acid. Biotechnol Prog. May-Jun. 2003;19(3):808-14.

Chang et al., YPA: an integrated repository of promoter features in *Saccharomyces cerevisiae*. Nucleic Acids Res. Jan. 2011;39(Database issue):D647-52. Epub Nov. 2, 2010.

Chen et al., A modified osmotic shock for periplasmic release of a recombinant creatinase from *Escherichia coli*. Biochem Eng J. 2004;19:211-5.

Chen et al., Crystal structures of penicillin-binding protein 6 from *Escherichia coli*. J Am Chem Soc. Oct. 14, 2009;131(40):14345-54.

Chen et al., High-level accumulation of a recombinant antibody fragment in the periplasm of *Escherichia coli* requires a triple-mutant (degP prc spr) host strain. Biotechnol Bioeng. Mar. 5, 2004;85(5):463-74.

Chiu et al., Site-directed, Ligase-Independent Mutagenesis (SLIM): a single-tube methodology approaching 100% efficiency in 4 h. Nucleic Acids Res. Dec. 7, 2004;32(21):e174.

Chong et al., Single-column purification of free recombinant proteins using a self-cleavable affinity tag derived from a protein splicing element. Gene. Jun. 19, 1997;192(2):271-81.

Choubey et al., Molecular characterization and localization of Plasmodium falciparum choline kinase. Biochim Biophys Acta. Jul. 2006;1760(7):1027-38.

Collins-Racie et al., Production of recombinant bovine enterokinase catalytic subunit in *Escherichia coli* using the novel secretory fusion partner DsbA. Biotechnology (N Y). Sep. 1995;13(9):982-7.

Coulthurst et al., Regulation and biosynthesis of carbapenem antibiotics in bacteria. Nat Rev Microbiol. Apr. 2005;3(4):295-306. Erratum included.

Dahiyat et al., De novo protein design: fully automated sequence selection. Science. Oct. 3, 1997;278(5335):82-7.

Dahl et al., Isolation and characterization of Chinese hamster ovary cells defective in the intracellular metabolism of low density lipoprotein-derived cholesterol. J Biol Chem. Mar. 5, 1992;267(7):4889-96.

Dani et al., Isolation and characterization of a thylakoid membrane module showing partial light and dark reactions. Biochim Biophys Acta. May 15, 2005;1669(1):43-52.

Daniell et al., Transformation of the cyanobacterium Anacystis nidulans 6301 with the *Escherichia coli* plasmid pBR322. Proc Natl Acad Sci U S A. Apr. 1986;83(8):2546-50.

Datsenko et al., One-step inactivation of chromosomal genes in *Escherichia coli* K-12 using PCR products. Proc Natl Acad Sci U S A. Jun. 6, 2000;97(12):6640-5.

De Boer et al., Protein targeting towards the thylakoid lumen of chloroplasts: proper localization of fusion proteins is only observed in vivo. EMBO J. Oct. 1991;10(10):2765-72.

De Mey et al., Construction and model-based analysis of a promoter library for *E. coli*: an indispensable tool for metabolic engineering. BMC Biotechnol. Jun. 18, 2007;7:34.

Dietrich et al., A novel semi-biosynthetic route for artemisinin production using engineered substrate-promiscuous P450(BM3). ACS Chem Biol. Apr. 17, 2009;4(4):261-7.

Dingwall et al., The nucleoplasmin nuclear location sequence is larger and more complex than that of SV-40 large T antigen. J Cell Biol. Sep. 1988;107(3):841-9.

Draper et al., Ti plasmid homologous sequences present in tissues from agrobacterium plasmid-transformed petunia protoplasts. Plant Cell Physiol. 1982;23(3):451-8.

Elander, Industrial production of beta-lactam antibiotics. Appl Microbiol Biotechnol. Jun. 2003;61(5-6):385-92. Epub Apr. 3, 2003.

Erb et al., Carboxylation mechanism and stereochemistry of crotonyl-CoA carboxylase/reductase, a carboxylating enoyl-thioester reductase. Proc Natl Acad Sci U S A. Jun. 2, 2009;106(22):8871-6. Epub May 20, 2009.

Erb et al., Synthesis of C5-dicarboxylic acids from C2-units involving crotonyl-CoA carboxylase/reductase: The ethylmalonyl-CoA pathway. Proc Nat Acad Sci. Jun. 4, 2007;104(25):10631-6.

Evans et al., The asymmetric synthesis of β-lactam antibiotics—IV. A formal synthesis of thienamycin. Tetra Lett. 1986;27(41):4961-4.

Fischer et al., Metabolic flux profiling of *Escherichia coli* mutants in central carbon metabolism using GC-MS. Eur J Biochem. Mar. 2003;270(5):880-91.

Flores et al., Analysis of carbon metabolism in *Escherichia coli* strains with an inactive phosphotransferase system by (13)C labeling and NMR spectroscopy. Metab Eng. Apr. 2002;4(2):124-37.

Flores et al., Growth-rate recovery of *Escherichia coli* cultures carrying a multicopy plasmid, by engineering of the pentose-phosphate pathway. Biotechnol Bioeng. Aug. 20, 2004;87(4):485-94.

Flores et al., Pathway engineering for the production of aromatic compounds in *Escherichia coli*. Nat Biotechnol. May 1996;14(5):620-3.

Fradejas et al., The control of shikimic acid synthesis by tyrosine and phenylalamine. Biochem Biophys Res Commun. Jul. 26, 1961;5:320-3.

Freeman et al., Four enzymes define the incorporation of coenzyme A in thienamycin biosynthesis. Proc Natl Acad Sci U S A. Aug. 12, 2008;105(32):11128-33. Epub Aug. 4, 2008. Supplemental material included.

Freeman et al., A comparison of methods for plasmid delivery into plant protoplasts. Plant Cell Physiol. 1984;25(8):1353-65.

(56) References Cited

OTHER PUBLICATIONS

Frenkel et al., 7,12-dimethylbenz[a]anthracene induces oxidative DNA modification in vivo. Free Radic Biol Med. Sep. 1995;19(3):373-80.
Friesen et al., Purification and Kinetic Characterization of CTP-:Phosphocholine Cytidylyltransferase from *Saccharomyces cerevisiae*. Protein Expression and Purification. Feb. 2001;21(1):141-8.
Fromm et al., Stable transformation of maize after gene transfer by electroporation. Nature. Feb. 27-Mar. 5, 1986;319(6056):791-3.
Fujio et al., Construction of a plasmid carrying both CTP synthetase and a fused gene formed from cholinephosphate cytidylyltransferase and choline kinase genes and its application to industrial CDP-choline production: enzymatic production of CDP-choline from orotic acid (Part II). Biosci Biotechnol Biochem. Jun. 1997;61(6):960-4.
Gaspar et al., High yields of 2,3-butanediol and mannitol in Lactococcus lactis through engineering of $NAD^+$ cofactor recycling. Appl Environ Microbiol. Oct. 2011;77(19):6826-35. Epub Aug. 12, 2011. Supplemental material included.
Ger et al., A single Ser-180 mutation desensitizes feedback inhibition of the phenylalanine-sensitive3-deoxy-D-arabino-heptulosonate 7-phosphate (DAHP) synthetase in *Escherichia coli*. J Biochem. Nov. 1994;116(5):986-90.
Gibellini et al., Biochemical characterization of the initial steps of the Kennedy pathway in Trypanosoma brucei: the ethanolamine and choline kinases. Biochem J. 2008;415:135-44. Supplemental material included.
Goerke et al., Development of cell-free protein synthesis platforms for disulfide bonded proteins. Biotechnol Bioeng. Feb. 1, 2008;99(2):351-67. Epub Jul. 11, 2007.
Gordon-Kamm et al., Transformation of Maize Cells and Regeneration of Fertile Transgenic Plants. Plant Cell. Jul. 1990;2(7):603-618.
Gosset et al., A direct comparison of approaches for increasing carbon flow to aromatic biosynthesis in *Escherichia coli*. J Ind Microbiol. Jul. 1996;17(1):47-52.
Grabowski, Enantiopure drug synthesis: from methyldopa to imipenem to efavirenz. Chirality. 2005;17 Suppl:S249-59.
Grieco et al., β-Lactam antibiotics: a formal stereocontrolled total synthesis of (.+-.)-thienamycin. J Am Chem Soc. 1984;106(21):6414-7.
Grunstein et al., Colony hybridization: a method for the isolation of cloned DNAs that contain a specific gene. Proc Natl Acad Sci U S A. Oct. 1975;72(10):3961-5.
Hamed et al., Carboxymethylproline synthase catalysed syntheses of functionalized N-heterocycles. Chem Commun (Camb). Mar. 7, 2010;46(9):1413-5. Epub Jan. 12, 2010.
Hamed et al., Evidence that thienamycin biosynthesis proceeds via C-5 epimerization: I catalyzes the formation of (2S,5S)-trans-carboxymethylproline. Chembiochem. Jan. 26, 2009;10(2):246-50.
Hawley et al., Compilation and analysis of *Escherichia coli* promoter DNA sequences. Nucleic Acids Res. Apr. 25, 1983;11(8):2237-55.
Herrmann, The shikimate pathway as an entry to aromatic secondary metabolism. Plant Physiol. Jan. 1995;107(1):7-12.
Hikita et al., Effects of total hydrophobicity and length of the hydrophobic domain of a signal peptide on in vitro translocation efficiency. J Biol Chem. 1992;267:4882-8.
Hikita et al., The requirement of a positive charge at the amino terminus can be compensated for by a longer central hydrophobic stretch in the functioning of signal peptides. J Biol Chem. 1992;267:12375-9.
Hodgson et al., π-Allyltricarbonyliron lactone complexes in synthesis: application to the synthesis of the β-lactam antibiotic (+)-thienamycin. J Chem Soc Chem Comm. 1984;8:494-6.
Inouye, The discovery of mRNA interferases: implication in bacterial physiology and application to biotechnology. J Cell Physiol. Dec. 2006;209(3):670-6.

Ishii et al., DBTBS: a database of Bacillus subtilis promoters and transcription factors. Nucleic Acids Res. Jan. 1, 2001;29(1):278-80.
Jacobi et al., Formal Total Syntheses of the β-Lactam Antibiotics Thienamycin and PS-5. J Org Chem. 1996;61(7):2413-27.
Jang et al., Sugar sensing in higher plants. Plant Cell. Nov. 1994;6(11):1665-79.
Jermutus et al., Recent advances in producing and selecting functional proteins by using cell-free translation. Curr Opin Biotechnol. Oct. 1998;9(5):534-48.
Jewett et al., An integrated cell-free metabolic platform for protein production and synthetic biology. Mol Syst Biol. 2008;4:220. Epub Oct. 14, 2008.
Jewett et al., Mimicking the *Escherichia coli* cytoplasmic environment activates long-lived and efficient cell-free protein synthesis. Biotechnol Bioeng. Apr. 5, 2004;86(1):19-26.
Kahan et al., Thienamycin, a new beta-lactam antibiotic. I. Discovery, taxonomy, isolation and physical properties. J Antibiot (Tokyo). Jan. 1979;32(1):1-12.
Kahan et al., Thienamycin: development of imipenen-cilastatin. J Antimicrob Chemother. Dec. 1983;12 Suppl D:1-35.
Kalderon et al., A short amino acid sequence able to specify nuclear location. Cell. Dec. 1984;39(3 Pt 2):499-509.
Kametani et al., Studies on the syntheses of heterocyclic compounds. 800. A formal total synthesis of (.+-.)-thienamycin and a (.+-.)-decysteaminylthienamycin derivative. J Am Chem Soc. 1980;102(6):2060-5.
Kapust et al., Tobacco etch virus protease: mechanism of autolysis and rational design of stable mutants with wild-type catalytic proficiency. Protein Eng. Dec. 2001;14(12):993-1000.
Kern et al., Engineering primary metabolic pathways of industrial micro-organisms. J Biotechnol. Mar. 30, 2007;129(1):6-29. Epub Dec. 2, 2006.
Kikuchi et al., Mutational analysis of the feedback sites of phenylalanine-sensitive 3-deoxy-D-arabino-heptulosonate-7-phosphate synthase of *Escherichia coli*. Appl Environ Microbiol. Feb. 1997;63(2):761-2.
Kim et al., Expression, purification, and characterization of choline kinase, product of the cki gene from *Saccharomyces cerevisiae*. J Bio Chem. 1998;273(12):6844-6852.
Kim et al., Prolonged cell-free protein synthesis using dual energy sources: Combined use of creatine phosphate and glucose for the efficient supply of ATP and retarded accumulation of phosphate. Biotechnol Bioeng. Aug. 15, 2007;97(6):1510-5.
Kimmel, Identification and characterization of specific clones: strategy for confirming the validity of presumptive clones. Methods Enzymol. 1987;152:507-11.
Kindle, High-frequency nuclear transformation of Chlamydomonas reinhardtii. Proc Natl Acad Sci U S A. Feb. 1990;87(3):1228-32.
Knapp et al., Cell-free production of active *E. coli* thioredoxin reductase and glutathione reductase. FEBS Lett. Feb. 13, 2004;559(1-3):66-70.
Knop et al., Hydroaromatic equilibration during biosynthesis of shikimic acid. J Am Chem Soc. Oct. 24, 2001;123(42):10173-82.
Ko et al., Targeting of proteins to the thylakoid lumen by the bipartite transit peptide of the 33 kd oxygen-evolving protein. EMBO J. Nov. 1989;8(11):3187-94.
Krämer et al., Metabolic engineering for microbial production of shikimic acid. Metab Eng. Oct. 2003;5(4):277-83.
Kumagai et al., Current status of oral carbapenem development. Curr Med Chem—Anti-Infective Agents. Jan. 2002;1(1):1-14.
Kunkel, Rapid and efficient site-specific mutagenesis without phenotypic selection. Proc Natl Acad Sci U S A. Jan. 1985;82(2):488-92.
Lee et al., Fermentative production of thymidine by a metabolically engineered *Escherichia coli* strain. Appl Environ Microbiol. Apr. 2009;75(8):2423-32. Epub Feb. 27, 2009.
Lee et al., Systems metabolic engineering of *Escherichia coli* for L-threonine production. Mol Syst Biol. 2007;3:149. Epub Dec. 4, 2007.
Lee, High cell-density culture of *Escherichia coli*. Trends Biotechnol. Mar. 1996;14(3):98-105.

(56) References Cited

OTHER PUBLICATIONS

Liu et al., Streamlining *Escherichia coli* S30 extract preparation for economical cell-free protein synthesis. Biotechnol Prog. Mar.-Apr. 2005;21(2):460-5.
Ludwig et al., Mutations affecting export and activity of cytolysin A from *Escherichia coli*. J Bacteriol. Aug. 2010;192(15):4001-11. Epub May 28, 2010.
Luli et al., Comparison of growth, acetate production, and acetate inhibition of *Escherichia coli* strains in batch and fed-batch fermentations. Appl Environ Microbiol. Apr. 1990;56(4):1004-11.
Mackle et al., Role of signal peptides in targeting of proteins in cyanobacteria. J Bacteriol. Apr. 1994;176(7):1857-64.
Mandel et al., Modular synthesis of pantetheine and phosphopantetheine. Org Lett. Dec. 23, 2004;6(26):4801-3.
Martin et al., Engineering a mevalonate pathway in *Escherichia coli* for production of terpenoids. Nat Biotechnol. Jul. 2003;21(7):796-802. Epub Jun. 1, 2003.
Mergulhão et al., Analysis of factors affecting the periplasmic production of recombinant proteins in *Escherichia coli*. J Microbiol Biotechnol. Aug. 2007;17(8):1236-41.
Mergulhão et al., Recombinant protein secretion in *Escherichia coli*. Biotechnol Adv. May 2005;23(3):177-202. Epub Jan. 8, 2005.
Meyerhof, New investigations in the kinetics of cell free alcoholic fermentation. Antonie Van Leeuwenhoek. Jan.-Apr. 1947;12(1-4):140-4.
Meynial-Salles et al., New tool for metabolic pathway engineering in *Escherichia coli*: one-step method to modulate expression of chromosomal genes. Appl Environ Microbiol. Apr. 2005;71(4):2140-4.
Michel-Reydellet et al., Amino acid stabilization for cell-free protein synthesis by modification of the *Escherichia coli* genome. Metab Eng. Jul. 2004;6(3):197-203.
Muchmore et al., Crystal structure of glutamine phosphoribosylpyrophosphate amidotransferase from *Escherichia coli*.Protein Sci. Jan. 1998;7(1):39-51.
Muktiono et al., Isolation and purification assay of ex vivo photosystem II D1 protein toward integrated biointeraction analysis. Anal Bioanal Chem. Feb. 2008;390(4):1195-202. Epub Jan. 3, 2008.
Murphy, Use of bacteriophage lambda recombination functions to promote gene replacement in *Escherichia coli*. J Bacteriol. Apr. 1998;180(8):2063-71.
Myers et al., Determination of imipenem and cilastatin in serum by high-pressure liquid chromatography. Antimicrob Agents Chemother. Jul. 1984;26(1):78-81.
Narang et al., Improved phosphotriester method for the synthesis of gene fragments. Methods Enzymol. 1979;68:90-8.
Neidhardt et al., Culture medium for enterobacteria. J Bacteriol. Sep. 1974;119(3):736-47.
Mu et al., Benzene-free synthesis of adipic acid. Biotechnol Prog. Mar.-Apr. 2002;18(2):201-11.
Nunez et al., The Biosynthetic Gene Cluster for the β-Lactam Carbapenem Thienamycin in Streptomyces cattleya. Chem Biol. Apr. 2003;10(4):301-11.
Ono et al., Photosynthetic electron transport and phosphorylation reactions in thylakoid membranes from the blue-green alga Anacystis nidulans. Biochim Biophys Acta. Jun. 8, 1978;502(3):477-85.
Park et al., Metal-catalyzed oxidation of phenylalanine-sensitive 3-deoxy-D-arabino heptulosonate-7-phosphate synthase from *Escherichia coli*: inactivation and destabilization by oxidation of active-site cysteines. J Bacteriol. Mar. 1999;181(5):1636-42.
Patnaik et al., Engineering of *Escherichia coli* central metabolism for aromatic metabolite production with near theoretical yield. Appl Environ Microbiol. Nov. 1994;60(11):3903-8.
Pitera et al., Balancing a heterologous mevalonate pathway for improved isoprenoid production in *Escherichia coli*. Metab Eng. Mar. 2007;9(2):193-207. Epub Nov. 23, 2006.
Qi et al., A one-step PCR-based method for rapid and efficient site-directed fragment deletion, insertion, and substitution mutagenesis. J Virolog Meth. Apr. 2008;149(1):85-90.
Ray et al., Mutational analysis of the catalytic and feedback sites of the tryptophan-sensitive 3-deoxy-D-arabino-heptulosonate-7-phosphate synthase of *Escherichia coli*. J Bacteriol. Dec. 1988;170(12):5500-6.
Reider et al., Total synthesis of thienamycin: a new approach from aspartic acid. Tetra Lett. 1982;23(22):2293-6.
Reyes et al., Genomic library screens for genes involved in n-butanol tolerance in *Escherichia coli*. PloS One. Mar. 8, 2011;6(3):e17678.
Rodríguez et al., Identification of transcriptional activators for thienamycin and cephamycin C biosynthetic genes within the thienamycin gene cluster from Streptomyces cattleya. Mol Microbiol. Aug. 2008 ;69(3):633-45.
Rodríguez et al., Transcriptional organization of ThnI-regulated thienamycin biosynthetic genes in Streptomyces cattleya. J Antibiot (Tokyo). Mar. 2010;63(3):135-8. Epub Jan. 22, 2010.
Sagui et al., Enzymatic synthesis of ω-carboxy-β-hydroxy-(1)-α-amino acids. Tetrahedron. May 26, 2008;64(22):5079-84.
Salis et al., Automated design of synthetic ribosome binding sites to control protein expression. Nat Biotechnol. Oct. 2009;27(10):946-50. Epub Oct. 4, 2009. Supplemental material included.
Salzmann et al., A stereocontrolled synthesis of (+)-thienamycin. J Am Chem Soc. 1980;102(19);6161-3.
Salzmann et al., A stereocontrolled, enantiomerically specific total synthesis of thienamycin. Philos Trans R Soc Lond B Biol Sci. May 16, 1980;289(1036):191-5.
Sarath et al., Use of GFP as a reporter for the analysis of sequence-specific proteases. Curr Protoc Protein Sci. Feb. 2001;Chapter 21 Unit 9 Suppl. 26: 21.9.1-.10.
Sato et al., Poly[(R)-3-hydroxybutyrate] formation in *Escherichia coli* from glucose through an enoyl-CoA hydratase-mediated pathway. J Biosci Bioeng, Jan. 2007;103(1):38-44.
Sauer et al., The soluble and membrane-bound transhydrogenases UdhA and PntAB have divergent functions in NADPH metabolism of *Escherichia coli*. J Biol Chem. Feb. 20, 2004;279(8):6613-9. Epub Dec. 3, 2003.
Schlehuber et al., Prediction and identification of a permissive epitope insertion site in the vesicular stomatitis virus glycoprotein. J Virol. May 2004;78(10):5079-87.
Schnell, Protein targeting to the thylakoid membrane. Annu Rev Plant Physiol Plant Mol Biol. Jun. 1998;49:97-126.
Scopes, Glycolysis in cell-free systems. New beer in an old bottle: Eduard Buchner and the growth of biochemical knowledge. Ed A. Cornish-Bowden. 1997;151-8.
Sheen, Metabolic repression of transcription in higher plants. Plant Cell. Oct. 1990;2(10):1027-38.
Shi et al., Molecular properties, functions, and potential applications of NAD kinases. Acta Biochim Biophys Sin (Shanghai). May 2009;41(5):352-61.
Shine et al., Determinant of cistron specificity in bacterial ribosomes. Nature. Mar. 6, 1975;254(5495):34-8.
Simmons et al., Translational level is a critical factor for the secretion of heterologous proteins in *Escherichia coli*. Nat Biotechnol. May 1996;14(5):629-34.
Sleeman et al., Carboxymethylproline synthase (CarB), an unusual carbon-carbon bond-forming enzyme of the crotonase superfamily involved in carbapenem biosynthesis. J Biol Chem. Feb. 20, 2004;279(8):6730-6. Epub Nov. 18, 2003.
Soares et al., Periplasmic expression of human growth hormone via plasmid vectors containing the lambdaPL promoter: use of HPLC for product quantification. Protein Eng. Dec. 2003;16(12):1131-8.
Sorci et al., Nicotinamide mononucleotide synthetase is the key enzyme for an alternative route of NAD biosynthesis in Francisella tularensis.Proc Natl Acad Sci U S A. Mar. 3, 2009;106(9):3083-8. Epub Feb. 9, 2009. Supplemental material included.
Stadtman et al., Metal-catalyzed oxidation of proteins. Physiological consequences. J Biol Chem. Feb. 5, 1991;266(4):2005-8.
Stapon et al., Synthesis of (3S,5R)-carbapenam-3-carboxylic acid and its role in carbapenem biosynthesis and the stereoinversion problem. J Am Chem Soc. Dec. 24, 2003;125(51):15746-7.

(56) References Cited

OTHER PUBLICATIONS

Stephanopoulos et al., Exploiting biological complexity for strain improvement through systems biology. Nat Biotechnol. Oct. 2004;22(10):1261-7.
Suzuki et al., Single protein production (SPP) system in *Escherichia coli*. Nat Protoc. 2007;2(7):1802-10.
Suzuki et al., Single protein production in living cells facilitated by an mRNA interferase. Mol Cell. Apr. 15, 2005;18(2):253-61.
Swartz et al., Advances in *Escherichia coli* production of therapeutic proteins. Curr Opin Biotechnol. Apr. 2001;12(2):195-201.
Swartz, Developing cell-free biology for industrial applications. J Ind Microbiol Biotechnol. Jul. 2006;33(7):476-85. Epub May 9, 2006. Review.
Sybesma et al., Increased production of folate by metabolic engineering of Lactococcus lactis. Appl Environ Microbiol. Jun. 2003;69(6):3069-76.
Tjalsma et al., Proteomics of protein secretion by Bacillus subtilis: separating the "secrets" of the secretome. Microbiol Mol Biol Rev. Jun. 2004;68(2):207-33.
Tracewell et al., Directed enzyme evolution: climbing fitness peaks one amino acid at a time. Curr Opin Chem Biol. Feb. 2009;13(1):3-9. Epub Feb. 25, 2009.
Tyo et al., Analysis of polyhydroxybutyrate flux limitations by systematic genetic and metabolic perturbations. Metab Eng. May 2010;12(3):187-95. Epub Oct. 30, 2009.
Van Bloois et al., Export of functional Streptomyces coelicolor alditol oxidase to the periplasm or cell surface of *Escherichia coli* and its application in whole-cell biocatalysis. Appl Microbiol Biotechnol. Jun. 2009;83(4):679-87. Epub Feb. 18, 2009.
Van Hees et al., Determination of low molecular weight organic acids in soil solution by HPLC. Talanta. Jan. 5, 1999;48(1):173-9.
Voloshin et al., Efficient and scalable method for scaling up cell free protein synthesis in batch mode. Biotechnol Bioeng. Aug. 20, 2005;91(4):516-21.
Wahl et al., Molecular hybridization of immobilized nucleic acids: theoretical concepts and practical considerations. Methods Enzymol. 1987;152:399-407.
Wang et al., Programming cells by multiplex genome engineering and accelerated evolution. Nature. Aug. 13, 2009;460(7257):894-8. Epub Jul. 26, 2009.
Weaver et al., Cloning of an aroF allele encoding a tyrosine-insensitive 3-deoxy-D-arabino-heptulosonate 7-phosphate synthase. J Bacteriol. Nov. 1990;172(11):6581-4.
Welch et al., Studies on cell-free metabolism: Ethanol production by a yeast glycolytic system reconstituted from purified enzymes. J Biotechnol. 1985;2:257-73.
Wiechert et al., A universal framework for 13C metabolic flux analysis. Metab Eng. Jul. 2001;3(3):265-83.
Wiechert, $^{13}$C metabolic flux analysis. Metab Eng. Jul. 2001;3(3):195-206.
Wilen et al., Tetrahedron report No. 38: Strategies in optical resolutions. Tetrahedron. 1977;33:2725-2736.
Williamson et al., Biosynthesis of the beta-lactam antibiotic, thienamycin, by Streptomyces cattleya. J Biol Chem. Apr. 25, 1985;260(8):4637-47.
Wilson et al., The shikimic acid pathway and polyketide biosynthesis. J Indust Microbiol Biotechnol. 1998;20:299-303.
Withers et al., Identification of isopentenol biosynthetic genes from Bacillus subtilis by a screening method based on isoprenoid precursor toxicity. Appl Environ Microbiol. Oct. 2007;73(19):6277-83. Epub Aug. 10, 2007.
Woodrow et al., A sequential expression system for high-throughput functional genomic analysis. Proteomics. Nov. 2007;7(21):3870-9.
Woodrow et al., Rapid expression of functional genomic libraries. J Proteome Res. Dec. 2006;5(12):3288-300.
Wylie et al., A single point mutation in ctp synthetase of chlamydia trachomatis confers resistance to cyclopentenyl cytosine. J Biol Chem. 1996;271:15393-400.

Yamaguchi et al., MqsR, a crucial regulator for quorum sensing and biofilm formation, is a GCU-specific mRNA interferase in *Escherichia coli*. J Biol Chem. Oct. 16, 2009;284(42):28746-53. Epub Aug. 18, 2009.
Yamaguchi et al., mRNA interferases, sequence-specific endoribonucleases from the toxin-antitoxin systems. Prog Mol Biol Transl Sci. 2009;85:467-500.
Yang et al., Export of methyl parathion hydrolase to the periplasm by the twin-arginine translocation pathway in *Escherichia coli*. J Agric Food Chem. Oct. 14, 2009;57(19):8901-5.
Yang et al., Rapid expression of vaccine proteins for B-cell lymphoma in a cell-free system. Biotechnol Bioeng. Mar. 5, 2005;89(5):503-11.
Yeo et al., Plasmodium falciparum CTP:phosphocholine cytidylyltransferase expressed in *Escherichia coli*: purification, characterization and lipid regulation. Biochem J. 1997;324:903-10.
Zamboni et al., $^{13}$C-based metabolic flux analysis. Nat Protoc. 2009;4(6):878-92. Epub May 21, 2009.
Zawada et al., Effects of growth rate on cell extract performance in cell-free protein synthesis. Biotechnol Bioeng. Jul. 5, 2006;94(4):618-24.
Zawada et al., Maintaining rapid growth in moderate-density *Escherichia coli* fermentations. Biotechnol Bioeng. Feb. 20, 2005;89(4):407-15.
Zhang et al., Characterization of ChpBK, an mRNA interferase from *Escherichia coli*. J Biol Chem. Jul. 15, 2005;280(28):26080-8. Epub May 18, 2005.
Zhang et al., Characterization of YafO, an *Escherichia coli* toxin. J Biol Chem. Sep. 18, 2009;284(38):25522-31. Epub Jul. 17, 2009.
Zhang et al., Efficient regeneration of transgenic plants from rice protoplasts and correctly regulated expression of the foreign gene in the plants. Theor Appl Genet. 1988;76(6):835-40.
Zhang et al., Insights into the mRNA cleavage mechanism by MazF, an mRNA interferase. J Biol Chem. Feb. 4, 2005;280(5):3143-50. Epub Nov. 10, 2004.
International Search Report and Written Opinion for PCT/US2012/054195, mailed Apr. 12, 2013.
International Preliminary Report on Patentability for PCT/US2012/054195, mailed Mar. 20, 2014.
International Preliminary Report on Patentability for PCT/US2011/049997, mailed Mar. 14, 2013.
International Search Report and Written Opinion for PCT/US2013/077238, mailed May 19, 2014.
International Search Report and Written Opinion for PCT/US2014/041009, mailed Sep. 10, 2014.
Bujara et al., Exploiting cell-free systems: Implementation and debugging of a system of biotransformations. Biotechnol Bioeng. Jun. 15, 2010;106(3):376-89. doi: 10.1002/bit.22666.
Krutsakorn et al., In vitro production of n-butanol from glucose. Metab Eng. Nov. 2013;20:84-91. doi: 10.1016/j.ymben.2013.09.006. Epub Sep. 19, 2013.
Ninh et al., Assembly and multiple gene expression of thermophilic enzymes in *Escherichia coli* for in vitro metabolic engineering. Biotechnol Bioeng. Jul. 26, 2014. doi: 10.1002/bit.25338. [Epub ahead of print].
Pace et al., Photosynthetic regeneration of ATP using bacterial chromatophores. Biotechnol Bioeng. Oct. 1976;18(10):1413-23.
Paul et al., Photophosphorylation in bacterial chromatophores entrapped in alginate gel: Improvement of the physical and biochemical properties of gel beads with barium as gel-inducing agent. Enzyme Microb Technol. 1980;2(4):281-87.
Srinivasan et al., The Enzymatic Synthesis of Shikimic Acid From D-Erythrose-4-Phosphate and Phosphoenolpyruvate1,2,3. J. Am. Chem. Soc. 1955;77(18):4943-4944.
Ye et al., Synthetic metabolic engineering-a novel, simple technology for designing a chimeric metabolic pathway. Microb Cell Fact. Sep. 6, 2012;11:120. doi: 10.1186/1475-2859-11-120.
International Preliminary Report on Patentability for PCT/US2013/077238 mailed Jul. 2, 2015.
Invitation to Pay Additional Fees for PCT/US2014/049805, mailed Nov. 14, 2014.
International Search Report for PCT/US2014/049805, mailed Feb. 16, 2015.

(56) References Cited

OTHER PUBLICATIONS

[No Author Listed] Crude Lysate. Wikipedia entry for Crude Lysate, http://en.wikipedia.org/wild/Crude_lysate downloaded on Mar. 3, 2015. Page Last Modified on Nov. 3, 2013. 1 page.
Danese et al., Targeting and assembly of periplasmic and outer-membrane proteins in *Escherichia coli*. Annu Rev Genet. 1998;32:59-94.
Ding et al., Functional analysis of the essential bifunctional tobacco enzyme 3-dehydroquinate dehydratase/shikimate dehydrogenase in transgenic tobacco plants. J Exp Bot. 2007;58(8):2053-67. Epub Apr. 26, 2007.
Egan et al., Transketolase kinetics. The slow reconstitution of the holoenzyme is due to rate-limiting dimerization of the subunits. J Biol Chem. May 25, 1981;256(10):4877-83.
Eser et al.,Target-directed proteolysis in vivo. Methods Enzymol. 2007;421:68-83.
Fujio et al., Production of ATP from Adenine by Brevibacterium ammoniagenes, J Ferment Technol. 1983;61(3):261-267.
Goerke et al., Cell-free metabolic engineering promotes high-level production of bioactive Gaussia princeps luciferase.Metab Eng. May-Jul. 2008;10(3-4):187-200. doi: 10.1016/j.ymben.2008.04.001. Epub May 2, 2008.
Hryniewicz et al., Sulfate and thiosulfate transport in *Escherichia coli* K-12: identification of a gene encoding a novel protein involved in thiosulfate binding. J Bacteriol. Jun. 1990;172(6):3358-66.
Jenny et al., A critical review of the methods for cleavage of fusion proteins with thrombin and factor Xa. Protein Expr Punif. Sep. 2003;31(1):1-11.
Kang et al., Enhanced biodegradation of toxic organophosphate compounds using recombinant *Escherichia coli* with sec pathway-driven periplasmic secretion of organophosphorus hydrolase. Biotechnol Prog. Mar.-Apr. 2006;22(2):406-10.
Kim et al., Metabolic flux analysis for calcium dependent antibiotic (CDA) production in Streptomyces coelicolor. Metab Eng. Oct. 2004;6(4):313-25.
Krell et al., Crystallization and preliminary X-ray crystallographic analysis of shikimate kinase from Erwinia chrysanthemi. Acta Crystallogr D Biol Crystallogr. Sep. 1, 1997;53(Pt 5):612-4.
Mayes, Metabolism of Glycogen. In: Harper's Biochemistry—a LANGE medical book. 1990. Twenty-second edition. Murray et al., Eds. Chapter 20: 171-178.
Romanowski et al., Crystal structure of the *Escherichia coli* shikimate kinase I (AroK) that confers sensitivity to mecillinam. Proteins. Jun. 1, 2002;47(4):558-62.
Stapon et al., Carbapenem biosynthesis: confirmation of stereochemical assignments and the role of CarC in the ring stereoinversion process from L-proline. J Am Chem Soc. Jul. 16, 2003;125(28):8486-93.
U.S. Appl. No. 14/620,054, filed Feb. 11, 2015, Swartz.
U.S. Appl. No. 14/542,074, filed Nov. 14, 2014, Swartz.
PCT/US2013/077238, Jul. 2, 2015, International Preliminary Report on Patentability.
PCT/US2014/049805, Nov. 14, 2014, Invitation to Pay Additional Fees.
PCT/US2014/049805, Feb. 16, 2015, International Search Report and Written Opinion.
U.S. Appl. No. 14/895,992, filed Dec. 4, 2015, Swartz.
EP 09835395.6, Mar. 16, 2016, Extended European Search Report.
PCT/US2014/049805, Feb. 18, 2016, International Preliminary Report on Patentability.
PCT/US2014/041009, Dec. 17, 2015, International Preliminary Report on Patentability.
Thöny-Meyer et al., Translocation to the periplasm and signal sequence cleavage of preapocytochrome c depend on sec and lep, but not on the ccm gene products. Eur J Biochem. Jun. 15, 1997;246(3):794-9.
Wuu et al., High yield cell-free production of integral membrane proteins without refolding or detergents. Biochim Biophys Acta. May 2008;1778(5):1237-50. doi: 10.1016/j.bbamem.2008.01.023. Epub Feb. 11, 2008.
Extended European Search Report for EP09835395.6 mailed Mar. 16, 2016.
International Preliminary Report on Patentability for PCT/US2014/049805, mailed Feb. 18, 2016.
International Preliminary Report on Patentability for PCT/US2014/041009, mailed Dec. 17, 2015.
Brady et al., Transfer of Pantoea citrea, Pantoea punctata and Pantoea terrea to the genus Tatumella emend. as Tatumella citrea comb. nov., Tatumella punctata comb. nov. and Tatumella terrea comb. nov. and description of Tatumella morbirosei sp. nov. Int J Syst Evol Microbiol. Mar. 2010;60(Pt 3):484-94. doi: 10.1099/ijs.0.012070-0. Epub Aug. 4, 2009.
Chisti et al., Disruption of microbial cells for intracellular products. Enzyme Micro Technol 1986;8(4):194-204. doi 10.1016/0141-0229(86)90087-6.
Daube et al., Cell-free co-synthesis of protein nanoassemblies: tubes, rings, and doughnuts. Nano Lett. Mar. 2007;7(3):638-41. Epub Feb. 2, 2007.
Horak et al., Two distinct proteolytic systems responsible for glucose-induced degradation of fructose-1,6-bisphosphatase and the Gal2p transporter in the yeast *Saccharomyces cerevisiae* share the same protein components of the glucose signaling pathway. J Biol Chem. Mar. 8, 2002;277(10):8248-54. Epub Dec. 28, 2001.
Kawarasaki et al., Prolonged cell-free protein synthesis in a batch system using wheat germ extract. Biosci Biotechnol Biochem. Oct. 1994;58(10):1911-3.
Kim et al., Regeneration of adenosine triphosphate from glycolytic intermediates for cell-free protein synthesis. Biotechnol Bioeng. Aug. 20, 2001;74(4):309-16.
Klemme, Photoproduction of hydrogen by purple bacteria: A critical evaluation of the rate limiting enzymatic steps. J Bioscience 1993;48 482-87.
Li et al., Rational strain improvement for enhanced clavulanic acid production by genetic engineering of the glycolytic pathway in *Streptomyces clavuligerus*. Metab Eng. May 2006;8(3):240-52. Epub Mar. 10, 2006.
Noireaux et al., Principles of cell-free genetic circuit assembly. Proc Natl Acad Sci U S A. Oct. 28, 2003;100(22):12672-7. Epub Oct. 14, 2003.
Schierle et al., The DsbA signal sequence directs efficient, cotranslational export of passenger proteins to the *Escherichia coli* periplasm via the signal recognition particle pathway. J Bacteriol. Oct. 2003;185(19):5706-13.
Spirin, High-throughput cell-free systems for synthesis of functionally active proteins. Trends Biotechnol. Oct. 2004;22(10):538-45. With Supplementary data.
Sroga et al., Periplasmic expression as a basis for whole cell kinetic screening of unnatural enzyme reactivities. Methods Enzymol. 2004;388:145-56.
Swartz, Universal cell-free protein synthesis. Nat Biotechnol. Aug. 2009;27(8):731-2. doi: 10.1038/nbt0809-731.

*pyrrole compounds*

3,4-dihydro-2H-pyrrole-2-carboxylic acid 3-hydroxy-3,4-dihydro-2H-pyrrole-2-carboxylic acid 4-methyl-3,4-dihydro-2H-pyrrole-2-carboxylic acid 3-hydroxy-4-methyl-3,4-dihydro-2H-pyrrole-2-carboxylic acid

*proline compounds* proline 3-hydroxyproline 4-methylproline 3-hydroxy-4-methylproline

CELL-FREE PREPARATION OF CARBAPENEMS

RELATED APPLICATIONS

The present application claims priority under 35 U.S.C. §119(e) to U.S. provisional patent application, U.S. Ser. No. 61/533,039, filed Sep. 9, 2011, which is incorporated herein by reference.

BACKGROUND OF THE INVENTION

In 1976, fermentation broths obtained from the soil bacteria *Streptomyces cattleya* were found to be active in screens for inhibitors of peptidoglycan biosynthesis. Initial attempts to isolate the active species proved difficult due to the chemical instability of that component. After many attempts and extensive purification, the material was finally isolated in >90% purity, allowing for the structural elucidation of the first isolated naturally-occurring carbapenem antibiotic, thienamycin. See, e.g., Kahan et al., *J. Antibiot.* (1979) 32:1-12.

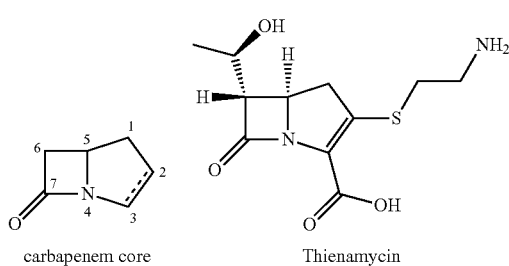

carbapenem core          Thienamycin

Since 1978 to 2000, over twenty-three total chemical syntheses of thienamycin have been reported, the large majority producing thienamycin after 12 or more sequential chemical steps in relatively low yield (e.g., from 0.2% to 10% yield). See, e.g., Salzmann et al., *J. Am. Chem. Soc.* (1980) 102:6161; Huang et al., *J. Am. Chem. Soc.* (1980) 102:2060; Reider et al., *Tetrahedron Letters* (1982) 23:2293-2296; Desiraju et al., *J. Chem. Soc. Chem. Comm.* (1984) 494; Evans et al., *Tetrahedron Letters* (1986) 27:4961; Grieco et al., *J. Am. Chem. Soc.* (1984) 106:6414; and Jacobi et al., *J. Org. Chem.* (1996) 61:2413. Production of thienamycin through traditional fermentation from *Streptomyces cattleya* also faced significant hurdles, such as low titer and difficulties in isolating and purifying thienamycin produced by fermentation. See, e.g., U.S. Pat. Nos. 3,950,357 and 4,006,060 each of which are incorporated herein by reference. Thienamycin was eventually considered ill-suited for clinical treatment due to its chemical instability due in aqueous media and biological instability to dehydropeptidase-I (DHP-I). Researchers have since sought alternatives to thienamycin which maintain thienamycin's excellent antibacterial activity but are unfettered with thienamycin's stability problems.

One such carbapenem, imipenem, was developed in 1985 as an intravenous product. See, e.g., U.S. Pat. No. 4,194,047 incorporated herein by reference. Imipenem has a broad spectrum of activity against aerobic and anaerobic Gram positive as well as Gram negative bacteria, and continues to be commonly used against *Pseudomonas aeruginosa*, one of the leading agents of nosocomial infections. The current manufacture of imipenem utilizes a chemical synthetic route which is, from simple building blocks to the final product, typically low yielding, resulting in high levels of waste production and high cost of manufacture. See, e.g., Grabowski, *Chirality* (2005) 17:S249-S259, and references cited therein.

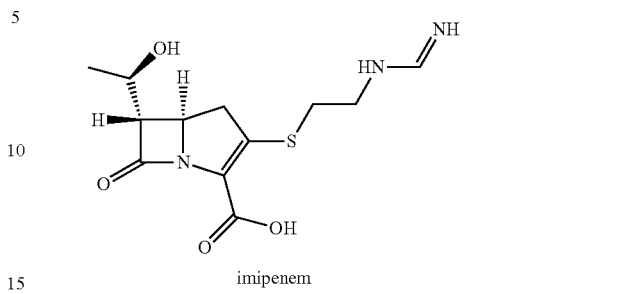

imipenem

Other promising carbapenem antibiotics have been found efficacious in humans, e.g., including ertapenem (INVANZ, Merck), meropenem (MERREM, Astra Zeneca), panipenem, biapenem, doripenem (FINIBAX, Johnson & Johnson), L-646591, and ER-35768, each for parenteral use; orally active carbapenems CL-191121, L-036, DU-6681, and R-95867, and their corresponding ester prodrugs L-084, DZ-2640, and CS-834. See, e.g., Kumagai et al., *Curr. Med. Chem.—Anti-Infective Agents* (2002) 1:1-14. Other carbapenems include, but are not limited to, saftrinem, tebipenem, tomopenem, S-4661, SM 216601, GV 129606, ZD-4433, R-83201, BO-2502A, BO-3482, DK-35C, DA-1131, S-4661, L-786,392, L-695256, L-786,392, GV104326, GV-118819, GV 143253, MK-0826, J-110,441, J-111225, FR-21818, DX-8739, CS-023, ME-1036, CP 5068, CL 188624, CL-190294, OCA-983, T-5575, and PZ-60. The majority of these carbapenems are produced by chemical synthesis.

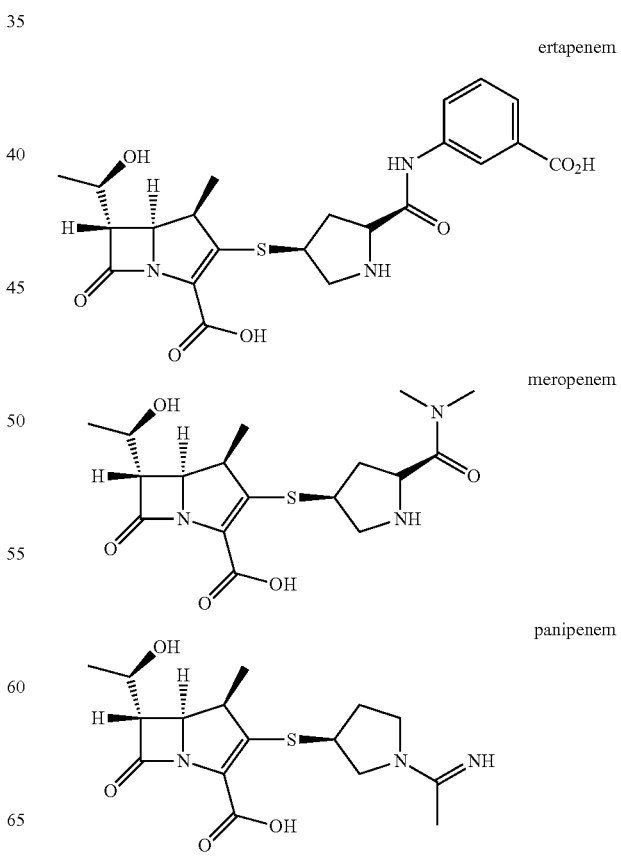

ertapenem meropenem panipenem biapenem doripenem

ER-35768 lenapenem

L-646591

CL-191121

L-036

L-084

DU-6681

DZ-2640

R-95867

-continued

CS-834

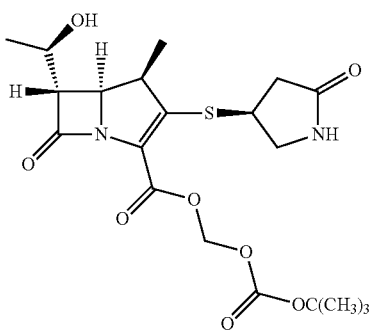

Thus there continues to remain a need for more efficient, environmentally friendly, and cost-effective processes for the production and development of existing and new carbapenems antibiotics.

SUMMARY OF THE INVENTION

The present invention provides cell-free systems, methods, and compositions (e.g., all lystates) useful in the generation of carbapenems and intermediates thereto.

In one aspect, provided is a cell lysate comprising a group of enzymes capable of generating a compound of the Formula (I-a):

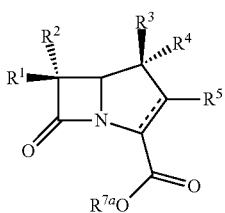

(I-a)

or a salt or tautomer thereof, or a combination thereof; from:
(1) glucose and glycine or salts thereof; and/or
(2) glucose and an optionally substituted glutamate of Formula (i):

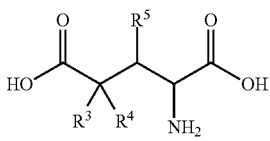

(i)

or salts thereof; and/or
(3) glucose and a proline compound of Formula (iv):

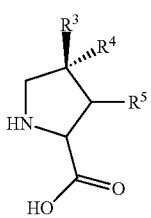

(iv)

or salts thereof; wherein $R^1$, $R^2$, $R^3$, $R^4$, $R^5$, and $R^{7a}$ are as defined herein, and ---- represents a single or double bond.

In another aspect, provided is a method of generating a compound of Formula (I-a):

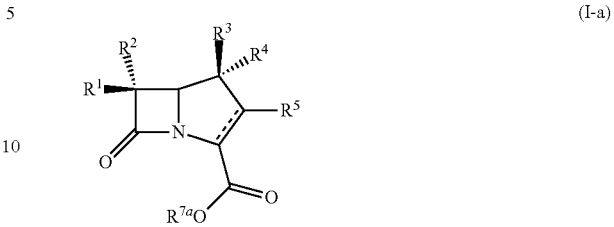

(I-a)

or a salt or tautomer thereof, or a combination thereof;
the method comprising:
providing a cell lysate comprising one or more enzymes, wherein the enzymes are selected from the group consisting of a kinase (e.g., a gamma-glutamyl kinase), a dehydrogenase (e.g., a Glu-5-P dehydrogenase), glycolysis/acetyl-CoA biosynthesis multi-enzyme, an acetyl-CoA acetyltransferase, a beta-oxidation multienzyme, a crotonyl-CoA reductase, an acetyl-CoA carboxylase, a malonyl-CoA reductase, a threonine aldolase, a beta-alanine transferase, a proline 3-hydroxylase, a proline oxidase, a carboxymethyl-Pro synthase, a carbapenam synthetase, a beta-lactam synthetase, a carbapenem synthase, a transferase, an oxygenase, a methyltransferase, and isozymes thereof;
wherein the one or more cell lysates are contacted with:
(1) glucose and glycine or salts thereof; and/or
(2) glucose and an optionally substituted glutamate of Formula (i):

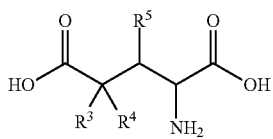

(i)

or salts thereof, and/or
(3) glucose and a proline compound of formula (iv):

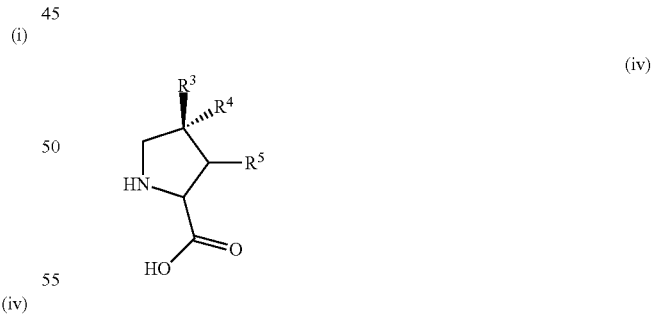

(iv)

or salts thereof; wherein $R^1$, $R^2$, $R^3$, $R^4$, $R^5$, and $R^{7a}$ are as defined herein, and the ---- represents a single or double bond. In certain embodiments, the ---- represents a single bond. In certain embodiments, the ---- represents a double bond. In certain embodiments, $R^1$ is hydrogen. In certain embodiments, $R^3$ is hydrogen or —$CH_3$. In certain embodiments, $R^2$ is hydrogen, —$CH_3$ or —$CH_2CH_3$. In certain embodiments, $R^4$ is hydrogen. In certain embodiments, $R^5$ is hydrogen or —OH.

In certain embodiments, the cell lysate is a lysate of an E. coli organism engineered to overexpress one or more enzymes. In certain embodiments, the cell lysate is a combination of different cell lysates, wherein each different lysate is engineered to overexpress one or more enzymes, e.g., one or more different enzymes or a different combination of two or more enzymes. In certain embodiments, the cell lysate is a lysate of a cell engineered to overexpress one or more enzymes selected from the group consisting of gamma-glutamyl kinase, Glu-5-P dehydrogenase, glycolysis/acetyl-CoA biosynthesis multi-enzyme, an acetyl-CoA acetyltransferase, a beta-oxidation multienzyme, a crotonyl-CoA reductase, an acetyl-CoA carboxylase, a malonyl-CoA reductase, a threonine aldolase, a beta-alanine transferase, a proline 3-hydroxylase, a proline oxidase, a carboxymethyl-Pro synthase, a carbapenam synthetase, a beta-lactam synthetase, a carbapenem synthase, a transferase, an oxygenase, a methyltransferase, and isozymes thereof. In certain embodiments, one or more enzymes selected from the group consisting of gamma-glutamyl kinase, Glu-5-P dehydrogenase, glycolysis/acetyl-CoA biosynthesis multi-enzyme, an acetyl-CoA acetyltransferase, a beta-oxidation multienzyme, a crotonyl-CoA reductase, an acetyl-CoA carboxylase, a malonyl-CoA reductase, a threonine aldolase, a beta-alanine transferase, a proline 3-hydroxylase, a proline oxidase, and isozymes thereof, were present in the cell prior to lysing. In certain embodiments, one or more enzymes are found in the cytoplasm of the cell prior to lysing. In certain embodiments, one or more enzymes selected from the group consisting of a carboxymethyl-Pro synthase, a carbapenam synthetase, a beta-lactam synthetase, a carbapenem synthase, a transferase, an oxygenase, and a methyltransferase, and isozymes thereof, are sequestered in the periplasmic space of the cell prior to lysing.

In certain embodiments, the glucose is enzymatically converted to an optionally substituted CoA compound of Formula (iii):

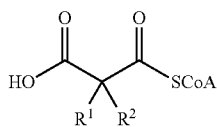

(iii)

or salt thereof; wherein —SCoA is Coenzyme A monoradical.

In certain embodiments, glucose and glycine are enzymatically converted to an optionally substituted glutamate semialdehyde of Formula (ii):

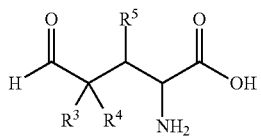

(ii)

or salt thereof; upon contact with acetyl-CoA carboxylase, malonyl-CoA reductase, threonine aldolase, a kinase, and a dehydrogenase.

In certain embodiments, the optionally substituted glutamate of Formula (i):

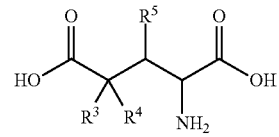

(i)

is converted to an optionally substituted glutamate semialdehyde compound of Formula (ii):

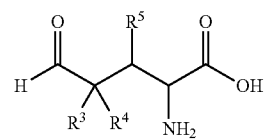

(ii)

or salt thereof; upon contact with a kinase and a dehydrogenase.

In certain embodiments, the optionally substituted glutamate semialdehyde compound of Formula (ii):

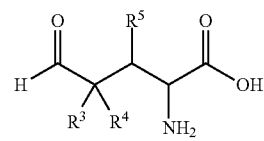

(ii)

or salt thereof, cyclizes to form a pyrrole compound of formula:

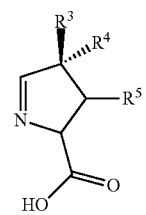

(v)

or salt thereof, and water as a by-product.

In certain embodiments, the proline compound of Formula (iv):

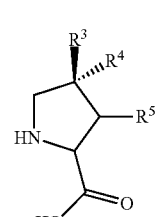

(iv)

or salt thereof, is enzymatically converted to a pyrrole compound of formula:

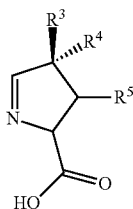

or salt thereof; upon contact with a proline oxidase.

In certain embodiments, the proline compound of Formula (iv):

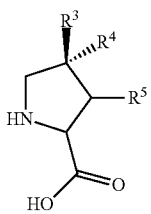

(iv)

or salt thereof, wherein $R^5$ is hydrogen, is enzymatically converted to a 3-hydroxylated proline compound of formula:

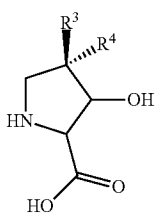

(iv-a)

or salt thereof; upon contact with a proline-3-hydroxylase.

In certain embodiments, the 3-hydroxylated proline compound of formula:

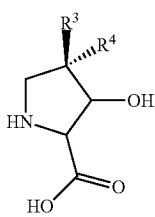

(iv-a)

or salt thereof, is enzymatically converted to a 3-hydroxylated pyrrole compound of formula:

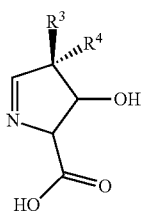

(v-a)

or salt thereof, upon contact with a proline oxidase.

In certain embodiments, the optionally substituted glutamate of Formula (i):

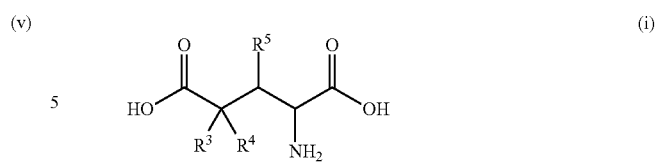

(i)

or salt thereof, is enzymatically converted to a proline compound of Formula (iv):

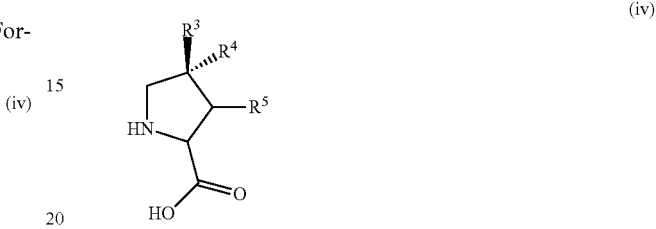

(iv)

or salt thereof; upon contact with the γ-glutamyl kinase-GP-reductase multienzyme complex (e.g., *E. coli* ProB and ProA).

In certain embodiments, the enzyme-containing cell lysate converts the combination of glucose and glycine, or the combination of glucose and an optionally substituted glutamate of the Formula (i) to an optionally substituted CoA compound of Formula (iii), or salt thereof, and an optionally substituted glutamate semialdehyde of Formula (II), or salt thereof:

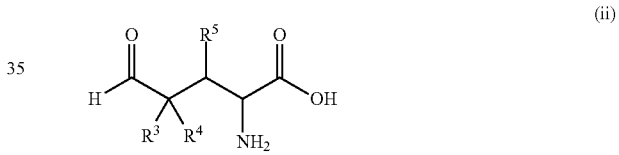

(ii)

(iii)

wherein —SCoA is Coenzyme A monoradical.

In certain embodiments, the optionally substituted glutamate semialdehyde of Formula (ii) and the optionally substituted CoA compound of Formula (iii) generate a pyrrolidinyl compound of Formula (II-a):

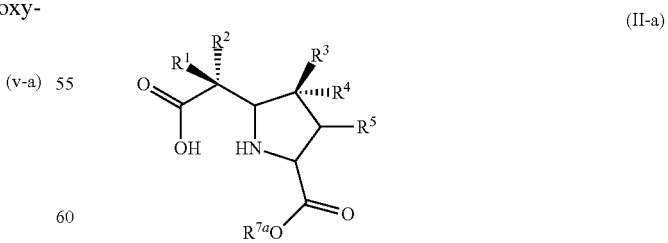

(II-a)

or salt thereof, wherein $R^{7a}$ is hydrogen, upon contact with an enzyme, optionally released from the periplasmic space.

In certain embodiments, the enzyme-containing cell lysate converts the combination of glucose and the proline compound of Formula (iv) to an optionally substituted CoA compound of Formula (iii), or salt thereof, and an pyrrole compound of Formula (v), or salt thereof:

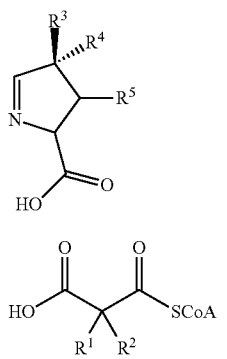

wherein —SCoA is Coenzyme A monoradical.

In certain embodiments, the pyrrole compound of Formula (v) or salt thereof and the optionally substituted CoA compound of Formula (iii) generate a pyrrolidinyl compound of Formula (II-a):

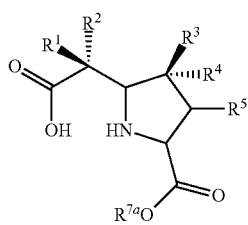

or salt thereof, wherein $R^{7a}$ is hydrogen, upon contact with an enzyme, optionally released from the periplasmic space.

In certain embodiments, the pyrrolidinyl compound (II-a) generates a β-lactam compound of Formula (III-a):

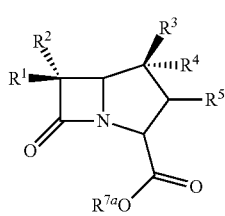

or salt thereof, upon contact with an enzyme, optionally released from the periplasmic space.

In certain embodiments, the β-lactam compound of Formula (III-a) generates a compound of Formula (I-a):

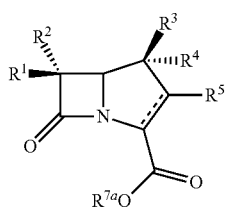

or salt thereof, wherein ---- represents a double bond, upon contact with an enzyme, optionally released from the periplasmic space.

In certain embodiments, when $R^5$ is hydrogen, and ---- represents a double bond, the compound of Formula (I-a):

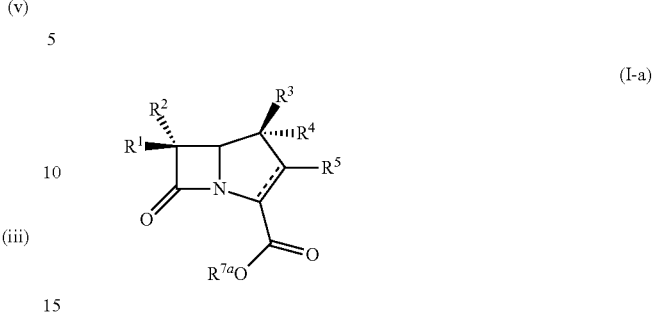

or a salt thereof; is contacted with a transferase enzyme and a compound of the formula $HSR^8$, wherein $R^8$ is as defined herein; to provide a thiol-containing compound of Formula (I-c):

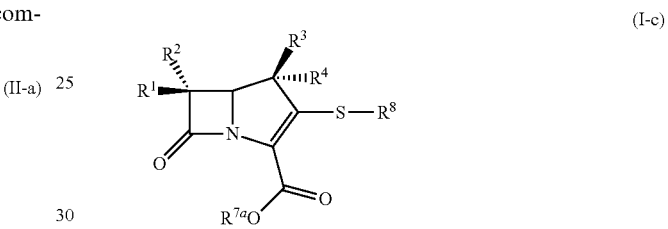

or salt thereof. In certain embodiments, $R^8$ is an optionally substituted alkyl, optionally substituted heteroalkyl, or optionally substituted heterocyclyl.

In certain embodiments, when ---- represents a double bond, and $R^5$ is —OH, the compound of Formula (I-a):

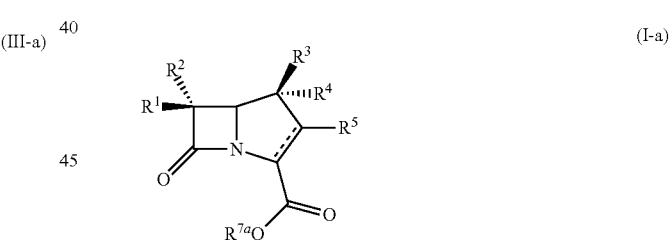

or a salt or tautomer thereof, or a combination thereof; is contacted with a compound of the formula $R^{8'}$—X wherein X is a leaving group, and $R^{8'}$ is as defined herein, to provide a compound of Formula (I-e):

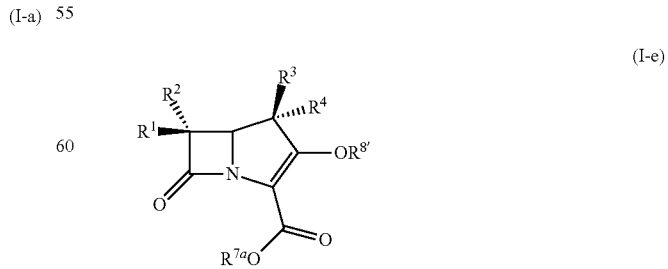

or salt thereof.

In certain embodiments, the compound of Formula (I-e) is contacted with a compound of the formula HSR$^8$, wherein R$^8$ is as defined herein, to provide a thiol-containing compound of Formula (I-c):

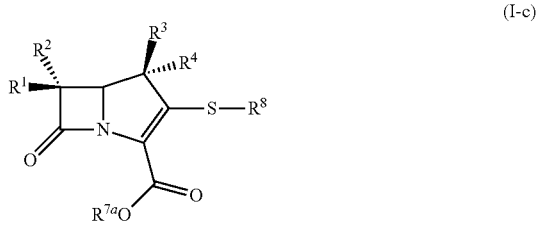

(I-c)

or salt thereof.

In certain embodiments, when R$^2$ is —CH$_3$, the compound of Formula (I-a) is contacted with an oxygenase enzyme to provide a hydroxylated compound, wherein R$^2$ is —CH$_2$OH. In certain embodiments, when R$^2$ is —CH$_2$CH$_3$, the compound of Formula (I-a) is contacted with an oxygenase enzyme to provide a hydroxylated compound, wherein R$^2$ is —CH(OH)CH$_3$.

In certain embodiments, wherein R$^1$ and R$^2$ are both hydrogen, the method comprises contacting a compound of Formula (I-a) with a methyltransferase (e.g., *S. cattalya* ThnL, ThnP, ThnK, or isozyme thereof) to provide a compound, wherein R$^2$ is alkyl, e.g., —CH$_3$ (methyl, Me) or —CH$_2$CH$_3$ (ethyl, Et).

In yet another aspect, provided are pharmaceutical compositions comprising a compound or salt thereof prepared by the inventive cell-free system and optionally a pharmaceutically acceptable excipient.

In another aspect, provided is a method of treating a bacterial infection, comprising administering a therapeutically effective amount of a compound generated by the inventive cell-free system or a pharmaceutical composition thereof to a subject in need thereof.

The details of one or more embodiments of the invention are set forth in the accompanying Figures and the Detailed Description. Other features, objects, and advantages of the invention will be apparent from the description and from the claims.

DEFINITIONS

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —CH$_3$). In certain embodiments, the alkyl group is a substituted $C_{1-10}$ alkyl.

"Perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-6}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include —CF$_3$, —CF$_2$CF$_3$, —CF$_2$CF$_2$CF$_3$, —CCl$_3$, —CFCl$_2$, —CF$_2$Cl, and the like.

The term "heteroalkyl" refers to an alkyl group, as defined herein, wherein at least one oxygen, nitrogen, or sulfur heteroatom (e.g., 1, 2, 3, 4, 1-2, 1-3, 1-4, 2-4, 3-4, or 2-3 heteroatoms, inclusive) is present in the backbone of the alkyl chain, i.e., present between one or more carbon atoms of the alkyl chain. In certain embodiments, the heteroalkyl group is an unsubstituted heteroC$_{1-10}$ alkyl. In certain embodiments, the heteroalkyl group is a substituted heteroC$_{1-10}$ alkyl.

As used herein, "alkenyl" refers to a radical of a straight-chain or branched unsaturated hydrocarbon group having from 2 to 10 carbon atoms and one or more carbon-carbon double bonds, e.g., 1, 2, 3, or 4 double bonds, and no carbon-carbon triple bonds ("C$_{2-10}$ alkenyl"). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl.

The term "heteroalkenyl" refers to an alkenyl group, as defined herein, wherein at least one oxygen, nitrogen, or sulfur heteroatom (e.g., 1, 2, 3, 4, 1-2, 1-3, 1-4, 2-4, 3-4, or 2-3 heteroatoms, inclusive) is present in the backbone of the alkenyl chain, i.e., present between one or more carbon atoms of the alkenyl chain. In certain embodiments, the heteroalkenyl group is an unsubstituted heteroC$_{2-10}$ alkenyl. In certain embodiments, the heteroalkenyl group is a substituted heteroC$_{2-10}$ alkenyl.

As used herein, "alkynyl" refers to a radical of a straight-chain or branched unsaturated hydrocarbon group having from 2 to 10 carbon atoms, one or more carbon-carbon triple bonds, e.g., 1, 2, 3, or 4 triple bonds, and optionally one or more carbon-carbon double bonds, e.g., 1, 2, 3, or 4 double bonds ("C$_{2-10}$ alkynyl"). An alkynyl group which includes one or more double bonds is also referred to as an "ene-yne". In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

The term "heteroalkynyl" refers to an alkynyl group, as defined herein, wherein at least one oxygen, nitrogen, or sulfur heteroatom (e.g., 1, 2, 3, 4, 1-2, 1-3, 1-4, 2-4, 3-4, or 2-3 heteroatoms, inclusive) is present in the backbone of the alkynyl chain, i.e., present between one or more carbon atoms of the alkynyl chain. In certain embodiments, the heteroalkynyl group is an unsubstituted heteroC$_{2-10}$ alkynyl. In certain embodiments, the heteroalkynyl group is a substituted heteroC$_{2-10}$ alkynyl.

As used herein, "carbocyclyl" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"). In some embodiments, a carbocyclyl group has 3 to 6 ring carbon atoms ("C$_{3-6}$ carbocyclyl"). In some embodiments, a carbocyclyl group has 3 to 6 ring carbon atoms ("C$_{3-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-10}$ cycloalkyl. In certain embodiments, the cycloalkyl group is a substituted $C_{3-10}$ cycloalkyl.

As used herein, "heterocyclyl" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, thiorenyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group, as defined herein, substituted by an aryl group, as defined herein, wherein the point of attachment is on the alkyl moiety.

As used herein, "heteroaryl" refers to a radical of a 5-14 membered monocyclic or polycyclic (e.g., bicyclic or tricyclic) 4n+2 aromatic ring system (e.g., having 6, 10, or 14π electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group, as defined herein, substituted by a heteroaryl group, as defined herein, wherein the point of attachment is on the alkyl moiety.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

Alkyl, alkenyl, alkynyl, heteroalkyl, heteroalkenyl, heteroalkynyl, carbocyclyl, heterocyclyl, aryl, and heteroaryl groups, as defined herein, are optionally substituted (i.e., substituted or unsubstituted). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, alkyl)$_2$, alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —OC$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$ (C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S;

wherein X$^-$ is a counterion.

As used herein, the term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein.

As used herein, the term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —$SR^{aa}$, —S═$SR^{cc}$, —SC(═S)$SR^{aa}$, —SC(═O)$SR^{aa}$, —SC(═O)$OR^{aa}$, and —SC(═O)$R^{aa}$, wherein $R^{aa}$ and $R^{cc}$ are as defined herein.

As used herein, the term, "amino" refers to the group —$NH_2$. The term "substituted amino," by extension, refers to a monosubstituted amino, a disubstituted amino, or a trisubstituted amino, as defined herein. In certain embodiments, the "substituted amino" is a monosubstituted amino or a disubstituted amino group.

As used herein, the term "monosubstituted amino" refers to an amino group wherein the nitrogen atom directly attached to the parent molecule is substituted with one hydrogen and one group other than hydrogen, and includes groups selected from —NH($R^{bb}$), —NHC(═O)$R^{aa}$, —$NHCO_2R^{aa}$, —NHC(═O)N($R^{bb}$)$_2$, —NHC(═$NR^{bb}$)N($R^{bb}$)$_2$, —$NHSO_2R^{aa}$, —NHP(═O)(O$R^{cc}$)$_2$, and —NHP(═O)(N$R^{bb}$)$_2$, wherein $R^{aa}$, $R^{bb}$ and $R^{cc}$ are as defined herein, and wherein $R^{bb}$ of the group —NH($R^{bb}$) is not hydrogen.

As used herein, the term "disubstituted amino" refers to an amino group wherein the nitrogen atom directly attached to the parent molecule is substituted with two groups other than hydrogen, and includes groups selected from —N($R^{bb}$)$_2$, —$NR^{bb}$C(═O)$R^{aa}$, —$NR^{bb}CO_2R^{aa}$, —$NR^{bb}$C(═O)N($R^{bb}$)$_2$, —$NR^{bb}$C(═$NR^{bb}$)N($R^{bb}$)$_2$, —$NR^{bb}SO_2R^{aa}$, —$NR^{bb}$P(═O)(O$R^{cc}$)$_2$, and —$NR^{bb}$P(═O)(N$R^{bb}$)$_2$, wherein $R^{aa}$, $R^{bb}$, and $R^{cc}$ are as defined herein, with the proviso that the nitrogen atom directly attached to the parent molecule is not substituted with hydrogen.

As used herein, the term "trisubstituted amino" refers to an amino group wherein the nitrogen atom directly attached to the parent molecule is substituted with three groups, and includes groups selected from —N($R^{bb}$)$_3$ and —N($R^{bb}$)$_3^+$ $X^-$, wherein $R^{bb}$ and $X^-$ are as defined herein.

As used herein, the term "oxo" refers to the group ═O, and the term "thiooxo" refers to the group ═S.

As used herein, a "counterion" is a negatively charged group associated with a positively charged quarternary amine in order to maintain electronic neutrality. Exemplary counterions include halide ions (e.g., $F^-$, $Cl^-$, $Br^-$, $I^-$), $NO_3^-$, $ClO_4^-$, $OH^-$, $H_2PO_4^-$, $HSO_4^-$, sulfonate ions (e.g., methanesulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —$OR^{aa}$, —N($R^{cc}$)$_2$, —CN, —C(═O)$R^{aa}$, —C(═O)N($R^{cc}$)$_2$, —$CO_2R^{aa}$, —$SO_2R^{aa}$, —C(═$NR^{bb}$)$R^{aa}$, —C(═$NR^{cc}$)O$R^{aa}$, —C(═$NR^{cc}$)N($R^{cc}$)$_2$, —$SO_2$N($R^{cc}$)$_2$, —$SO_2R^{cc}$, —$SO_2OR^{cc}$, —$SOR^{aa}$, —C(═S)N($R^{cc}$)$_2$, —C(═O)$SR^{cc}$, —C(═S)$SR^{cc}$, —P(═O)$_2R^{aa}$, —P(═O)($R^{aa}$)$_2$, —P(═O)$_2$N($R^{cc}$)$_2$, —P(═O)$_2$N($R^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an amino protecting group. Amino protecting groups include, but are not limited to, —OH, —$OR^{aa}$, —N($R^{cc}$)$_2$, —C(═O)$R^{aa}$, —C(═O)N($R^{cc}$)$_2$, —$CO_2R^{aa}$, —$SO_2R^{aa}$, —C(═$NR^{cc}$)$R^{aa}$, —C(═$NR^{cc}$)O$R^{aa}$, —C(═$NR^{cc}$)N($R^{cc}$)$_2$, —$SO_2$N($R^{cc}$)$_2$, —$SO_2R^{cc}$, —$SO_2OR^{cc}$, —$SOR^{aa}$, —C(═S)N($R^{cc}$)$_2$, —C(═O)$SR^{cc}$, —C(═S)$SR^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Amino protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

These and other exemplary substituents are described in more detail in the Detailed Description, the Examples and in the claims. The invention is not intended to be limited in any manner by the above exemplary listing of substituents.

As used herein, the term "salt" or "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As used herein, the term "prodrug" refers to a derivative of a parent compound that requires transformation within the body in order to release the parent compound. In certain cases, a prodrug has improved physical and/or delivery properties over the parent compound. Prodrugs are typically designed to enhance pharmaceutically and/or pharmacokinetically based properties associated with the parent compound. The advantage of a prodrug can lie in its physical properties, such as enhanced water solubility for parenteral administration at physiological pH compared to the parent compound, or it enhances absorption from the digestive tract, or it may enhance drug stability for long-term storage.

As used herein, the term "tautomer" refers to particular isomers of a compound in which a hydrogen and double bond have changed position with respect to the other atoms of the molecule. For a pair of tautomers to exist there must be a mechanism for interconversion. Examples of tautomers include keto-enol forms, imine-enamine forms, amide-imino alcohol forms, amidine-aminidine forms, nitroso-oxime forms, thio ketone-enethiol forms, N-nitroso-hydroxyazo forms, nitro-aci-nitro forms, and pyridone-hydroxypyridine forms.

As used herein, "cell-free" refers to a composition substantially free of intact cells. One of skill in the art would understand that a certain percentage of the cells after lysing may be intact, e.g., less than 10%, less than 5%, less than 2%, less than 1%, or less than 0.5%.

As used herein, a "protein" comprises a polymer of amino acid residues linked together by peptide bonds. The term, as used herein, refers to proteins, polypeptides, and peptide of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein may also be a single molecule or may be a multi-molecular complex. A protein may be just a fragment of a naturally occurring protein or peptide. A protein may be naturally occurring, recombinant, or synthetic, or any combination of these.

As used herein, a "nucleic acid" refers to a polymer of nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-idouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, 4-acetylcytidine, 5-(carboxyhydroxymethyl)uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2'-O-methylcytidine, arabinose, and hexose), or modified phosphate groups (e.g., phosphorothioates and 5'-N-phosphoramidite linkages).

As used herein, an "isozyme" refers to an enzyme that differs in amino acid sequence but catalyzes the same chemical reaction or produces the same reaction product from starting material.

As used herein, a "leaving group" is an art-understood term referring to a molecular fragment that departs with a pair of electrons in heterolytic bond cleavage, wherein the molecular fragment is an anion or neutral molecule. See, for example, Smith, March *Advanced Organic Chemistry* 6th ed. (501-502). Exemplary leaving groups include, but are not limited to, halo (e.g., chloro, bromo, iodo) and sulfonyl substituted hydroxyl groups (e.g., tosyl, mesyl, besyl).

"Co-enzyme A monoradical" (—S-CoA) refers to a group of the formula:

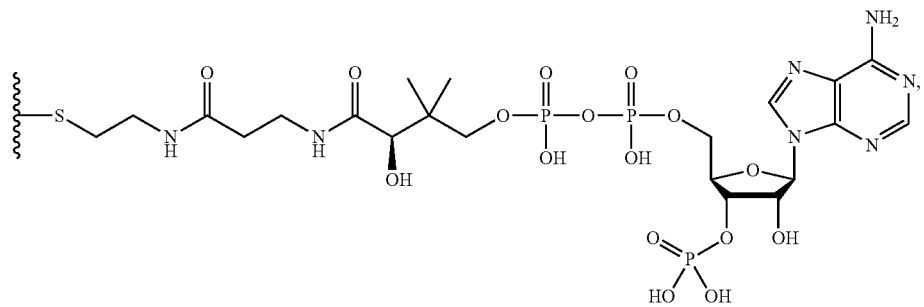

or salt thereof.

DETAILED DESCRIPTION OF CERTAIN EMBODIMENTS OF THE INVENTION

Figure 1:
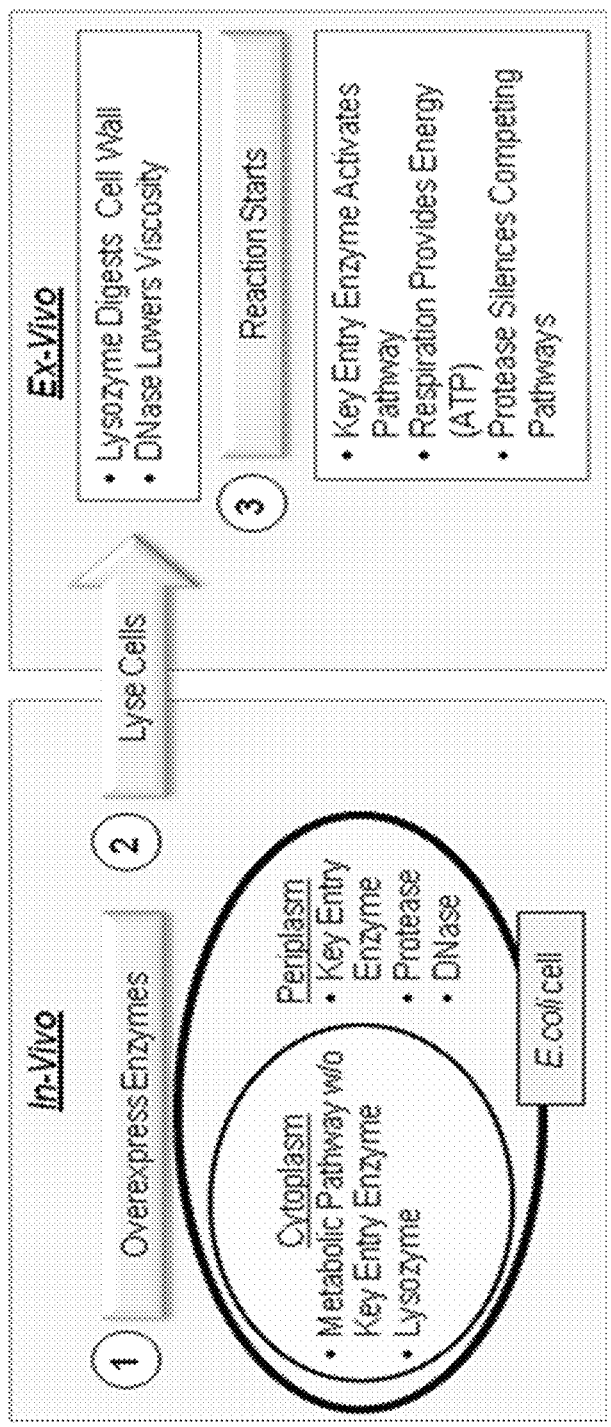
FIG. 1 depicts a generalized schematic of the inventive cell-free process: overexpression of enzymes in an *E. coli* cell (in vivo step); lysing the *E. coli* cell to provide a cell lysate; and production of a carbapenem using the cell lysate (ex vivo step).

Historically, cell-free systems have provided a useful tool for harnessing the natural capabilities of complex biological systems. Cell-free protein synthesis systems (CFPS) were shown to provide a promising platform for the synthesis of proteins that are difficult to prepare in vivo, including patient-specific vaccine candidates and pharmaceutical proteins. See, e.g., Yang et al., *Biotechnol. Bioeng.* (2005) 89:503-511, and Goerke et al., *Biotechnol. Bioeng.* (2008) 99:351-367. Despite these promising applications, CFPS were limited by their inability to generate the energy needed for protein synthesis, and a continuous feed of expensive energy substrates was required. One-step phosphorylation reactions driven by phosphoenolpyruvate (PEP) and similar compounds have been used to supply the energy required for long lived protein production, but this process is not very effective as it only generates bursts of ATP for a limited duration while at the same time generating inhibitory phosphate. See, e.g., Swartz, *J. Ind. Microbiol. Biotechnol.* (2006) 33:476-485. Recently, researchers have addressed these issues with a cell-free system that stabilizes amino acid supply and activates central metabolism along with oxidative phosphorylation to dramatically reduce substrate costs and simplify cell-free scale-up. See, e.g., Calhoun et al., *J. Biotechnol.* (2006) 123:193-203; Michel-Reydellet et al., *Metabolic Engineering* (2004) 6:197-203; Jewett et al., *Mol. Syst. Biol.* (2008) 4:220; and Calhoun et al., *Biotechnology and Bioengineering* (2005) 90:606-613. These systems have been adapted to the cell-free production of small organic molecules such as shikimic acid. See, e.g., PCT publication WO2010/074760. Cell-free synthesis exploits the open nature of cell-free reactions and has significant advantages over both chemical synthesis and fermentation-based approaches to chemical production, including having: i) the ability to produce chemicals with a high degree of cytotoxicity, such as antibiotics; ii) the ability to shunt all carbon to the chemical product of interest, increasing productivity; iii) the ability to more effectively control the flux of reducing equivalents and the recycling of electron carriers; iv) the ability to directly add biosynthetic substrates; and/or v) the potential for more efficient product harvesting and rapid scale-up. Cell-free systems can direct most, if not all, of the metabolic resources of the cell towards the exclusive production of one pathway. Moreover, the lack of a cell wall in vitro is advantageous since it allows for control of the synthetic environment. The redox potential, pH, or ionic strength can also be altered with greater flexibility than in vivo since one is not concerned about cell growth or viability. Furthermore, direct recovery of products can more easily be achieved.

The present invention seeks to build from these efforts methods for generating compounds of Formula (I):

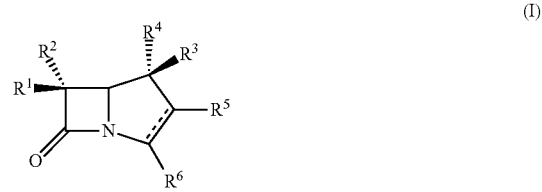

or salts or tautomers thereof, or combinations thereof; wherein:

each instance of $R^1$, $R^2$, $R^3$, and $R^4$ is independently selected from the group consisting of hydrogen, optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, and optionally substituted heteroaryl;

$R^5$ is selected from the group consisting of hydrogen, —OR$^8$, —SR$^8$, —S(=O)R$^8$, —S(=O)$_2$R$^8$, and —N(R$^8$)$_2$, wherein each instance of R$^8$ is independently selected from the group consisting of hydrogen, optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, optionally substituted heteroaryl, —C(=O)R$^{8a}$, —C(=O)OR$^{8a}$, —C(=O)SR$^{8a}$, —C(=O)N(R$^{8b}$)$_2$, —C(=NR$^{8b}$)R$^{8a}$, —C(=NR$^{8b}$)OR$^{8a}$, —C(=NR$^{8b}$)SR$^{8a}$, —C(=NR$^{8b}$)N(R$^{8b}$)$_2$, —C(=S)R$^{8a}$, —C(=S)OR$^{8a}$, —C(=S)SR$^{8a}$, —C(=S)N(R$^{8b}$)$_2$, —C(=O)NR$^{8b}$SO$_2$R$^{8a}$, —S(=O)R$^{8a}$, —SO$_2$R$^{8a}$, —SO$_2$N(R$^{8a}$)$_2$, —Si(R$^{8a}$)$_3$, —P(=O)(R$^{8a}$)$_2$, —P(=O)(OR$^{8a}$)$_2$, —P(=O)(R$^{8a}$)(OR$^{8a}$), —P(=O)(R$^{8a}$)(N(R$^{8b}$)$_2$), —P(=O)(N(R$^{8b}$)$_2$)$_2$, —P(=O)$_2$R$^{8a}$, —P(=O)$_2$OR$^{8a}$, —P(=O)$_2$N(R$^{8b}$)$_2$, —B(R$^{8a}$)$_2$, —B(OR$^{8a}$)$_2$, and —BR$^{8a}$(OR$^{8a}$), wherein R$^{8a}$ is selected from the group consisting of optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, optionally substituted heteroaryl, if attached to an oxygen atom an oxygen protecting group, and if attached to a sulfur atom a sulfur protecting group, or two R$^{8a}$ groups or an R$^{8a}$ and R$^{8b}$ group are joined to form an optionally substituted heterocyclic ring; and each instance of R$^{8b}$ is independently selected from the group consisting of hydrogen, optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, optionally substituted heteroaryl, and a nitrogen protecting group, or two R$^{8b}$ are joined to form an optionally substituted heterocyclic ring;

$R^6$ is selected from the group consisting of optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, optionally substituted heteroaryl, and —C(=O)R$^7$, wherein each instance of R$^7$ is selected from hydrogen, —OR$^{7a}$, —SR$^{7a}$, or —N(R$^{7b}$)$_2$, wherein R$^{7a}$ is selected from the group consisting of hydrogen, optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, optionally substituted heteroaryl, if attached to an oxygen atom an oxygen protecting group, and if attached to a sulfur atom a sulfur protecting group; and each instance of R$^{7b}$ is independently selected from the group consisting of hydrogen, optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, optionally substituted heteroaryl, and a nitrogen protecting group, or two R$^{7b}$ are joined to form an optionally substituted heterocyclic ring; and ---- represents a single or double bond.

It is understood that when ---- represents a double bond, and R$^5$ is OH, SH, or NHR$^8$, the compound of Formula (I) may exist as a mixture of at least two tautomers (i.e., the enol and keto form):

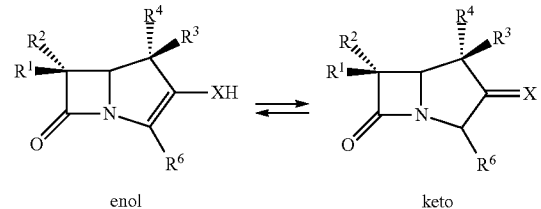

enol          keto wherein X is O, S, or NR$^8$.

In one aspect, the method comprises providing a cell or group of cells which are engineered to express one or more enzymes capable of generating a carbapenem of the present invention from a combination of glucose, glycine, and/or a compound of Formula (i). In certain embodiments, one or more of these enzymes are found in the cytoplasm prior to cell lysis. In certain embodiments, one or more of these enzymes are sequestered in the periplasmic space prior to call lysis. In certain embodiments, the cell or group of cells are lysed to provide a cell lysate which comprises a mixture of enzymes released from the cytoplasm, and optionally the periplasmic space. In certain embodiments, the enzyme-containing cell lysate is then "fed" glucose, glycine, and/or a compound of Formula (i) to generate a carbapenem as described herein. In certain embodiments, the process further encompasses one or more additional chemical and/or enzymatic steps to provide a wide variety of carbapenems, e.g., a compound encompassed by Formula (I).

In another aspect, the method comprises providing a cell or group of cells which are engineered to express one or more enzymes capable of generating a carbapenem as described herein from a combination of glucose and a proline compound of Formula (iv). In certain embodiments, one or more of these enzymes are found in the cytoplasm prior to lysis space. In certain embodiments, one or more of these enzymes are sequestered in the periplasmic space. In certain embodiments, the cell or group of cells are lysed to provide a cell lysate which comprises a mixture of enzymes released from the cytoplasm, and optionally the periplasmic space. In certain embodiments, the enzyme-containing cell lysate is then "fed" glucose and a proline compound of Formula (iv) to generate a carbapenem as described herein. In certain embodiments, the process further encompasses one or more additional chemical and/or enzymatic steps to provide a wide variety of carbapenems, e.g., a compound encompassed by Formula (I).

Representative enzymes associated with various aspects of the invention are provided in Tables 1 and 2. In some embodiments, one or more enzymes provided in Table 1 are expressed in an organism. In some embodiments, one or more enzymes provided in Table 2 are expressed in an organism. Tables 1 and 2 are intended to be non-limiting examples of enzymes useful in performing one or more steps of the present invention. Other enzymes able to elicit the same reaction or produce the same reaction product from a starting material, e.g., an isozyme thereof, are also contemplated as useful in performance of one or more methods of the present invention.

TABLE 1

| Rxn | Description | Organism(s) | EC | GenBank | Uniprot | Enzyme |
|---|---|---|---|---|---|---|
| a | kinase | E. coli | 2.7.2.11 | AAC73346.1 | P0A7B5 | ProB |
| b | dehydrogenase | E. coli | 1.2.1.41 | AAC73347.1 | P07004 | ProA γ-glutamyl kinase-GP-reductase multienzyme complex (ProB + ProA) |
| c | glycolysis; Acetyl-CoA biosynthesis multienzyme | E. coli | 2.7.1.2<br>5.3.1.9<br>2.7.1.11<br>4.1.2.13<br>5.3.1.1<br>1.2.1.12<br>2.7.2.3<br>5.4.2.1<br>4.2.1.11<br>2.7.1.40<br>2.7.1.40<br>1.2.4.1<br>2.3.1.12 | AAC75447.1<br>AAC76995.1<br>AAC76898.1<br>AAC75962.1<br>AAC76901.1<br>AAC74849.1<br>AAC75963.1<br>AAC73842.1<br>AAC75821.1<br>AAC74924.1<br>AAC74746.1<br>AAC73225.1<br>AAC73226.1 | P0A6V8<br>P0A6T1<br>P0A796<br>P0AB71<br>P0A858<br>P0A9B2<br>P0A799<br>P62707<br>P0A6P9<br>P21599<br>P0AD61<br>P0AFG8<br>P06959 | Glk<br>Pgi<br>PfkA<br>Fba<br>TpiA<br>GapA<br>Pgk<br>GpmA<br>Eno<br>PykA<br>PykF<br>AceE<br>AceF |
| d | Acetyl-CoA acetyl-transferase | Rhodobacter sphaeroides, expressed/active in E. coli (J. Biosci. Bioeng. (2007) 103:38). | 2.3.1.9 | ABA79923.1 | Q3IZW1 | PhaA |
| e | β-oxidation multienzyme (S-hydratase and 3-hydroxyacyl-CoA dehydrogenase activities) | E. coli | | AAC76849.1 | P21177 | FadB |
| f | Crotonyl-CoA reductase | Rhodobacter sphaeroides, expressed/active in E. coli (PNAS (2007) 104:10631). | 1.3.1.85 | ACJ71669.1 | B8XVS5 | Ccr |
| g | Acetyl-CoA carboxylase | E. coli | 6.4.1.2 | AAC73296.1 | P0ABD5<br>P0ABD8<br>P24182<br>P0A9Q5 | AccA, AccB, AccC, AccD ("AccABCD" complex) |
| h | Malonyl-CoA reductase | Sulfolobus tokodaii, expressed in E. coli (J. Bacteriol. (2006) 188:8551). | 1.2.1.75 | BAB67276.1 | Q96YK1 | Mcr |
| i | threonine aldolase | E. coli, active on succinic semialdehyde (Tetrahedron (2008) 64:5079). | 4.1.2. | AAC73957.1 | P75823 | LtaE |
| j | β-alanine transaminase | Pseudomonas putida, | 2.6.1.18 | | P28269 | β-alanine transaminase |
| k | proline 3-hydroxylase | Streptomyces sp. | 1.14.11.28 | BAA22406.1 | P96010 | P3H1 |
| m | proline oxidase | E. coli | 1.5.99.8 | AAB59985.1 | P09546 | PutA |

*alternative enzyme

TABLE 2

| Rxn | Description | Organism(s) | GenBank | Uniprot | Enzyme |
|---|---|---|---|---|---|
| 1 | CMP synthase | P. carotovorum; (see, e.g., Hamed et al., Chembiochem (2009) 10:246-250); expressed in E. coli (see, e.g., Sleeman et al., J. Biol. Chem. (2004) 279:6730-6736) | AAD38230.1 | Q9XB60 | CarB |

TABLE 2-continued

| Rxn | Description | Organism(s) | GenBank | Uniprot | Enzyme |
|---|---|---|---|---|---|
| 1* | CMP synthase* | Streptomyces cattleya; expressed in E. coli (see, e.g., Hamed et al., Chembiochem (2009) 10:246-250) | CAD18973.1 | Q83XP9 | ThnE* |
| 2 | carbapenam synthetase | P. carotovorum expressed in E. coli (see, e.g., Sleeman et al., J. Biol. Chem. (2004) 279:6730-6736) | AAD38229.1 | Q9XB61 | CarA |
| 2* | β-lactam synthetase* | S. cattleya ThnM 53% similarity to S. clavuligerus β-lactam synthetase (Chem & Biol. (2003) 10:301) | CAD18981.1 | Q83XP1 | ThnM* |
| 3 | carbapenem synthase | P. carotovorum; (see, e.g., Reider et al., Tetrahedron Letters (1982) 23:2293-2296); expressed in E. coli (see, e.g., Stapon et al., J. Am. Chem. Soc. (2003) 125:15746-15747) | AAD38231.1 | Q9XB59 | CarC |
| 3* | carbapenem synthase* | Streptomyces cattleya; expressed in E. coli (see, e.g., Bodner et al. JACS (2009) 131:14345-14354) | CAD18975.1 | Q83XP7 | ThnG* |
| 4 | putative transferase | S. cattleya; 54% similarity to E. coli glutathione transferase (see, e.g., Nunez et al., Chem. Biol. (2003) 10:301-311) | CAD18990.1 | Q83XN2 | ThnV |
| 5 | oxygenase | S. cattleya (ThnQ); oxygenase may also react with on product of steps 2 or 3 (see, e.g., Bodner et al., J. Am. Chem. Soc. (2010) 132:12-13); expressed in E. coli (see, e.g., Bodner et al. JACS (2009) 131:14345-14354) | CAD18985.1 | Q83XN7 | ThnQ |
| 5* | Oxygenase* | | | | enzymes of the 2-oxoglutarate and Fe(II)-dependent oxygenase superfamily* |
| 6 | putative methyltransferase | S. cattleya | AEW99097.1 | F8JNE0 | ThnL |
| 6* | putative methyltransferase* | S. cattleya | AEW99093.1 | F8JNE4 | ThnP* |
| 6* | putative methyltransferase* | S. cattleya | AEW99098.1 | F8JND9 | ThnK* |

*alternative enzyme

As used herein, "glycolysis/Acetyl-CoA biosynthesis multi-enzyme" refers the group of enzymes selected from the group consisting of Glk, Pgi, PfkA, Fba, Tpi, GabP, Pgk, GpmA, Eno, PykA, PykF, AceE, AceF, and subsets thereof. Isozymes of any one of these enzymes are also encompassed within the scope of "glycolysis/Acetyl-CoA biosynthesis multi-enzyme." It is understood that this particular listing of enzymes is a non-limiting example of the group of enzymes useful in performing step (c). Other groups of enzymes may be found useful in performing this particular step and are contemplated as encompassed within the scope of "glycolysis/Acetyl-CoA biosynthesis multi-enzyme."

In certain embodiments, one or more enzymes are expressed and optionally sequestered in the cytoplasm of the cell prior to lysis. In certain embodiments, one or more enzymes are expressed and optionally sequestered in the periplasmic space. Exemplary enzymes listed in Tables 1 and 2 may be sequested in the cytoplasmic or periplasmic space upon expression, or may be sequestered elsewhere. In certain embodiments, at least one enzyme provided in Table 2 is sequestered in the periplasmic space. Sequestration of enzymes in the periplasmic space is known in the art, see, e.g., PCT Application No. PCT/US2011/035639, incorporated herein by reference. Upon lysing of a cell to provide a cell lysate, the sequestered enzymes are free to react with one or more substrates also present in the lysate or different lysate.

In certain embodiments, one or more enzymes provided in Table 1 are expressed and optionally sequestered in the cytoplasm. In certain embodiments, one or more enzymes selected from the group consisting of a kinase (e.g., a gamma-glutamyl kinase, e.g., from E. coli proline biosynthesis, ProB, or an isozyme thereof), a dehydrogenase (e.g., a Glu-5-P dehydrogenase, e.g., from E. coli proline biosynthesis, ProA, or an isozyme thereof); glycolysis/acetyl-CoA biosynthesis multi-enzyme (e.g., Glk, Pgi, PfkA, Fba, Tpi, GabP, Pgk, GpmA, Eno, PykA, PykF, AceE, and/or AceF, or an isozyme thereof); acetyl-CoA acetyltransferase (e.g., from *R. sphaeroides*, PhaA, or an isozyme thereof); beta-oxidation multienzyme (e.g., from *E. coli*, FadB, or an isozyme thereof); crotonyl-CoA reductase (e.g., from *R. sphaeroides*, Ccr, or an isozyme thereof); acetyl-CoA carboxylase (e.g., from *E. coli*, AccABCD, or an isozyme thereof); malonyl-CoA reductase enzyme (e.g., from *Sulfolobus tokodaii*, expressed in *E. coli*, Mcr, or an isozyme thereof); threonine aldolase (e.g., expressed in *E. coli*, LtaE, or an isozyme thereof); beta-alanine transferase enzymes; proline 3-hydroxylase enzymes (e.g., P3H1, or an isozyme thereof); proline oxidase enzyme (e.g., PutA or an isozyme thereof); and isozymes thereof, are expressed and optionally sequestered in the cytoplasm prior to lysis of the cell. In certain embodiments, the cell is lysed to provide a cell lysate.

In certain embodiments, one or more enzymes provided in Table 2 are expressed and optionally sequestered in the periplasmic space. In certain embodiments, one or more enzymes selected from the group consisting of carboxymethyl-Pro synthase (e.g., from *Pectobacterium carotovorum*, CarB, and/or from *Strepomyces cattleya*, then, or isozymes thereof); carbapenam synthetase (e.g., from *P. carotovorum*, CarA, or an isozyme thereof); beta-lactam synthetase (e.g., from *Strepomyces cattleya*, ThnM, or an isozyme thereof); carbapenem synthase (e.g., from *P. carotovorum*, CarC, and/or from *Strepomyces cattleya*, ThnG, or an isozyme thereof); transferase (e.g., from *Strepomyces cattleya*, ThnV, or an isozyme thereof); oxygenase (e.g., from *Strepomyces cattleya*, ThnQ, or an isozyme thereof; or an enzyme of the 2-oxoglutarate and/or Fe(II)-dependent oxygenase superfamily, or an isozyme thereof); and a methyltransferase enzyme (e.g., ThnL, ThnP, ThnK, or an isozyme thereof); and isozymes thereof, are expressed and optionally sequestered in the periplasmic space prior to cell lysis. For example, in certain embodiments, a carboxymethyl-Pro synthase (e.g., from *Pectobacterium carotovorum*, CarB, and/or from *Strepomyces cattleya*, ThnE), or isozyme thereof, is sequestered in the periplasmic space. In certain embodiments, a carbapenam synthetase (e.g., from *P. carotovorum*, CarA), or isozyme thereof, is sequestered in the periplasmic space. In certain embodiments, a beta-lactam synthetase (e.g., from *Strepomyces cattleya*, ThnM), or isozyme thereof, is sequestered in the periplasmic space. In certain embodiments, a carbapenem synthase (e.g., from *P. carotovorum*, CarC, and/or from *Strepomyces cattleya*, ThnG), or isozyme thereof, is sequestered in the periplasmic space. In certain embodiments, a transferase (e.g., from *Strepomyces cattleya*, ThnV, or isozyme thereof) is sequestered in the periplasmic space. In certain embodiments, an oxygenase (e.g., from *Strepomyces cattleya*, ThnQ; or an enzyme of the 2-oxoglutarate and/or Fe(II)-dependent oxygenase superfamily, or isozyme thereof) is sequestered in the periplasmic space. In certain embodiments, a methyltransferase enzyme (e.g., ThnL, ThnP, ThnK, or an isozyme thereof) is sequestered in the periplasmic space.

Methods associated with the invention encompass lysates from any type of cell, e.g., prokaryotic and eukaryotic cells. In some embodiments, the cell is a bacterial cell, such as *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp., and *Pantoea* spp. The bacterial cell can be a Gram-negative cell such as an *Escherichia coli* (*E. coli*) cell, or a Gram-positive cell such as a species of *Bacillus*. In other embodiments the cell is a fungal cell such as a yeast cell, e.g., *Saccharomyces* spp., *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp., *Yarrowia* spp. and industrial polyploid yeast strains. Other non-limiting examples of fungi include *Aspergillus* spp., *Pennicilium* spp., *Fusarium* spp., *Rhizopus* spp., *Acremonium* spp., *Neurospora* spp., *Sordaria* spp., *Magnaporthe* spp., *Allomyces* spp., *Ustilago* spp., *Botrytis* spp., *Pectobacterium* spp., and *Trichoderma* spp. In other embodiments, the cell is an algal cell, a plant cell, or a mammalian cell. It should be appreciated that some cells compatible with the invention may express an endogenous copy of one or more of the genes associated with the invention as well as a recombinant copy.

In certain embodiments, the cell lysate is a lysate of an *E. coli* cell engineered to overexpress one or more enzymes described herein. In certain embodiments, the cell lysate is a lysate of an *E. coli* cell engineered to overexpress a group of enzymes, e.g., two, three, four, five, six, seven, eight, nine, ten, eleven, twelve, thirteen, fourteen, fifteen, sixteen, seventeen, eighteen, nineteen, twenty, or more than twenty enzymes. In certain embodiments, the cell lysate is a combination of different cell lysates, e.g., a combination of two, three, four, five, six, seven, eight, nine, ten, or more than ten different cell lysates, obtained from two, three, four, five, six, seven, eight, nine, ten, or more than ten different cells, e.g., from different organisms, each engineered to overexpress one or more enzymes. In some embodiments, lysates from different organisms are combined. For example, a lysate from an engineered *E. coli* strain can be combined with a lysate from a different bacterial strain, such as a *Pectobacterium carotovorum* (source of CarABC genes) strain and/or a lysate from a *Streptomyces cattleya* (native thienamycin producer). In certain embodiments, different engineered *E. coli* strains (e.g., overexpressing different production pathway proteins) are combined to optimize enzyme levels prior to creating a single engineered strain with all overexpressed proteins.

Combinations of one or more different lysates comprising expression of different enzymes or expression of different combination of two or more enzymes as described above in Tables 1 and 2 is further contemplated. In certain embodiments, the cell lysate is a lysate of a cell engineered to overexpress one or more enzymes selected from the group consisting of a kinase (e.g., a gamma-glutamyl kinase), a dehydrogenase (e.g., a Glu-5-P dehydrogenase), glycolysis/acetyl-CoA biosynthesis multi-enzyme, an acetyl-CoA acetyltransferase, a beta-oxidation multienzyme, a crotonyl-CoA reductase, an acetyl-CoA carboxylase, a malonyl-CoA reductase, a threonine aldolase, a beta-alanine transferase, a proline 3-hydroxylase, a proline oxidase, a carboxymethyl-Pro synthase, a carbapenam synthetase, a beta-lactam synthetase, a carbapenem synthase, a transferase, an oxygenase, a methyltransferase, and isozymes thereof. In certain embodiments, one or more enzymes selected from the group consisting of a kinase (e.g., a gamma-glutamyl kinase), a dehydrogenase (e.g., a Glu-5-P dehydrogenase), glycolysis/acetyl-CoA biosynthesis multi-enzyme, an acetyl-CoA acetyltransferase, a beta-oxidation multienzyme, a crotonyl-CoA reductase, an acetyl-CoA carboxylase, a malonyl-CoA reductase, a threonine aldolase, a beta-alanine transferase, a proline 3-hydroxylase, a proline oxidase, and isozymes thereof, were present in the cell cytoplasm prior to lysing. In certain embodiments, one or more enzymes selected from the group consisting of a carboxymethyl-Pro synthase, a carbapenam synthetase, a beta-lactam synthetase, a carbapenem synthase, a transferase, an oxygenase, a methyltransferase, and isozymes thereof, are sequestered in the periplasmic space of the cell prior to lysing.

Cell-Free System for Generating Carbapenems

As generally described above, the present invention provides a process for generating a wide variety of carbapenems by utilizing cell-free conditions to generate a carbapenem which, optionally, may be further enzymatically and/or chemically manipulated, to provide a compound of Formula (I).

For example, in one aspect, provided is a cell lysate comprising a group of enzymes capable of generating a compound of the Formula (I-a):

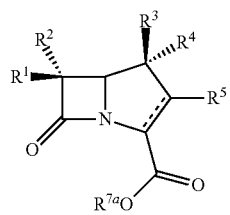

(I-a)

or a salt or tautomer thereof, or a combination thereof; from:
(1) glucose and glycine or salts thereof; and/or
(2) glucose and an optionally substituted glutamate of Formula (i):

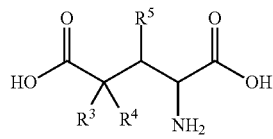

(i)

or salts thereof; and/or
(3) glucose and a proline compound of Formula (iv):

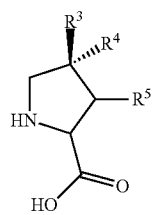

(iv)

wherein $R^{7a}$ is hydrogen; $R^5$ is selected from the group consisting of hydrogen, —$OR^8$, —$SR^8$, and —$N(R^8)_2$; ---- represents a single or double bond; and $R^1$, $R^2$, $R^3$, and $R^4$ are as defined herein.

In another aspect, provided is a method of generating a compound of Formula (I-a):

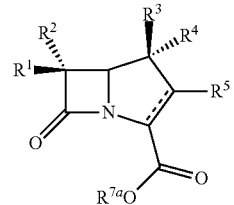

(I-a)

or a salt or tautomer thereof, or a combination thereof;
the method comprising:
providing a cell lysate comprising one or more enzymes, wherein the enzymes are selected from the group consisting of a kinase (e.g., a gamma-glutamyl kinase), a dehydrogenase (e.g., a Glu-5-P dehydrogenase); glycolysis/Acetyl-CoA biosynthesis multi-enzyme, an acetyl-CoA acetyltransferase, a beta-oxidation multienzyme, a crotonyl-CoA reductase, an acetyl-CoA carboxylase, a malonyl-CoA reductase, a threonine aldolase, a beta-alanine transferase, a proline 3-hydroxylase, a proline oxidase, a carboxymethyl-Pro synthase, a carbapenam synthetase, a beta-lactam synthetase, a carbapenem synthase, a transferase, an oxygenase, a methyltransferase, and isozymes thereof;
wherein the one or more cell lysates were contacted with:
(1) glucose and glycine or salts thereof; and/or
(2) glucose and an optionally substituted glutamate of the Formula (i):

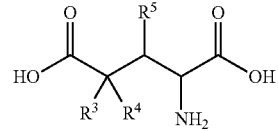

(i)

or salts thereof, and/or
(3) glucose and a proline compound of Formula (iv):

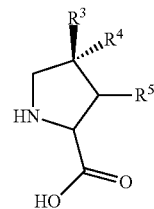

(iv)

and salts thereof; wherein $R^{7a}$ is hydrogen; $R^5$ is selected from the group consisting of hydrogen, —$OR^8$, —$SR^8$, and —$N(R^8)_2$; and ----, $R^1$, $R^2$, $R^3$, and $R^4$ are as defined herein.

In certain embodiments, the one or more enzymes selected from the group consisting of a kinase (e.g., a gamma-glutamyl kinase), a dehydrogenase (e.g., a Glu-5-P dehydrogenase), glycolysis/acetyl-CoA biosynthesis multienzyme, an acetyl-CoA acetyltransferase, a beta-oxidation multienzyme, a crotonyl-CoA reductase, an Acetyl-CoA carboxylase, a malonyl-CoA reductase, a threonine aldolase, a beta-alanine transferase, a proline 3-hydroxylase, a proline oxidase, and isozymes thereof, are present in cell cytoplasm of the cell prior to lysing. In certain embodiments, the one or more enzymes selected from the group consisting of a carboxymethyl-Pro synthase, a carbapenam synthetase, a beta-lactam synthetase, a carbapenem synthase, a transferase, an oxygenase, a methyltransferase, and isozymes thereof, are sequestered in the periplasmic space prior to lysing. In certain embodiments, the one or more cells were genetically engineered to express any one of the above listed one or more enzymes. In certain embodiments, any one of the above listed one or more enzymes are overexpressed, i.e., expressed at a level of concentration exceeding that found in an unengineered, wild type cell.

In certain embodiments, the glucose and glycine are enzymatically converted to an optionally substituted glutamate semialdehyde of Formula (ii):

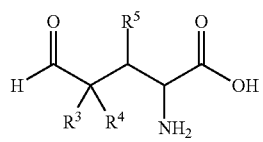

(ii)

or salt thereof (e.g., 3-hydroxy-glutamate semialdehyde) upon contact with one or more enzymes selected from the group consisting of glycolysis/acetyl-CoA biosynthesis multienzyme, acetyl-CoA carboxylase, malonyl-CoA reductase, threonine aldolase, a kinase (e.g., a gamma-glutamyl kinase), a dehydrogenase (e.g., a Glu-5-P dehydrogenase), and isozymes thereof. In certain embodiments, each enzyme selected from the group consisting of glycolysis/acetyl-CoA biosynthesis multienzyme, acetyl-CoA carboxylase, malonyl-CoA reductase, threonine aldolase, a kinase (e.g., a gamma-glutamyl kinase), and a dehydrogenase (e.g., a Glu-5-P dehydrogenase) is expressed.

Figure 3:
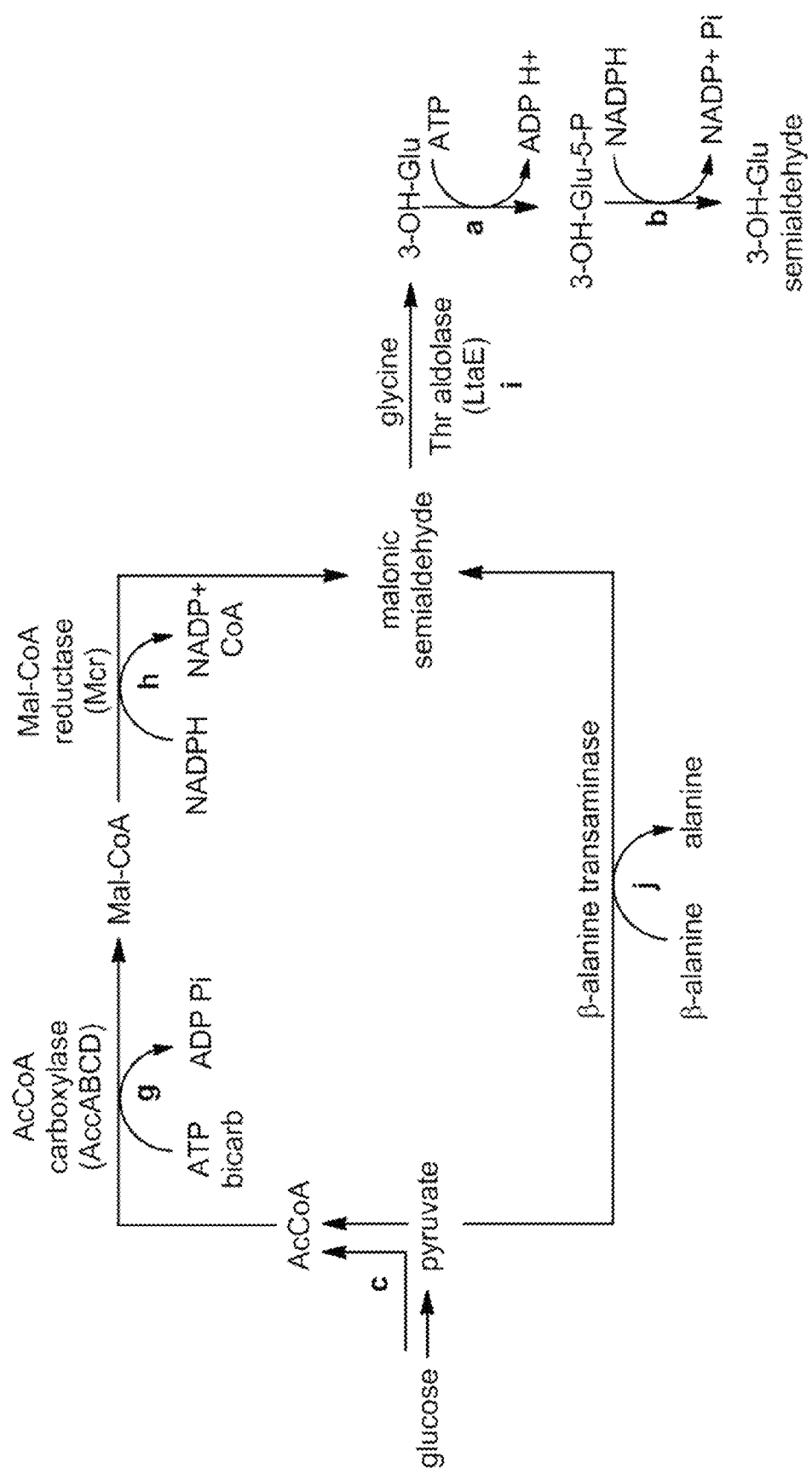
FIG. 3 depicts two alternative routes for the enzymatic production of 3-hydroxy-glutamate semialdehyde (steps a, b, c, g, h, i, and/or j).

Alternatively, glucose and glycine are enzymatically converted to an optionally substituted glutamate semialdehyde of Formula (ii) (e.g., 3-hydroxy-glutamate semialdehyde) upon contact with one or more enzymes selected from the group consisting of glycolysis/acetyl-CoA biosynthesis multienzyme, beta-alanine transaminase, threonine aldolase, a kinase (a gamma-glutamyl kinase), a dehydrogenase (a Glu-5-P dehydrogenase), and isozymes thereof. See, e.g., FIG. 3.

In certain embodiments, the optionally substituted glutamate semialdehyde compound of Formula (ii):

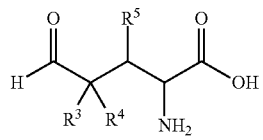

(ii)

or salt thereof, cyclizes to form a pyrrole compound of formula (v):

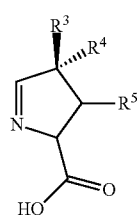

(v)

or salt thereof. Water is a byproduct of this reaction. In certain embodiments, the reaction is carried out without enzymatic catalysis.

In certain embodiments, the proline compound of Formula (iv):

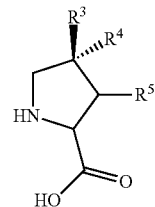

(iv)

or salt thereof, is enzymatically converted to a pyrrole compound of formula (v):

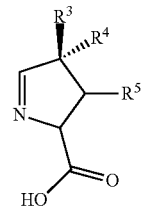

(v)

or salt thereof; upon contact with a proline oxidase.

In certain embodiments, the proline compound of Formula (iv):

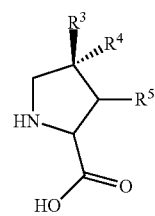

(iv)

or salt thereof, wherein $R^5$ is hydrogen, is enzymatically converted to a 3-hydroxylated proline compound of formula:

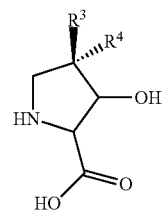

(iv-a)

or salt thereof; upon contact with a proline-3-hydroxylase.

In certain embodiments, the 3-hydroxylated proline compound of formula:

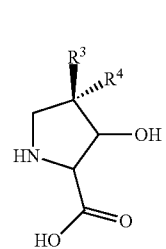

(iv-a)

or salt thereof, is enzymatically converted to a 3-hydroxylated pyrrole compound of formula:

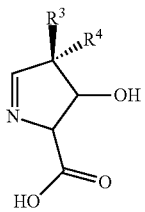

(v-a)

or salt thereof, upon contact with a proline oxidase.

In certain embodiments, the proline compound is selected from the group consisting of proline, 3-hydroxyproline, 4-methylproline, 3-hydroxy-4-methylproline, and salts thereof. In certain embodiments, the pyrrole compound is selected from the group consisting of 3,4-dihydro-2H-pyrrole-2-carboxylic acid, 3-hydroxy-3,4-dihydro-2H-pyrrole-2-carboxylic acid, 4-methyl-3,4-dihydro-2H-pyrrole-2-carboxylic acid, 3-hydroxy-4-methyl-3,4-dihydro-2H-pyrrole-2-carboxylic acid, and salts thereof. In certain embodiments, the proline compound and pyrrole compound are both L isomers.

In certain embodiments, the optionally substituted glutamate of Formula (i):

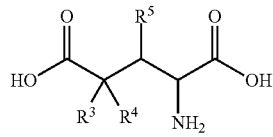

(i)

or salt thereof, is enzymatically converted to a proline compound of Formula (iv):

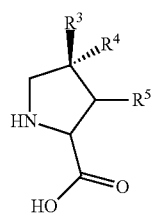

(iv)

or salt thereof; upon contact with the γ-glutamyl kinase-GP-reductase multienzyme complex (e.g., *E. coli* ProB and ProA).

In certain embodiments, glucose is enzymatically converted to an optionally substituted CoA compound of Formula (iii):

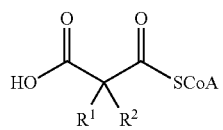

Figure 4:
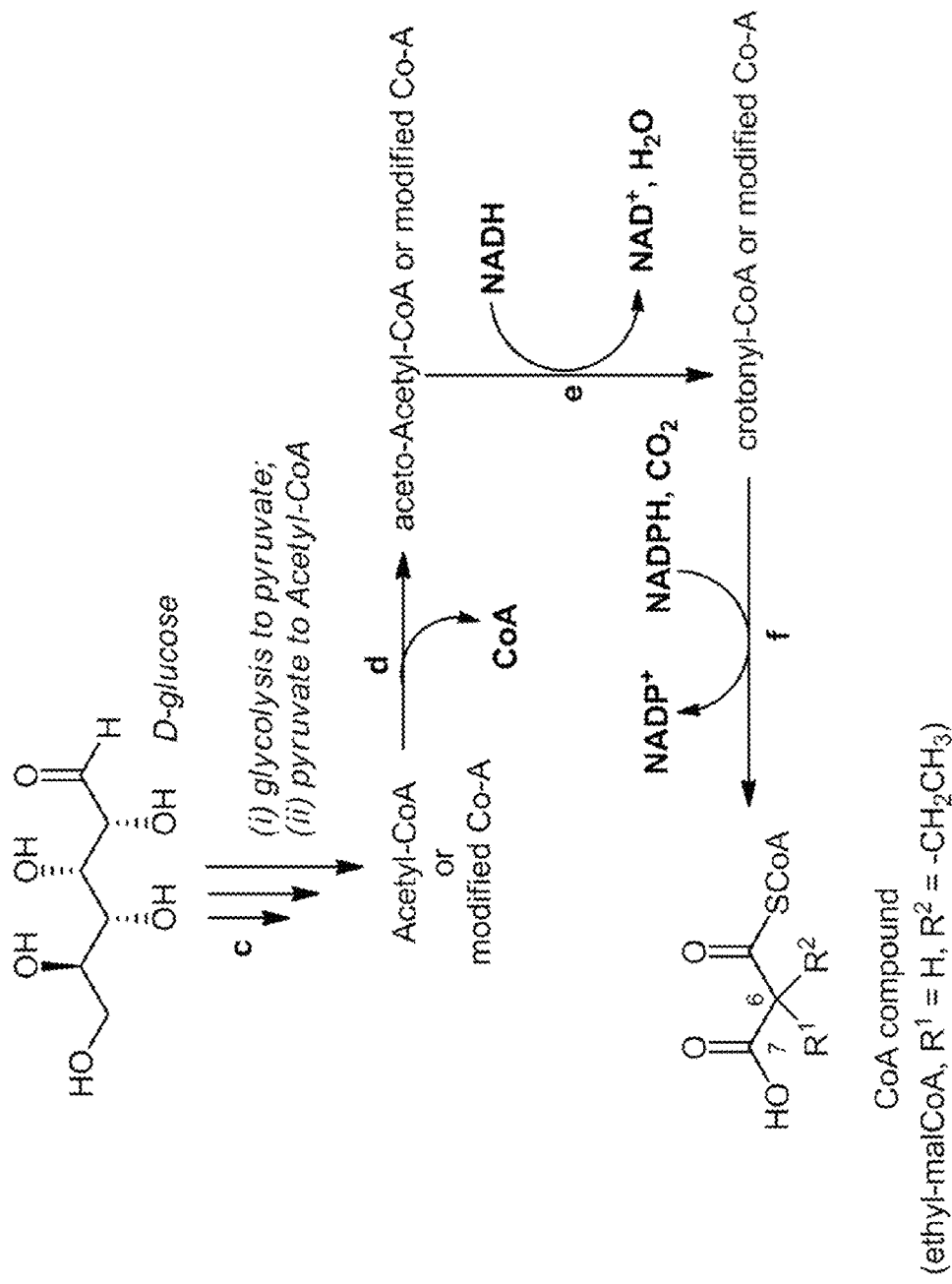
FIG. 4 depicts the enzymatic production of optionally substituted CoA compound from glucose (steps c-f).
Figure 5A:
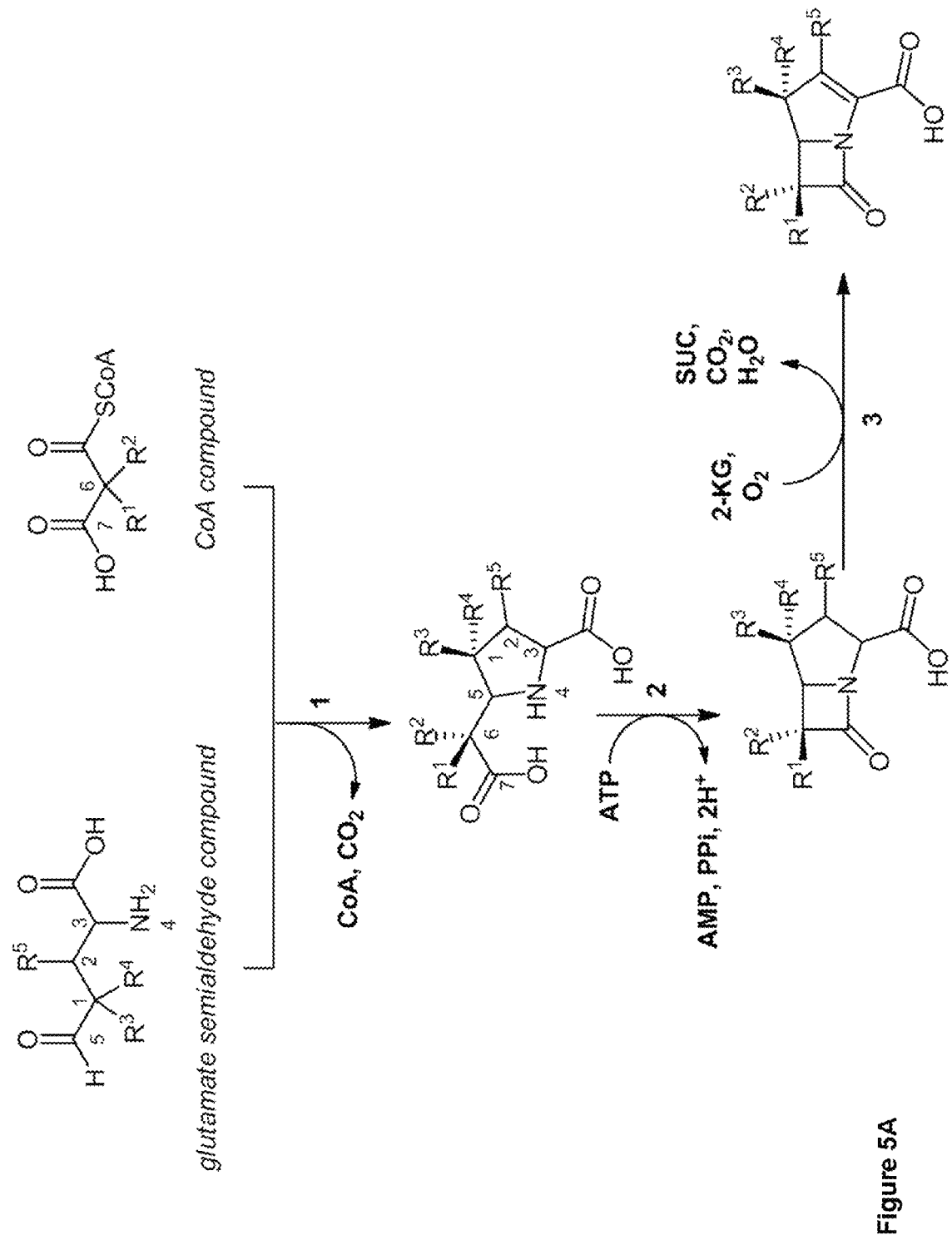
FIGS. 5A and 5B depict the enzymatic production of a carbapenem from a glutmate semialdehyde compound and a coenzyme A (CoA) compound. The process utilizes enzymes from both thienamycin and/or carbapenem biosynthetic pathways (steps 1-3). The *E. coli* may be engineered to produce the key-entry enzyme carboxymethyl-Pro synthase (CarB, ThnE, or isozyme thereof) in the periplasmic space of the *E. coli*.
Figure 5B:
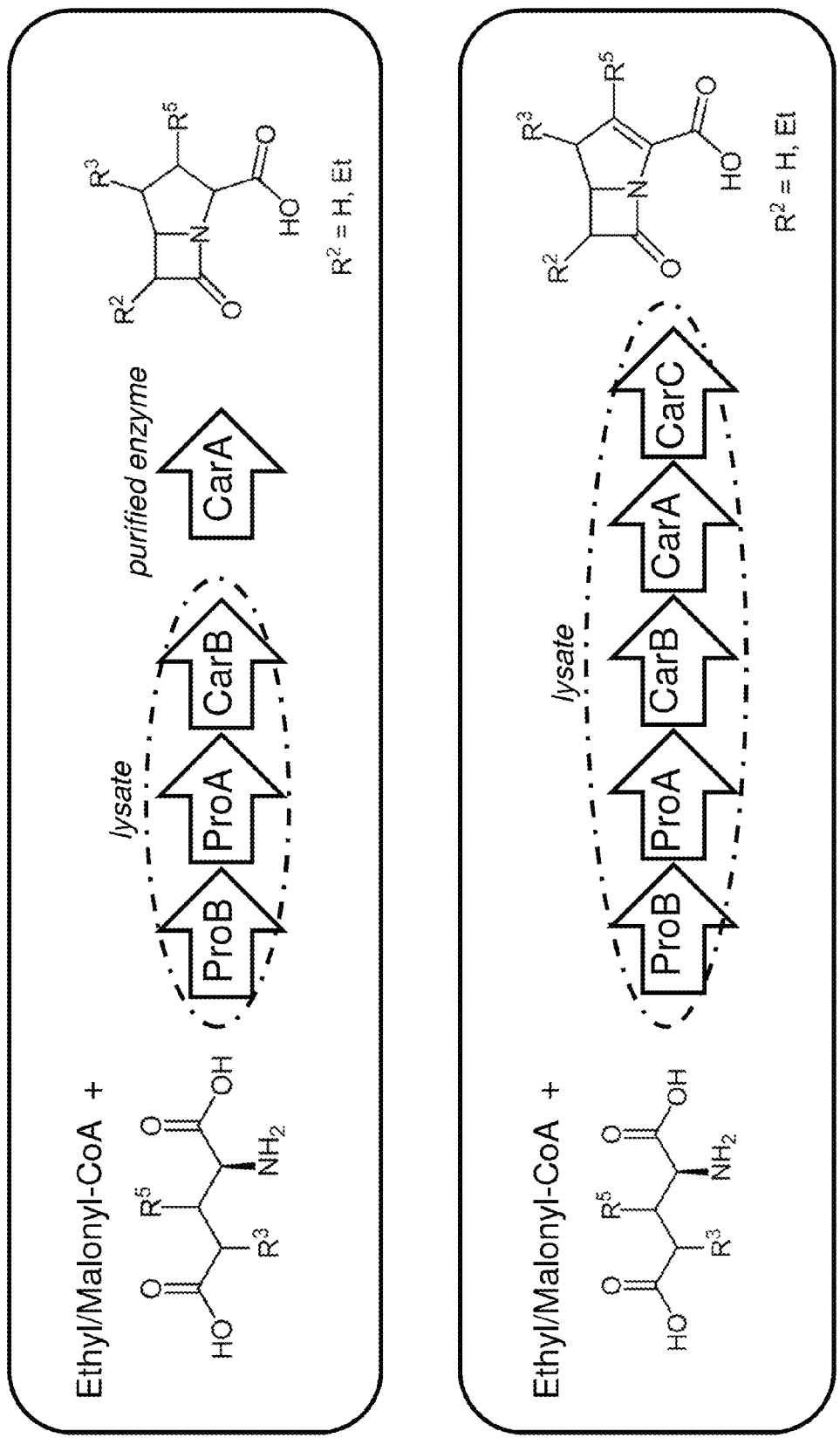

(iii)

or salt thereof; wherein —SCoA is Coenzyme A monoradical (—SC$_{21}$H$_{35}$N$_7$O$_{16}$P$_3$). See, e.g., FIG. 4. In certain embodiments, the glucose is converted to an optionally substituted CoA compound of Formula (iii) upon contact with one or more enzymes selected from the group consisting of a glycolysis/Acetyl-CoA biosynthesis multi-enzyme, Acetyl-CoA acetyltransferase, beta-oxidation multienzyme, Crotonyl-CoA reductase, and isozymes thereof.

In certain embodiments, the optionally substituted glutamate of Formula (i):

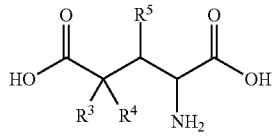

(i)

or salt thereof, is enzymatically converted to an optionally substituted glutamate semialdehyde of Formula (ii):

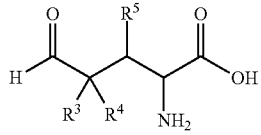

Figure 2A:
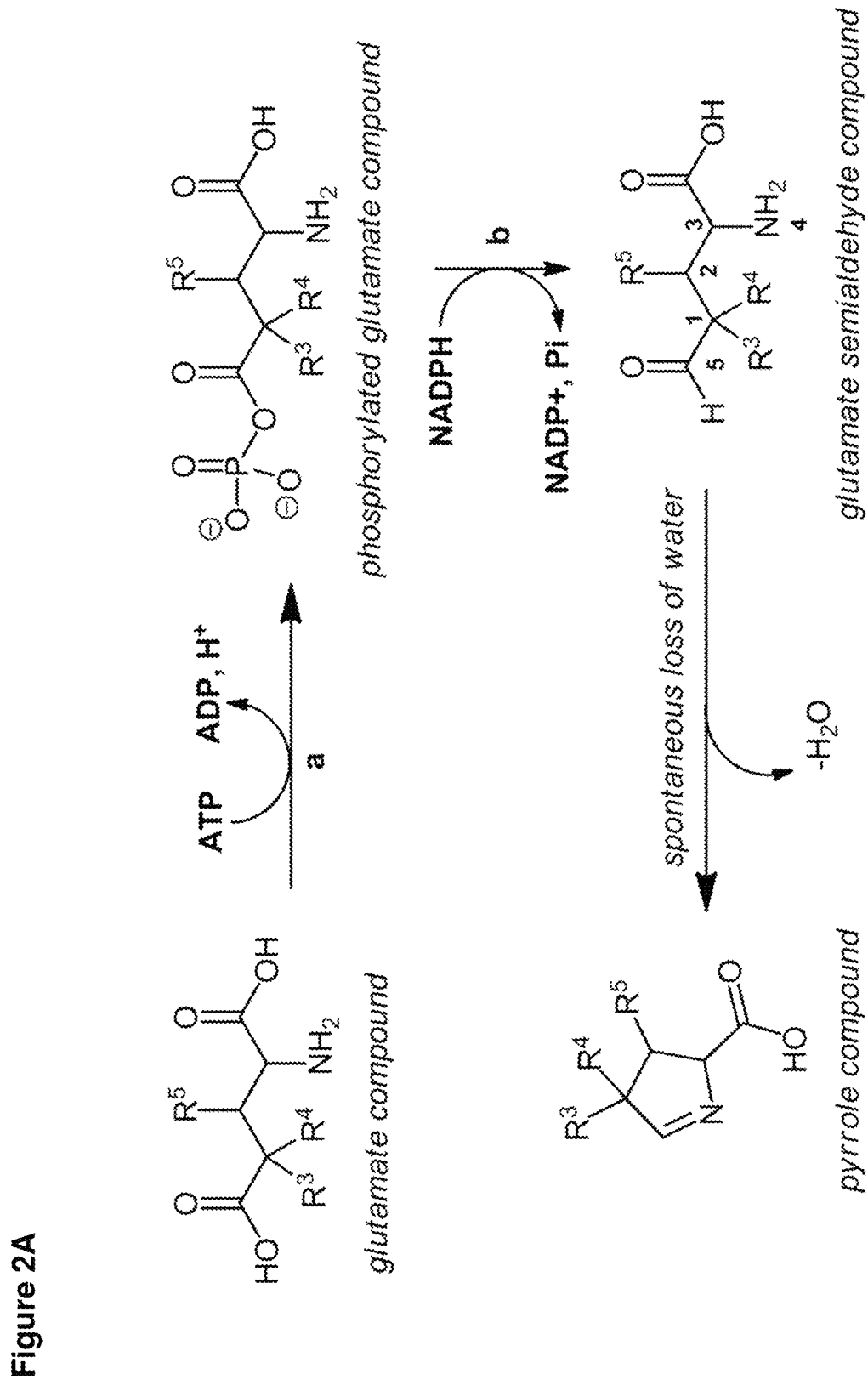
FIG. 2A depicts the proposed enzymatic production of an optionally substituted glutamate semialdehyde (a "glutamate semialdehyde compound") from an optionally substituted glutamate (a "glutamate compound") (steps a-b, Table 1). The glutamate semialdehyde compound may spontaneously cyclize to form a pyrrole compound in situ.
Figure 2B:
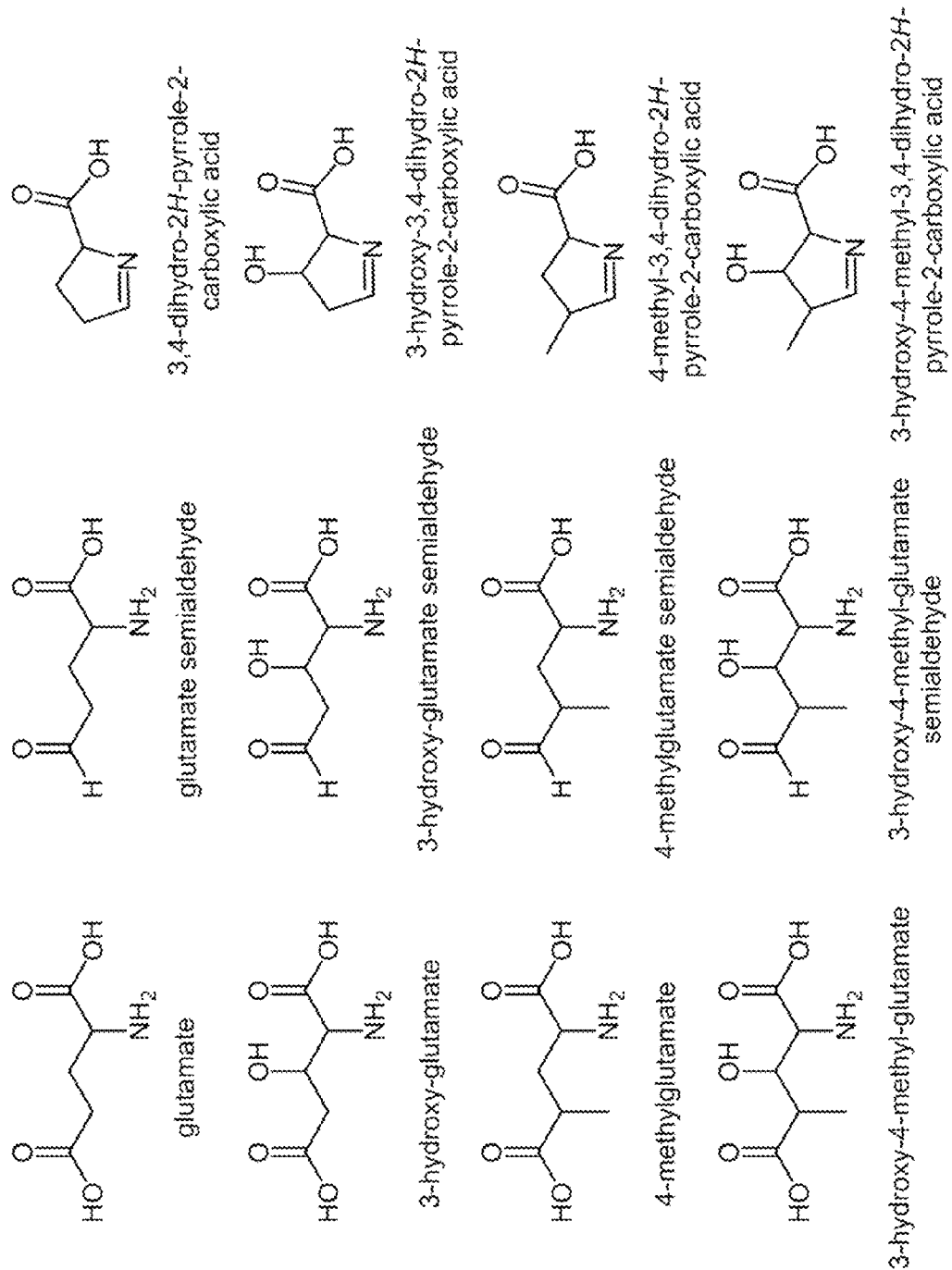
FIG. 2B depicts exemplary glutamate semialdehyde compounds and pyrrole compounds which may be produced following the method depicted in FIG. 2A.

(ii)

or salt thereof. In certain embodiments, the optionally substituted glutamate of Formula (i) is enzymatically converted to an optionally substituted glutamate semialdehyde of Formula (ii) upon contact with one or more enzymes selected from the group consisting of a kinase (e.g., a gamma-glutamyl kinase) and a dehydrogenase (e.g., a Glu-5-P dehydrogenase); see, e.g., FIG. 2A. In certain embodiments, the optionally substituted glutamate of Formula (i) is selected from the group consisting of glutamate, 3-hydroxyglutamate, 4-methylglutamate, and 3-hydroxy-4-methylglutamate, and the corresponding optionally substituted glutamate semialdehyde of Formula (ii) is selected from the group consisting of glutamate semialdehyde, 3-hydroxyglutamate semialdehyde, 4-methylglutamate semialdehyde, and 3-hydroxy-4-methyl-glutamate semialdehyde; see, e.g., FIG. 2B. In certain embodiments, the glutamate compound and glutamate semialdehyde are both L isomers.

In certain embodiments, the cell lysate converts the combination of glucose and glycine, or salts thereof, or the combination of glucose and an optionally substituted glutamate of the Formula (i), or salts thereof, to an optionally substituted CoA compound of Formula (iii) and an optionally substituted glutamate semialdehyde of Formula (ii):

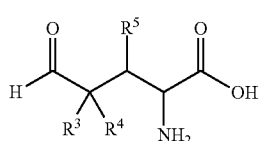

(ii)

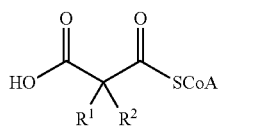

(iii)

or salts thereof. In certain embodiments, compounds of Formula (iii) and Formula (ii), or salts thereof, are converted to a compound of Formula (I-a) or salt thereof, e.g., upon contact with one or more enzymes released from the periplasmic space.

In certain embodiments, the optionally substituted glutamate semialdehyde of Formula (ii) and the optionally substituted CoA compound of Formula (iii) generate a pyrrolidinyl compound of Formula (II-a):

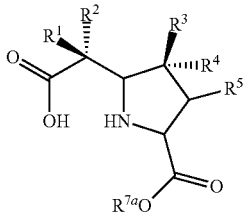

(II-a)

or salt thereof, wherein $R^{7a}$ is hydrogen, upon contact with an enzyme, optionally released from the periplasmic space.

In certain embodiments, the optionally substituted glutamate semialdehyde of Formula (ii) and the optionally substituted CoA compound of Formula (iii) generate a pyrrolidinyl compound of Formula (II-a):

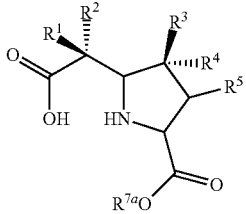

(II-a)

or salt thereof, wherein $R^{7a}$ is hydrogen, upon contact with an enzyme, optionally released from the periplasmic space.

In certain embodiments, the enzyme-containing cell lysate converts the combination of glucose and the proline compound of Formula (iv) to an optionally substituted CoA compound of Formula (iii), or salt thereof, and an pyrrole compound of Formula (v), or salt thereof:

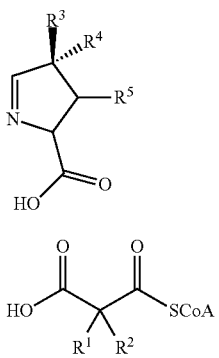

wherein —SCoA is Coenzyme A monoradical.

In certain embodiments, the pyrrole compound of Formula (v), or salt thereof, and the optionally substituted CoA compound of Formula (iii) generate a pyrrolidinyl compound of Formula (II-a):

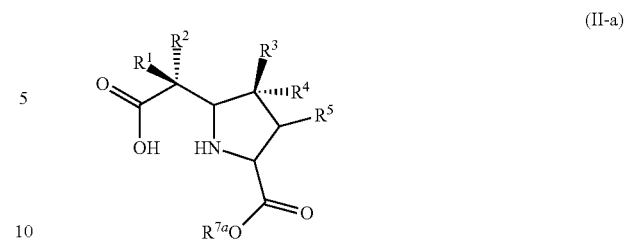

(II-a)

or salt thereof, wherein $R^{7a}$ is hydrogen, upon contact with an enzyme, optionally released from the periplasmic space.

In certain embodiments, ---- represents a single bond. In certain embodiments, ---- represents a double bond.

In certain embodiments, $R^1$ is hydrogen. In certain embodiments, $R^1$ is optionally substituted alkyl. In certain embodiments, $R^1$ is optionally substituted $C_{1-6}$alkyl. In certain embodiments, $R^1$ is optionally substituted $C_{1-4}$ alkyl. In certain embodiments, $R^1$ is optionally substituted $C_{1-3}$alkyl. In certain embodiments, $R^1$ is optionally substituted $C_{1-2}$alkyl. In certain embodiments, $R^1$ is —$CH_3$. In certain embodiments, $R^1$ is selected from hydrogen and —$CH_3$.

In certain embodiments, $R^2$ is hydrogen, optionally substituted alkyl, optionally substituted alkenyl, optionally substituted alkynyl, or optionally substituted heteroalkyl. In certain embodiments, $R^2$ is hydrogen, optionally substituted alkyl, or optionally substituted heteroalkyl. In certain embodiments, $R^2$ is hydrogen or optionally substituted alkyl. In certain embodiments, $R^2$ is hydrogen. In certain embodiments, $R^2$ is optionally substituted alkyl. In certain embodiments, $R^2$ is optionally substituted $C_{1-6}$alkyl. In certain embodiments, $R^2$ is optionally substituted $C_1$ alkyl. In certain embodiments, $R^2$ is optionally substituted $C_{1-3}$alkyl. In certain embodiments, $R^2$ is optionally substituted $C_{1-2}$alkyl. In certain embodiments $R^2$ is optionally substituted $C_1$ alkyl. In certain embodiments, $R^2$ is —$CH_3$. In certain embodiments, $R^2$ is selected from hydrogen, —$CH_3$, —$CH_2OH$, —$CH_2CH_3$, —$CH(CH_3)_2$, or —$CH(OH)CH_3$.

In certain embodiments, $R^1$ is hydrogen, and $R^2$ is hydrogen or optionally substituted alkyl. In certain embodiments, $R^1$ is hydrogen, and $R^2$ is hydrogen or optionally substituted $C_{1-6}$ alkyl (e.g., —$CH_3$, —$CH_2OH$, —$CH_2CH_3$, —$CH(CH_3)_2$, or —$CH(OH)CH_3$). In certain embodiments, $R^1$ is hydrogen, and $R^2$ is hydrogen. In certain embodiments, $R^1$ is hydrogen, and $R^2$ is —$CH_3$, —$CH_2OH$, —$CH_2CH_3$, —$CH(CH_3)_2$, or —$CH(OH)CH_3$. In certain embodiments, $R^1$ is hydrogen, and $R^2$ is —$CH_3$ or —$CH_2CH_3$. In certain embodiments, $R^1$ is hydrogen, and $R^2$ is —$CH(OH)CH_3$.

In certain embodiments, $R^3$ is hydrogen, optionally substituted alkyl, optionally substituted alkenyl, optionally substituted alkynyl, or optionally substituted heteroalkyl. In certain embodiments, $R^3$ is hydrogen, optionally substituted alkyl, or optionally substituted heteroalkyl. In certain embodiments, $R^3$ is hydrogen or optionally substituted alkyl. In certain embodiments, $R^3$ is hydrogen. In certain embodiments, $R^3$ is optionally substituted alkyl. In certain embodiments, $R^3$ is optionally substituted $C_{1-6}$alkyl. In certain embodiments, $R^3$ is optionally substituted $C_{1-4}$alkyl. In certain embodiments, $R^3$ is optionally substituted $C_{1-3}$alkyl. In certain embodiments, $R^3$ is optionally substituted $C_{1-2}$alkyl. In certain embodiments $R^3$ is —$CH_3$. In certain embodiments, $R^3$ is hydrogen or —$CH_3$.

In certain embodiments, $R^4$ is hydrogen. In certain embodiments, $R^4$ is optionally substituted alkyl. In certain embodiments, $R^4$ is optionally substituted $C_{1-6}$alkyl. In certain embodiments, $R^4$ is optionally substituted $C_{1-4}$alkyl. In certain embodiments, $R^4$ is optionally substituted $C_{1-3}$alkyl. In certain embodiments, $R^4$ is optionally substituted $C_{1-2}$alkyl. In certain embodiments, $R^4$ is —$CH_3$. In certain embodiments, $R^4$ is selected from hydrogen and —$CH_3$.

In certain embodiments, $R^4$ is hydrogen, and $R^3$ is hydrogen. In certain embodiments, $R^4$ is hydrogen, and $R^3$ is optionally substituted alkyl. In certain embodiments, $R^4$ is hydrogen, and $R^3$ is optionally substituted $C_{1-6}$alkyl (e.g., —$CH_3$, —$CH_2CH_3$, —$CH(CH_3)_2$). In certain embodiments, $R^4$ is hydrogen, and $R^3$ is —$CH_3$.

In certain embodiments, $R^5$ is hydrogen. In certain embodiments, $R^5$ is —$OR^8$, wherein $R^8$ is as defined herein. In certain embodiments, $R^5$ is —OH. In certain embodiments, $R^5$ is —$SR^8$, wherein $R^8$ is as defined herein. In certain embodiments, $R^5$ is —SH. In certain embodiments, $R^5$ is —$N(R^8)_2$, wherein $R^8$ is as defined herein. In certain embodiments, $R^5$ is —$NHR^8$. In certain embodiments, $R^5$ is —$NH_2$. In certain embodiments, $R^5$ is hydrogen or —OH.

In certain embodiments, $R^1$ is hydrogen; $R^2$ is hydrogen, —$CH_2$, or —$CH_2CH_3$; $R^3$ is hydrogen or —$CH_3$; $R^4$ is hydrogen; and $R^5$ is hydrogen or —OH.

For example, in certain embodiments when $R^1$ and $R^4$ are hydrogen, the compound of Formula (I-a) is of the Formula (I-b):

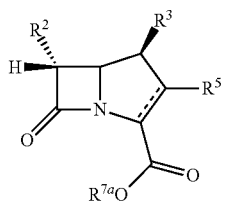

(I-b)

or a salt or tautomer thereof, or a combination thereof;

the optionally substituted glutamate of Formula (i) is of the Formula (i-a):

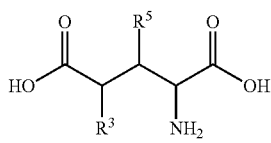

(i-a)

or salt thereof;

the optionally substituted glutamate semialdehyde is of Formula (ii-a):

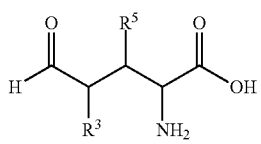

(ii-a)

or salt thereof;

the optionally substituted CoA compound is of Formula (iii-a):

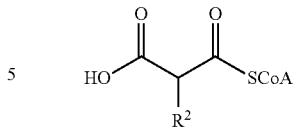

(iii-a)

or salt thereof;

the proline compound is of Formula (iv-aa):

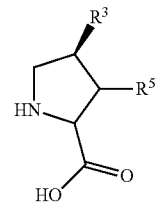

(iv-aa)

or salt thereof;

and the pyrrole compound is of Formula (v-aa):

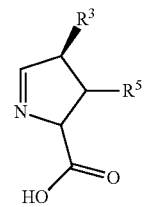

(v-aa)

or salt thereof; wherein $R^{7a}$ is hydrogen, and $R^2$, $R^3$, and $R^5$ are as defined herein.

As generally described above, in certain embodiments, the cell lysate converts the combination of glucose and glycine, or the combination of glucose and an optionally substituted glutamate of the Formula (i), to an optionally substituted CoA compound of Formula (iii) and an optionally substituted glutamate semialdehyde of Formula (ii). In certain embodiments, the optionally substituted glutamate semialdehyde of Formula (ii) and the optionally substituted CoA compound of Formula (iii) generate a pyrrolidinyl compound of Formula (II-a):

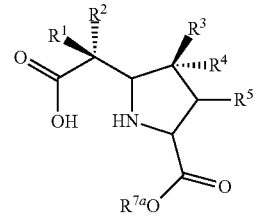

(II-a)

or salt thereof, upon contact with a carboxymethyl-Pro synthase (e.g., CarB, then) or isozyme thereof. In certain embodiments, $R^1$ is hydrogen. In certain embodiments, $R^2$ is hydrogen, —$CH_2$, or —$CH_2CH_3$. In certain embodiments, $R^3$ is hydrogen or —$CH_3$. In certain embodiments, $R^4$ is hydrogen. In certain embodiments, $R^5$ is hydrogen or —OH.

As generally described above, in other embodiments, the cell lysate converts the combination of glucose and an optionally substituted proline of the Formula (iv) to an optionally substituted CoA compound of Formula (iii) and an pyrrole compound of Formula (v). In certain embodiments, the optionally substituted CoA compound of Formula (iii) and an pyrrole compound of Formula (v) generate a pyrrolidinyl compound of Formula (II-a):

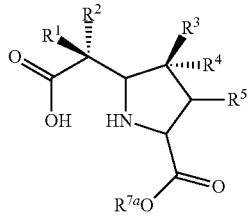

(II-a)

or salt thereof, upon contact with a carboxymethyl-Pro synthase (e.g., CarB, ThnE) or isozyme thereof. In certain embodiments, $R^1$ is hydrogen. In certain embodiments, $R^2$ is hydrogen, —$CH_2$, or —$CH_2CH_3$. In certain embodiments, $R^3$ is hydrogen or —$CH_3$. In certain embodiments, $R^4$ is hydrogen. In certain embodiments, $R^5$ is hydrogen or —OH.

In certain embodiments, wherein $R^1$ and $R^4$ are hydrogen, the pyrrolidinyl compound (II-a) is of the Formula (II-b):

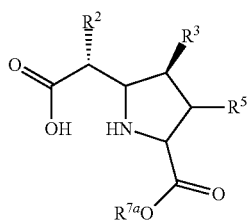

(II-b)

or salt thereof.

In certain further embodiments, the pyrrolidinyl compound (II-a) generates a β-lactam compound of Formula (III-a):

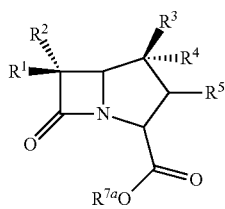

(III-a)

or salt thereof, upon contact with a carbapenam synthetase (e.g., CarA, or isozyme thereof) or a beta-lactam synthetase (e.g., ThnM, or isozyme thereof), or an isozyme thereof. In certain embodiments, $R^1$ is hydrogen. In certain embodiments, $R^2$ is hydrogen, —$CH_2$, or —$CH_2CH_3$. In certain embodiments, $R^3$ is hydrogen or —$CH_3$. In certain embodiments, $R^4$ is hydrogen. In certain embodiments, $R^5$ is hydrogen or —OH.

In certain embodiments, wherein $R^1$ and $R^4$ are hydrogen, the compound of Formula (III-a) is of the Formula (III-b):

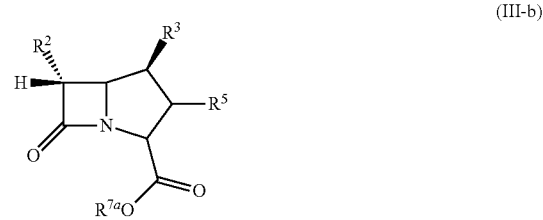

(III-b)

or salt thereof.

In certain further embodiments, the β-lactam compound of Formula (III-a) generates a compound of Formula (I-a):

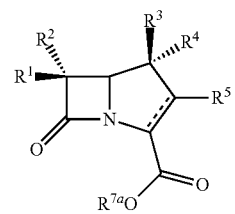

(I-a)

or salt thereof, wherein ---- is a double bond, upon contact with a carbapenem synthase (e.g., CarC or ThnG), or isozyme thereof. In certain embodiments, $R^1$ is hydrogen. In certain embodiments, $R^2$ is hydrogen, —$CH_2$, or —$CH_2CH_3$. In certain embodiments, $R^3$ is hydrogen or —$CH_3$. In certain embodiments, $R^4$ is hydrogen. In certain embodiments, $R^5$ is hydrogen or —OH.

In certain embodiments, the method further comprises one or more additional enzymatic and/or chemical steps to provide functionalized carbapenems encompassed by Formula (I). For example, it is contemplated that one or more positions on the carbapenem scaffold of Formula (I-a) may be further functionalized using enzymatic and/or chemical methods. In certain embodiments, the one or more of the contemplated additional enzymatic steps may be performed utilizing a cell-free system. For example, the cell, prior to lysing, may comprise the expression of one or more additional enzymes which are useful in further functionalization of the carbapenem scaffold in the cell-free reaction.

Attachment of the C2 Side Chain

In certain embodiments, the C2 side chain is installed on the carbapenem scaffold by enzymatic methods. For example, in certain embodiments, wherein $R^5$ is hydrogen, the method further comprises contacting the compound of Formula (I-a):

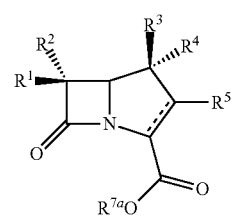

(I-a)

or a salt thereof; wherein ---- represents a double bond, with a transferase enzyme and a compound of the formula:

HS—$R^8$ wherein R⁸ is selected from the group consisting of optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, and optionally substituted heteroaryl;

to provide a thiol-containing compound of Formula (I-c):

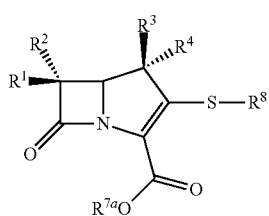

(I-c)

or salt thereof. In certain embodiments, R¹ is hydrogen. In certain embodiments, R² is hydrogen, —CH₂, or —CH₂CH₃. In certain embodiments, R³ is hydrogen or —CH₃. In certain embodiments, R⁴ is hydrogen.

In certain embodiments, wherein R¹ and R⁴ are hydrogen, the thiol-containing compound of Formula (I-c) is a compound of the Formula (I-d):

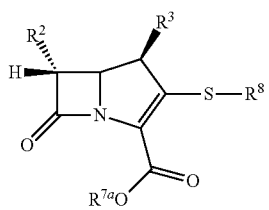

(I-d)

or salt thereof.

In certain embodiments, the transferase enzyme is an enzyme which is expressed by the cell. In certain embodiments, the transferase enzyme is an enzyme which is expressed by the cell and sequestered in the periplasmic space. Upon lysing the cell, the enzyme, in combination with a compound of the formula HS—R⁸, is free to react with the compound of Formula (I-a). However, in certain embodiments, the transferase enzyme is not expressed by the cell and sequestered in the periplasmic space. In certain embodiments, both the transferase enzyme and the HS—R⁸ are contacted with the compound of Formula (I-a) after lysing the cell, e.g., after the cell-free production of said compound. In certain embodiments, the transferase enzyme is an enzyme described in Nunez et al. *Chemistry and Biology* (2003) 10:301 (see, e.g., Table 1 of Nunez, incorporated herein by reference). In certain embodiments, the transferase enzyme is an *S. cattleya* transferase enzyme. In certain embodiments, the *S. cattleya* transferase enzyme is selected from the group consisting of ThnV, ThnE, ThnF, ThnH, ThnR, ThnT, ThnI, ThnU, ThnG, ThnQ, ThnK, ThnL, ThnP, ThnN, and isozymes thereof. In certain embodiments, the *S. cattleya* transferase enzyme is ThnV.

In certain embodiments, R⁸ is optionally substituted alkyl, optionally substituted heteroalkyl, or optionally substituted heterocyclyl.

In certain embodiments, R⁸ is optionally substituted alkyl. In certain embodiments, R⁸ is optionally substituted $C_{1-6}$alkyl. In certain embodiments, R⁸ is optionally substituted $C_{1-4}$alkyl. In certain embodiments, R⁸ is optionally substituted $C_{1-3}$alkyl. In certain embodiments, R⁸ is optionally substituted $C_{1-2}$alkyl.

In certain embodiments, R⁸ is optionally substituted heteroalkyl. In certain embodiments, R⁸ is optionally substituted hetero$C_{1-6}$alkyl. In certain embodiments, R⁸ is optionally substituted hetero$C_{1-4}$alkyl. In certain embodiments, R⁸ is optionally substituted hetero$C_{1-3}$alkyl. In certain embodiments, R⁸ is optionally substituted hetero$C_{1-2}$alkyl.

In certain embodiments, R⁸ is optionally substituted heterocyclyl. In certain embodiments, R⁸ is optionally substituted 5-6 membered heterocyclyl. In certain embodiments, R⁸ is optionally substituted 5-membered heterocyclyl (e.g., pyrrolidinyl, pyrazolidinyl). In certain embodiments, R⁸ is optionally substituted bicyclic heterocyclyl (e.g., pyrrolo[1,2-c]imidazolyl).

Exemplary R⁸ groups include, but are not limited to,

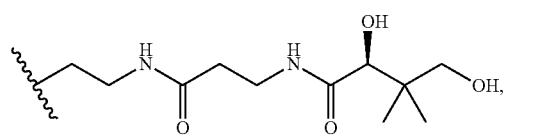
(a)

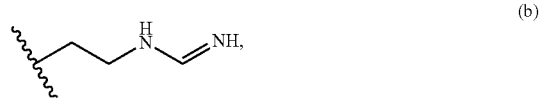
(b)

(c)

(d)

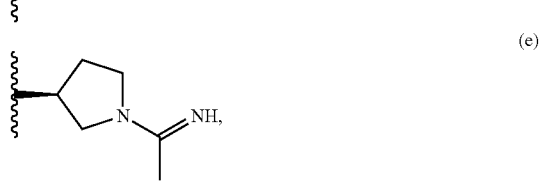
(e)

(f)

(g)

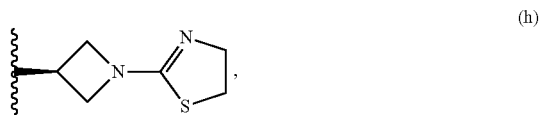
(h)

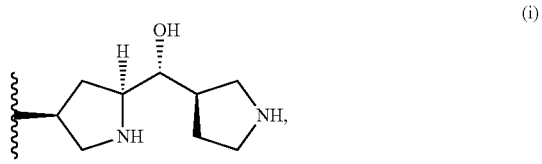
(i)

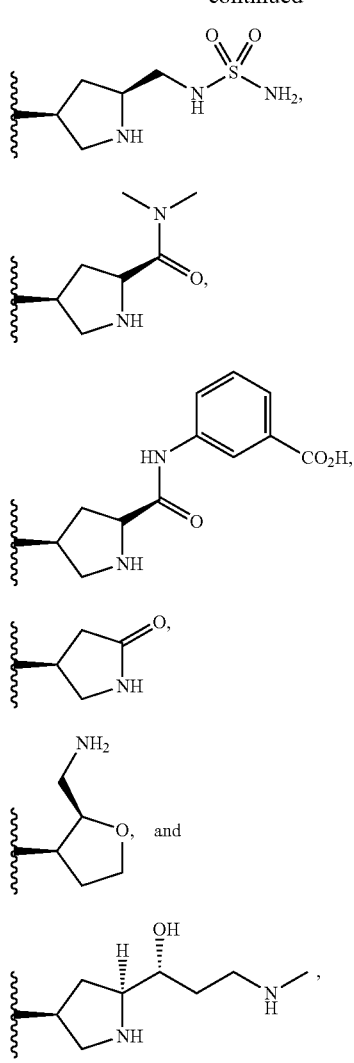

wherein X is a counterion.

In certain embodiments, R⁸ is a group of the Formula (a), (b), or (c). In certain embodiments, R⁸ is a group of the Formula (a). In certain embodiments, R⁸ is a group of the Formula (b). In certain embodiments, R⁸ is a group of the Formula (c).

Alternatively, in certain embodiments, the C2 side chain is installed by chemical methods. For example, in certain embodiments, wherein R⁵ is —OH, the method comprises contacting the compound of Formula (I-a):

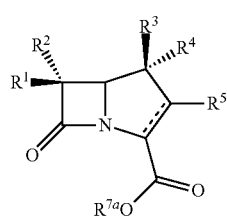

or a salt or tautomer thereof, or a combination thereof; wherein ---- represents a double bond, with a compound of the formula:

R⁸'—X wherein:
X is a leaving group; and
R⁸' is selected from the group consisting of —C(=O)R⁸ᵃ, —C(=O)OR⁸ᵃ, —C(=O)SR⁸ᵃ, —C(=O)N(R⁸ᵇ)₂, —C(=NR⁸ᵇ)R⁸ᵃ, —C(=NR⁸ᵇ)OR⁸ᵃ, —C(=NR⁸ᵇ)SR⁸ᵃ, —C(=NR⁸ᵇ)N(R⁸ᵇ)₂, —C(=S)R⁸ᵃ, —C(=S)OR⁸ᵃ, —C(=S)SR⁸ᵃ, —C(=S)N(R⁸ᵇ)₂, —C(=O)NR⁸ᵇSO₂R⁸ᵃ, —S(=O)R⁸ᵃ, —SO₂R⁸ᵃ, —SO₂N(R⁸ᵃ)₂, —Si(R⁸ᵃ)₃, —P(=O)(R⁸ᵃ)₂, —P(=O)(OR⁸ᵃ)₂, —P(=O)(R⁸ᵃ)(OR⁸ᵃ), —P(=O)(R⁸ᵃ)(N(R⁸ᵇ)₂), —P(=O)(N(R⁸ᵇ)₂)₂, —P(=O)₂R⁸ᵃ, —P(=O)₂OR⁸ᵃ, —P(=O)₂N(R⁸ᵇ)₂, —B(R⁸ᵃ)₂, —B(OR⁸ᵃ)₂, and —BR⁸ᵃ(OR⁸ᵃ), wherein R⁸ᵃ is selected from the group consisting of optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, optionally substituted heteroaryl, if attached to an oxygen atom an oxygen protecting group, and if attached to a sulfur atom a sulfur protecting group, or two R⁸ᵃ groups or an R⁸ᵃ and R⁸ᵇ group are joined to form an optionally substituted heterocyclic ring; and each instance of R⁸ᵇ is independently selected from the group consisting of hydrogen, optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, optionally substituted heteroaryl, and a nitrogen protecting group, or two R⁸ᵇ are joined to form an optionally substituted heterocyclic ring;
to provide a compound of Formula (I-e):

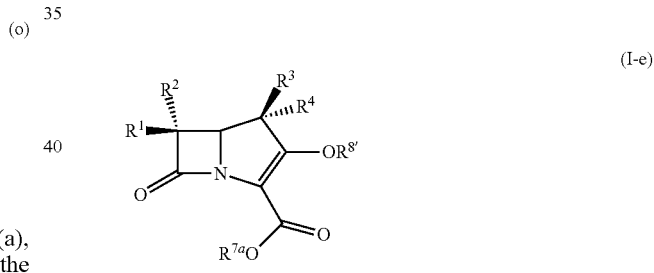

or salt thereof. In certain embodiments, R¹ is hydrogen. In certain embodiments, R² is hydrogen, —CH₂, or —CH₂CH₃. In certain embodiments, R³ is hydrogen or —CH₃. In certain embodiments, R⁴ is hydrogen. In certain embodiments, X is —Cl, —Br, or —I. In certain embodiments, X is a sulfonate.

In certain embodiments, wherein R¹ and R⁴ are hydrogen, the compound of Formula (I-e) is a compound of the Formula (I-f):

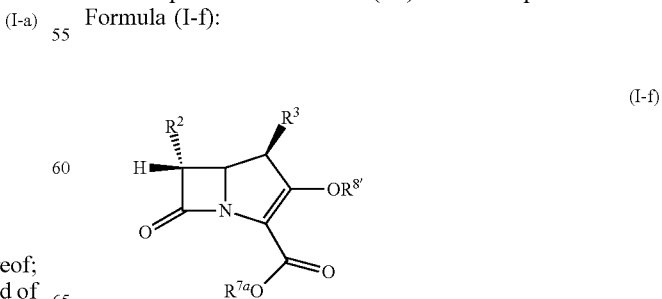

or salt thereof.

Figure 8:
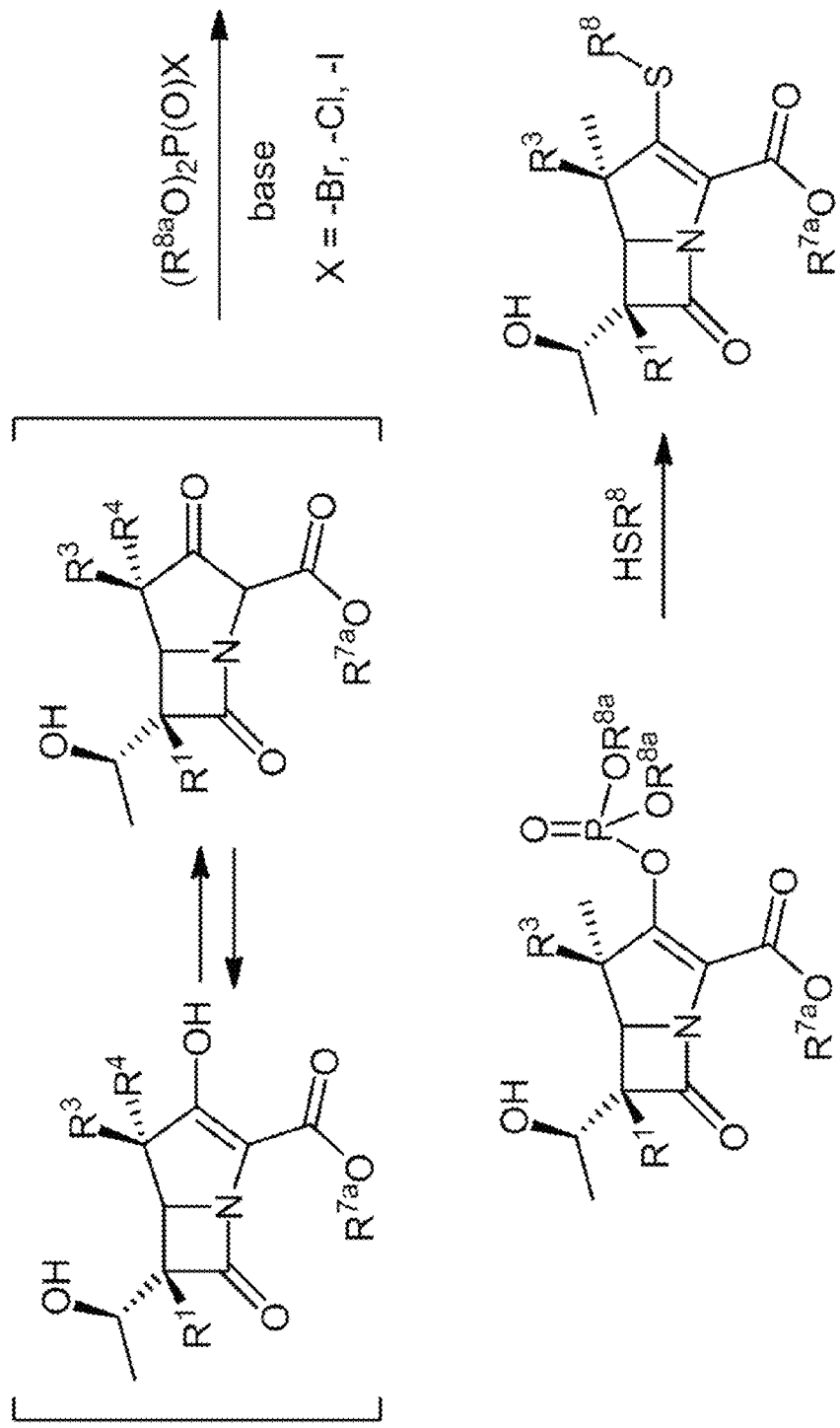
FIG. 8 depicts the chemical attachment of a C2 side chain by trapping the enol form, followed by treatment with $SHR^8$ to provide, via a tandem Michael addition-elimination reaction, a carbapenem.
Figure 9A:
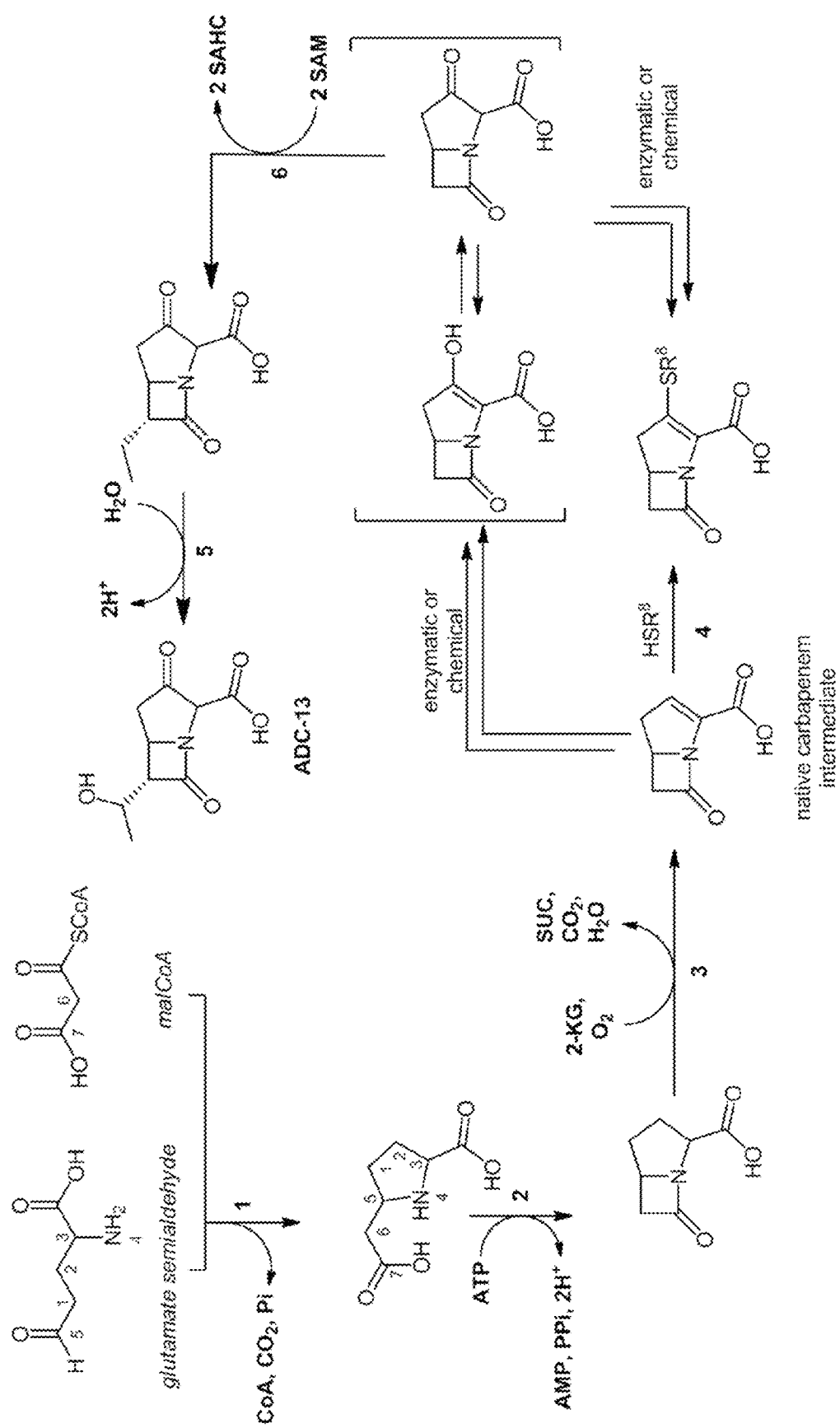
FIGS. 9A-9H depict the production of the carbapenem scaffold following the inventive method, e.g., from glutamate semialdehyde and malonyl-CoA (FIG. 9A) or ethylmalonyl-CoA (FIG. 9B), from 4-methylglutamate semialdehyde and ethylmalonyl-CoA (FIG. 9C) or malonyl-CoA (FIG. 9F), from 3-hydroxyglutamate semialdehyde and ethylmalonyl-CoA (FIG. 9D) or malonyl-CoA (FIG. 9G), from 3-hydroxy-4-methyl-glutamate semialdehyde and ethylmalonyl-CoA (FIG. 9E) or malonyl-CoA (FIG. 9H). The glutamate semialdehyde compound may spontaneously cyclize to form a pyrrole compound in situ (not shown).
Figure 9B:
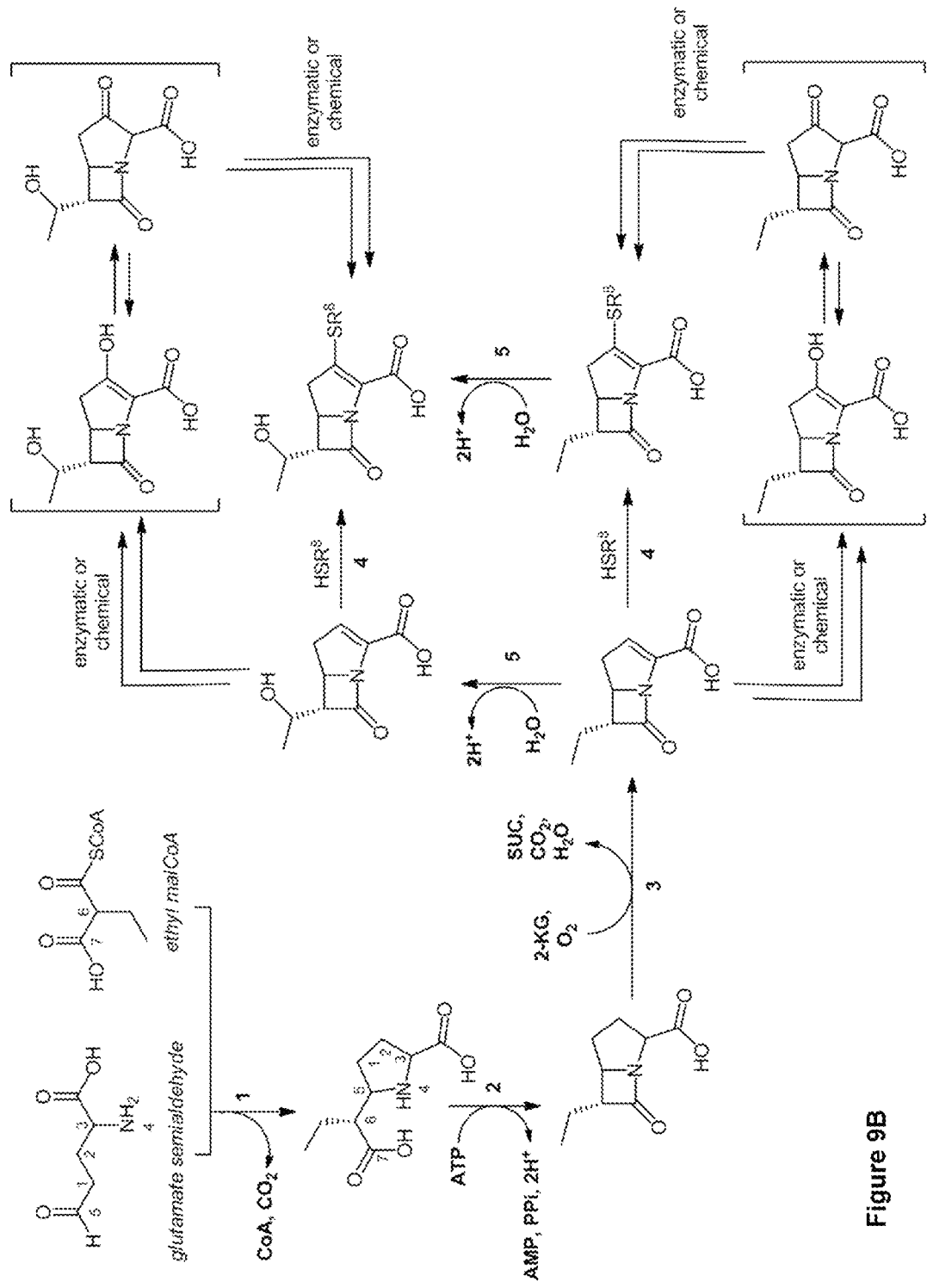
Figure 9C:
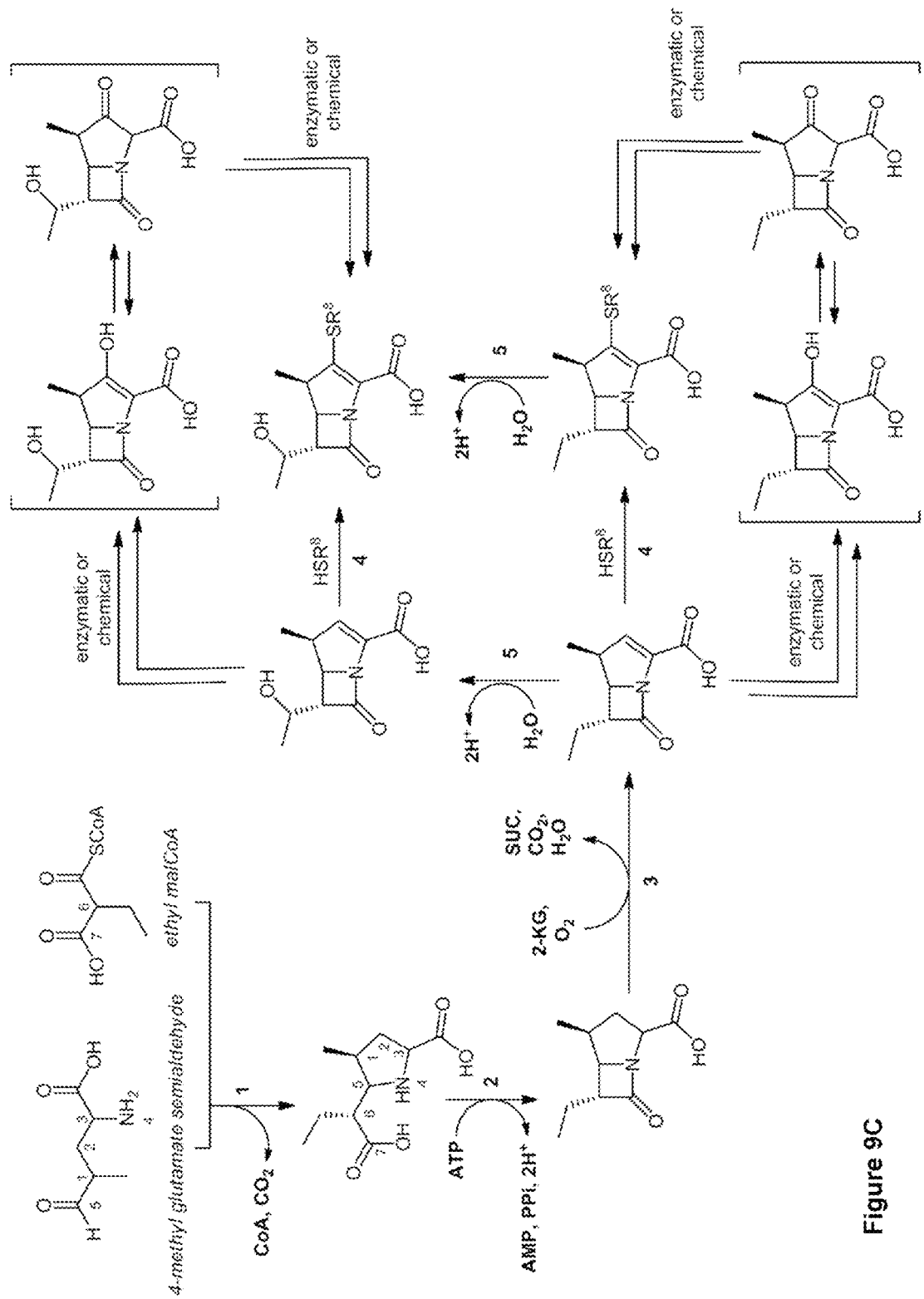
Figure 9D:
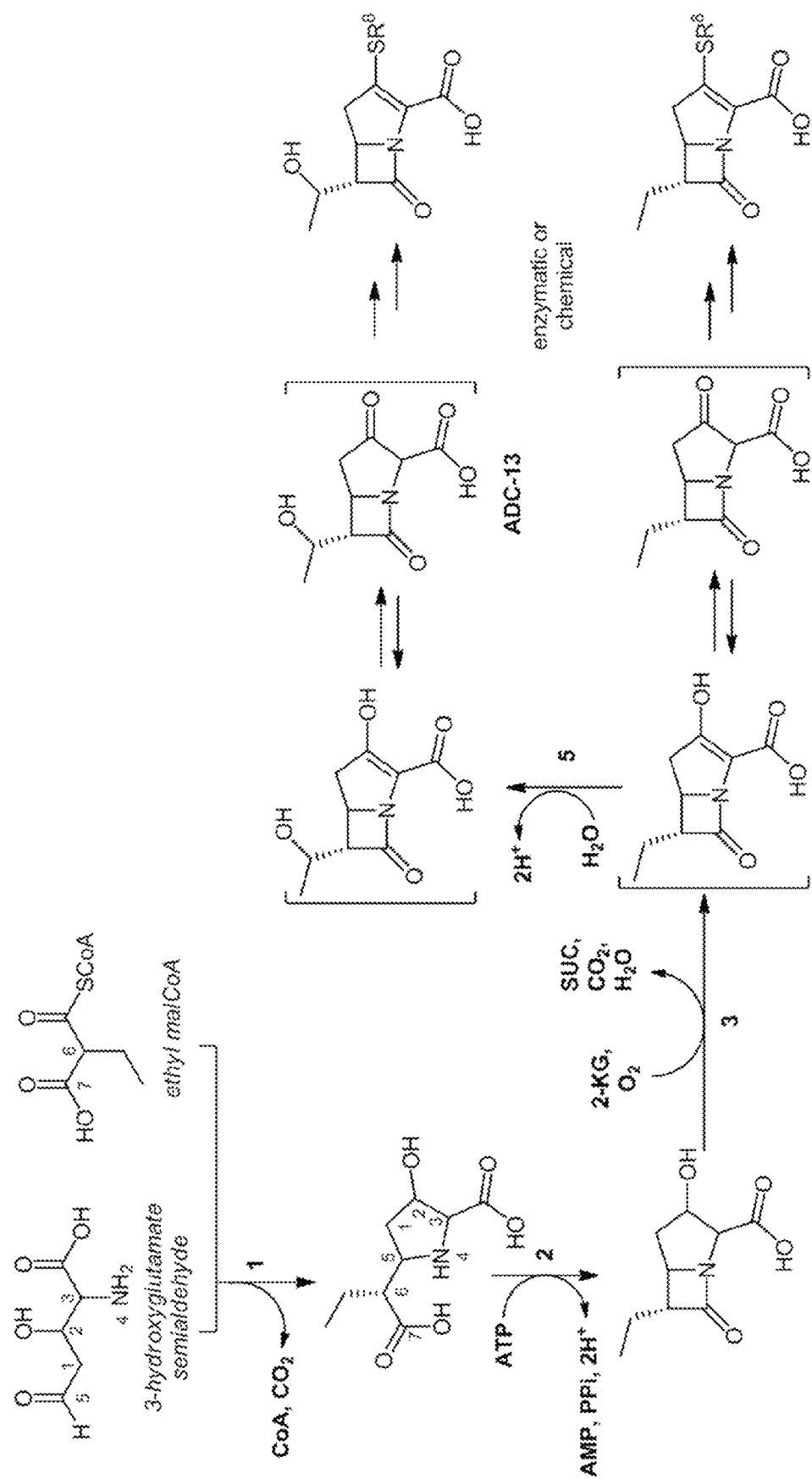
Figure 9E:
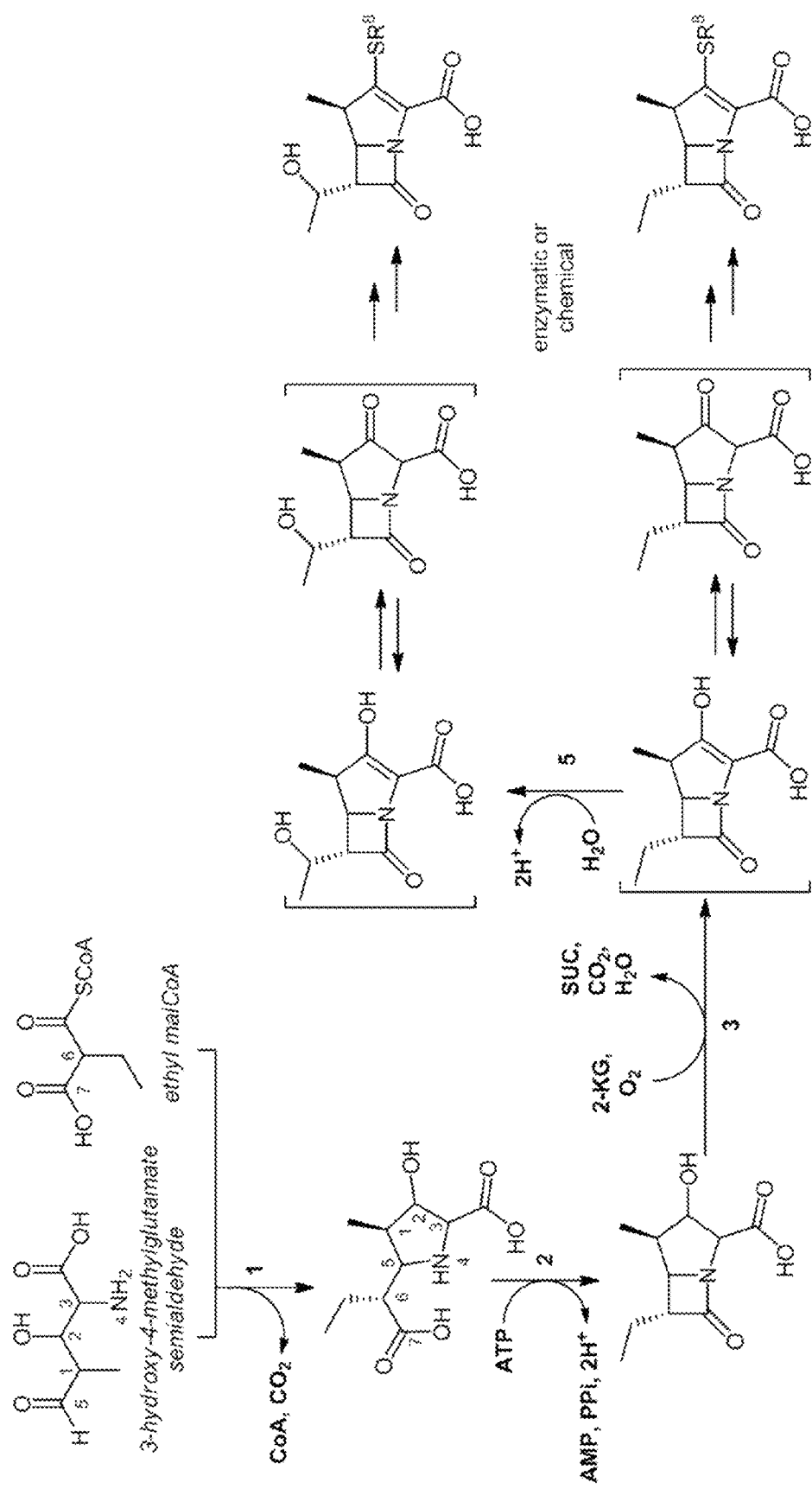
Figure 9F:
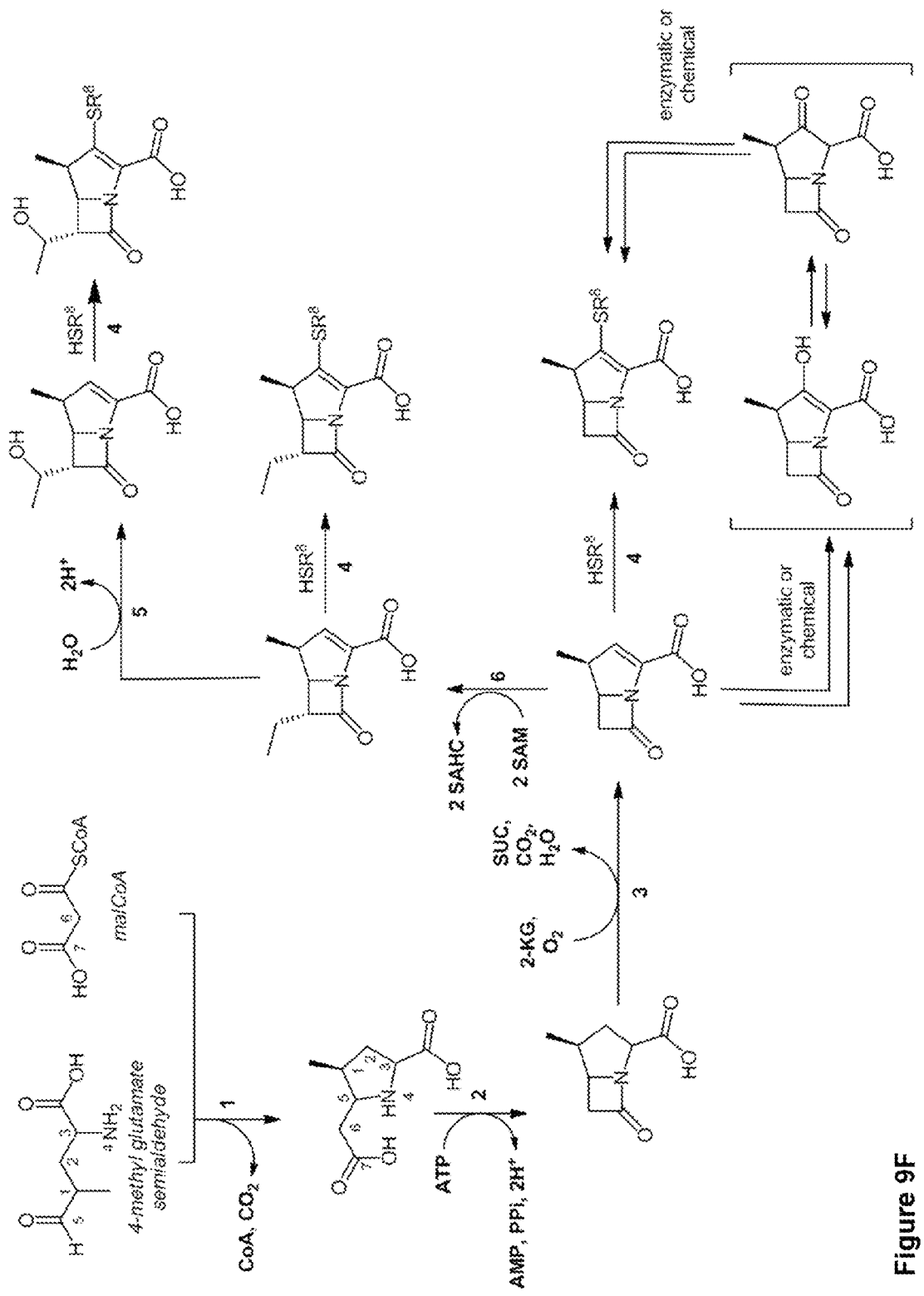
Figure 9G:
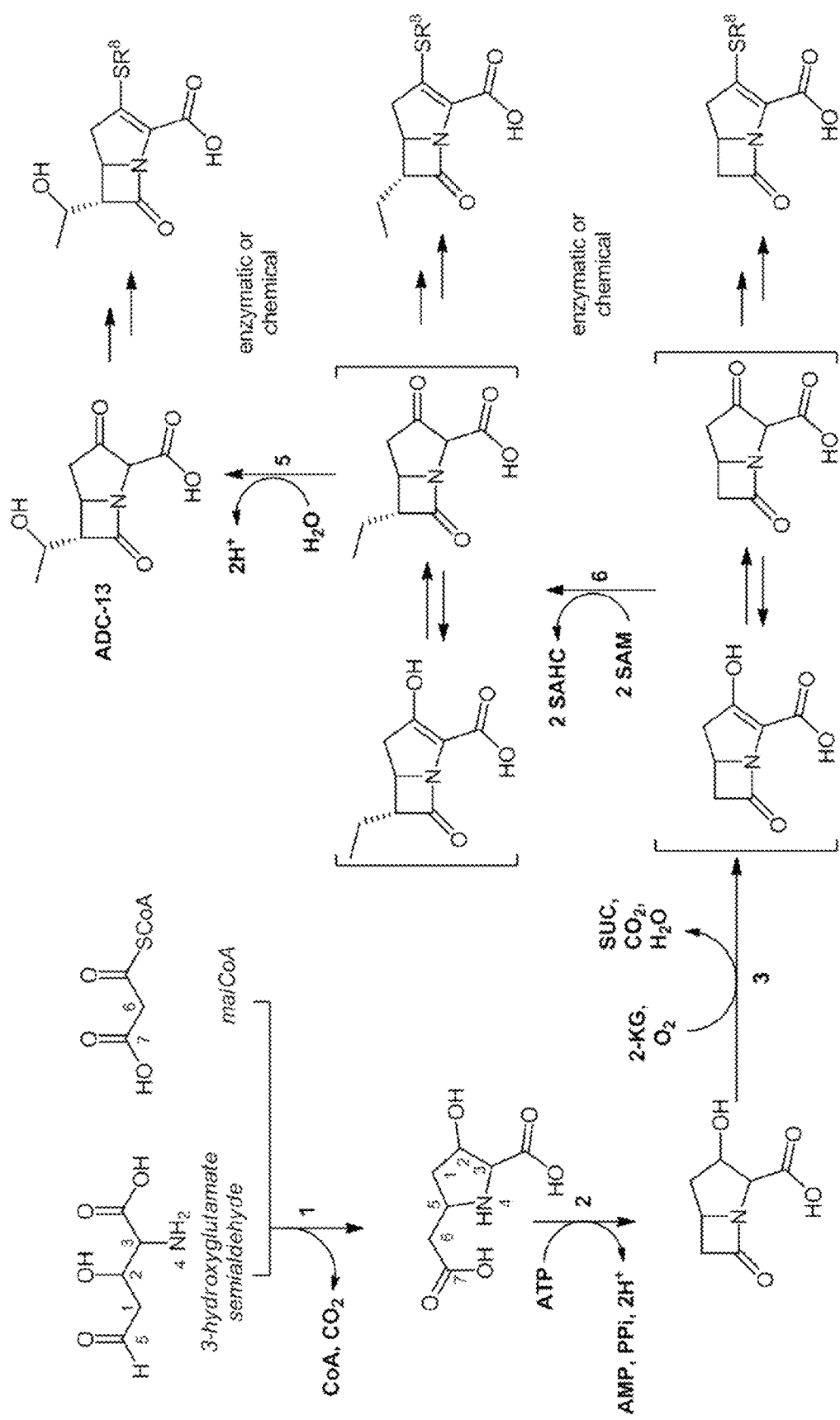
Figure 9H:
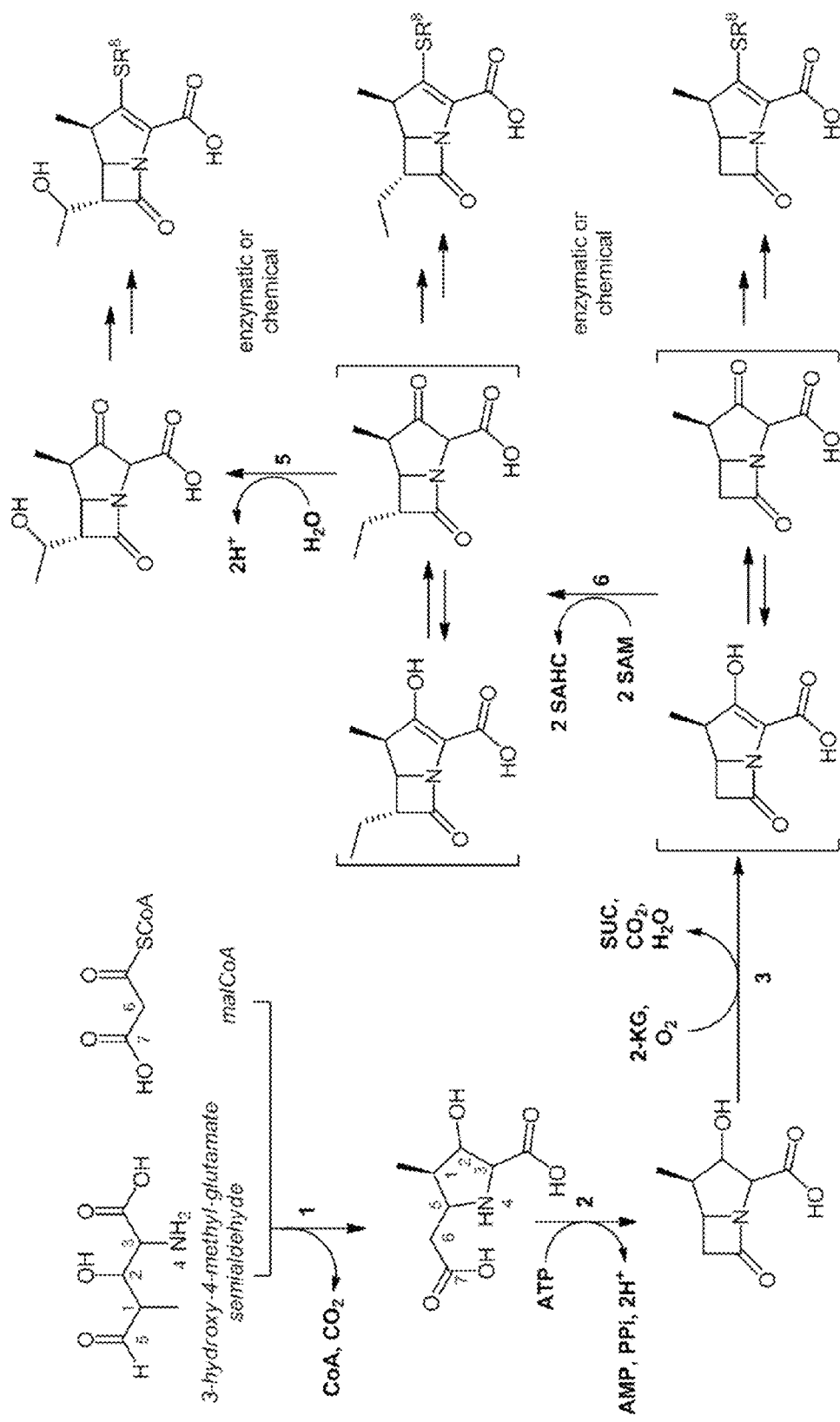

In certain embodiments, $R^{8'}$ is selected from the group consisting of —C(=O)$R^{8a}$, —C(=S)$R^{8a}$, —SO$_2R^{8a}$, —P(=O)($R^{8a}$)$_2$, —P(=O)(O$R^{8a}$)$_2$, —P(=O)($R^{8a}$)(O$R^{8a}$), —P(=O)($R^{8a}$)(N($R^{8b}$)$_2$), —P(=O)(N($R^{8b}$)$_2$)$_2$, —P(=O)$_2R^{8a}$, —P(=O)$_2$O$R^{8a}$, and —P(=O)$_2$N($R^{8b}$)$_2$. In certain embodiments, $R^{8'}$ is selected from the group consisting of —C(=O)$R^{8a}$ and —P(=O)(O$R^{8a}$)$_2$. In certain embodiments, $R^{8'}$ is —C(=O)$R^{8a}$. In certain embodiments, $R^{8'}$ is —P(=O)(O$R^{8a}$)$_2$. See, e.g., FIG. 8.

In certain embodiments, the compound of Formula (I-e) is contacted with a a compound of the formula HS—$R^8$, wherein $R^8$ is selected from the group consisting of optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, and optionally substituted heteroaryl;

to provide a thiol-containing compound of Formula (I-c):

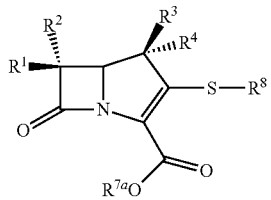

(I-c)

or salt thereof. In certain embodiments, $R^1$ is hydrogen. In certain embodiments, $R^2$ is hydrogen, —CH$_2$, or —CH$_2$CH$_3$. In certain embodiments, $R^3$ is hydrogen or —CH$_3$. In certain embodiments, $R^4$ is hydrogen.

In certain embodiments, the reaction between the compound of Formula (I-e) and HS—$R^8$ comprises a tandem Michael addition, followed by elimination of the group —O$R^{8'}$. In certain embodiments, the tandem Michael addition-elimination reaction further comprises a base.

Oxidation of the C2 Thiol-Containing Side Chain

In certain embodiments, the method further comprises oxidation of the thiol-containing side chain attached to the carbapenem scaffold. For example, in certain embodiments, the —S$R^8$ group attached thereto is partially oxidized to a sulfinyl group, —S(=O)$R^8$, or fully oxidized to a sulfonyl group, —S(=O)$_2R^8$. Oxidation of a sulfur to a sulfinyl or sulfonyl group may employ chemical and/or enzymatic methods. Such methods are well-known in the art. See, e.g., Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987, for examples of reaction conditions useful for this type of oxidation.

Attachment of the C6 Side Chain

Figure 6A:
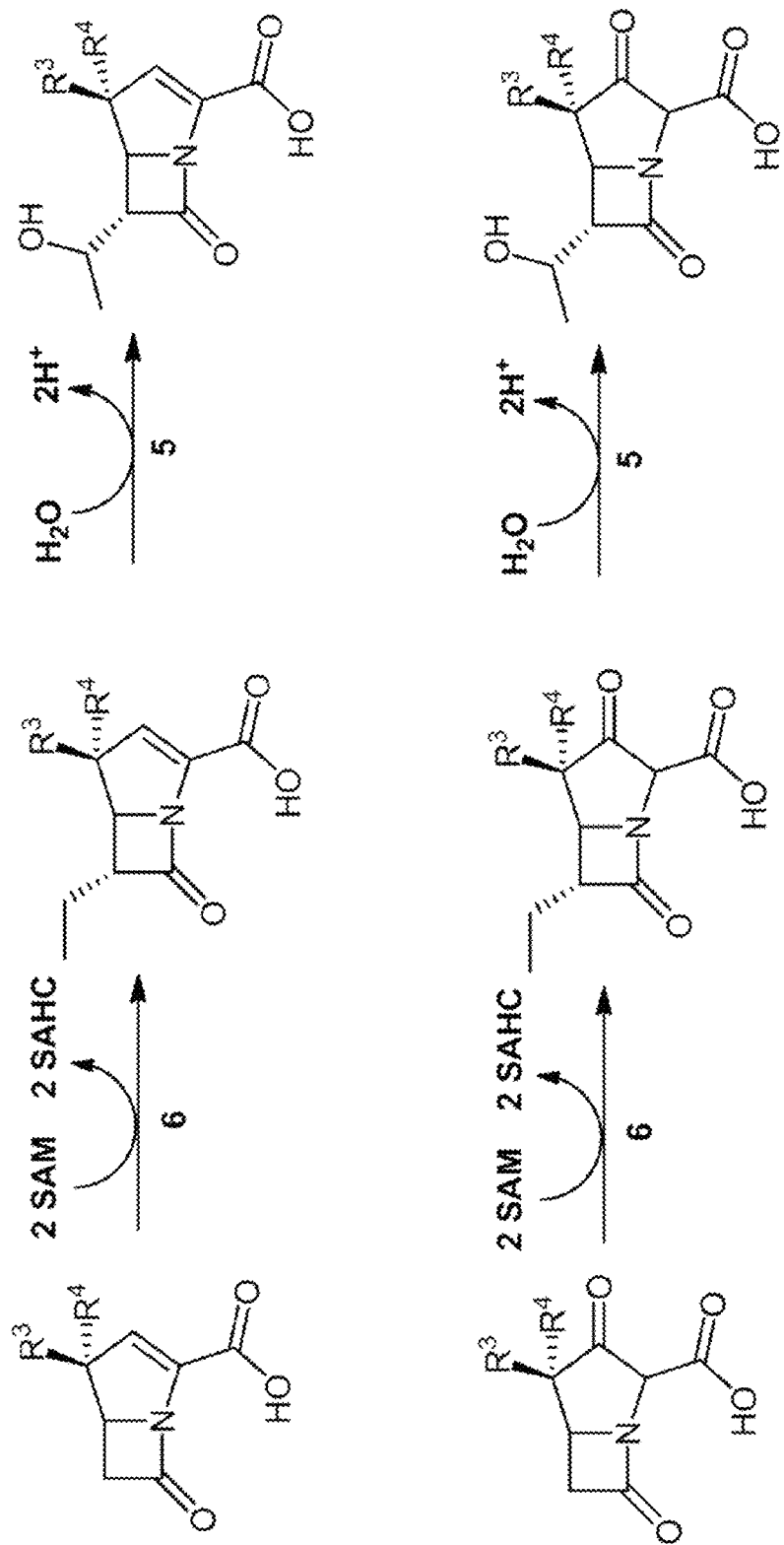
FIG. 6A depicts the enzymatic attachment of a C6 side chain, and subsequent enzymatic hydroxylation of the C6 ethyl group to provide an exemplary carbapenem.

In certain embodiments, the method comprises attachment of a C6 side chain by enzymatic methods. For example, in certain embodiments, wherein $R^1$ and $R^2$ are both H, the method comprises contacting a compound of Formula (I) with a methyltransferase enzyme (e.g., *S. cattalya* ThnL, ThnP, ThnK, or isozyme thereof) to provide a compound wherein $R^2$ is alkyl, e.g., n-alkyl groups such as —CH$_3$ (methyl, Me) or —CH$_2$CH$_3$ (ethyl, Et). In certain embodiments, S-adenosylmethionine (SAM) is used as the methyl donor for these enzymes (Thn L/K/P). See, e.g., FIG. 6A. In certain embodiments, addition of one methyl group comprises one reaction cycle, or two methyl groups added sequentially to give ethyl comprises two reaction cycles. Additional methyl groups may be similarly transferred to form other n-alkyl groups, such as n-propyl and n-butyl.

In certain embodiments, contact of a compound of Formula (I-a) or (I-c), when $R^1$ and $R^2$ are both hydrogen, with a methyltransferase enzyme provides alkylated compounds of the Formula (I-u) or (I-v), respectively, i.e., wherein an ethyl group is added:

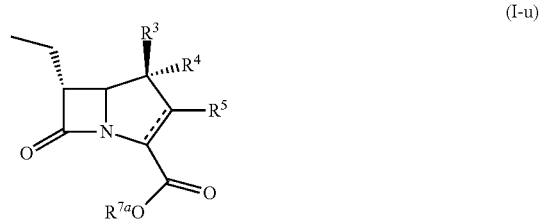

(I-u)

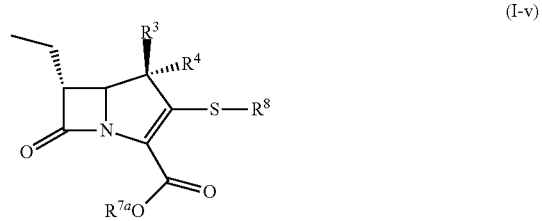

(I-v)

or a salt or tautomer thereof, or a combination thereof.

In certain embodiments, when $R^1$ and $R^4$ are hydrogen, the compounds of Formula (I-u) and (I-v) are of the Formula (I-w) and (I-x), respectively:

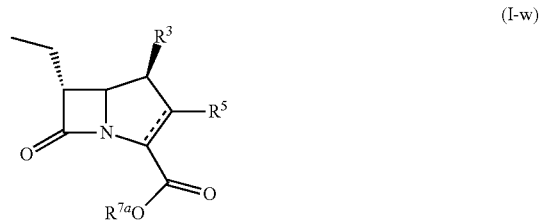

(I-w)

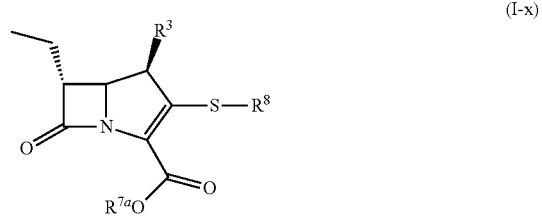

(I-x)

or a salt or tautomer thereof, or a combination thereof.

In certain embodiments, the methyltransferase enzyme is an enzyme which is expressed by the cell. In certain embodiments, the methyltransferase enzyme is an enzyme which is expressed by the cell and sequestered in the periplasmic space. Upon lysing the cell, the methyltransferase enzyme is free to react with the compound of Formula (I-a) or (I-c).

However, in certain embodiments, the methyltransferase enzyme is not expressed by the cell and sequestered in the periplasmic space. In certain embodiments, the methyltransferase enzyme is contacted with the compound of Formula (I-a) or (I-c) after lysing the cell, e.g., after the cell-free production of said compound.

In certain embodiments, the methyltransferase enzyme is *S. cattalya* ThnL. In certain embodiments, the methyltransferase enzyme is *S. cattalya* ThnP. In certain embodiments, the methyltransferase enzyme is *S. cattalya* ThnK.

In certain embodiments, two or more of ThnL, ThnP, and ThnK are used, e.g., for example, to produce the methyl or ethyl side chain. In certain embodiments, ThnL and ThnP are used, e.g., for example, to produce the methyl or ethyl side chain. In certain embodiments, ThnL and ThnK are used, e.g., for example, to produce the methyl or ethyl side chain. In certain embodiments, ThnK and ThnP are used, e.g., for example, to produce the methyl or ethyl side chain. In certain embodiments, all of ThnL, ThnP, and ThnK are used, e.g., for example, to produce the methyl or ethyl side chain.

In certain further embodiments, when ---- represents a double bond, and $R^5$ is hydrogen or —OH, the alkylated compound of Formula (I-u) may be converted, via enzymatic or chemical methods as described herein, to a compound of Formula (I-v).

Oxidation of the C6 Side Chain

In certain embodiments, the method comprises oxidation of a C6 side chain by enzymatic methods. For example, in certain embodiments, when $R^2$ is —$CH_3$, the method further comprises contacting the compound of Formula (I) with an oxygenase enzyme to provide a compound wherein $R^2$ is —$CH_2OH$. In certain embodiments, when $R^2$ is —$CH_2CH_3$, the method further comprises contacting the compound of Formula (I) with an oxygenase enzyme to provide a compound wherein $R^2$ is —$CH(OH)CH_3$. For example, in certain embodiments, contact of a compound of Formula (I-a) or (I-c), when $R^2$ is —$CH_2CH_3$, with an oxygenase enzyme provides hydroxylated compounds of the Formula (I-g) or (I-h), respectively:

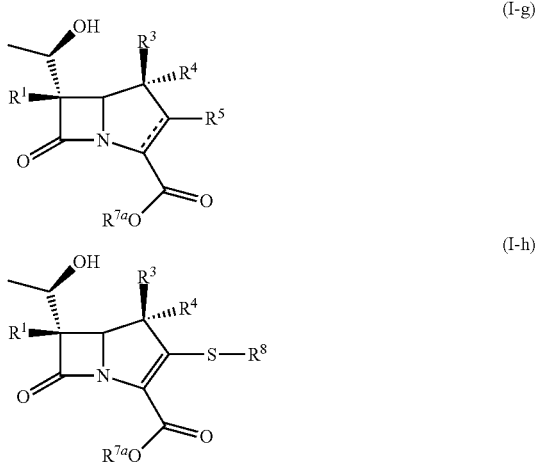

or a salt or tautomer thereof, or a combination thereof.

In certain embodiments, when $R^1$ and $R^4$ are hydrogen, the compounds of Formula (I-g) and (I-h) are of the Formula (I-i) and (I-j), respectively:

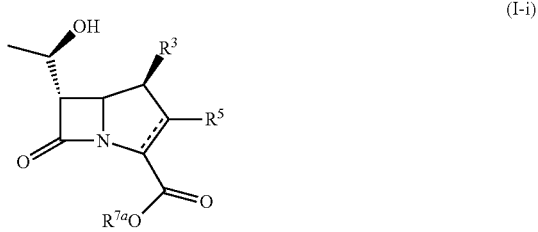

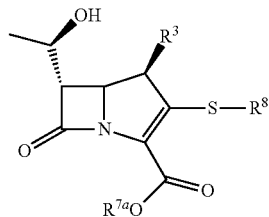

or a salt or tautomer thereof, or a combination thereof.

In certain embodiments, the oxygenase enzyme is an enzyme which is expressed by the cell. In certain embodiments, the oxygenase enzyme is an enzyme which is expressed by the cell and sequestered in the periplasmic space prior to lysing. Upon lysing the cell, the oxygenase enzyme is free to react with the compound of Formula (I-a) or (I-c).

However, in certain embodiments, the oxygenase enzyme is not expressed by the cell and sequestered in the periplasmic space. In certain embodiments, the oxygenase enzyme is contacted with the compound of Formula (I-a) or (I-c) after lysing the cell, e.g., after the cell-free production of said compound. In certain embodiments, the oxygenase enzyme is an *S. cattleya* oxygenase enzyme, or an enzyme of the 2-oxoglutarate and/or Fe(II)-dependent oxygenase superfamily. In certain embodiments, the *S. cattleya* oxygenase enzyme is ThnQ.

In certain further embodiments, when ---- is a double bond, and $R^5$ is hydrogen or —OH, the hydroxylated compound of Formula (I-g) may be converted, via enzymatic or chemical methods as described herein, to a compound of Formula (I-h).

Functionalization of the C3 Side Chain

The present invention further contemplates enzymatic or chemical manipulation of the C3 side chain.

In certain embodiments, the C3 side chain group —C(=O)$OR^{7a}$, wherein $R^{7a}$ is hydrogen, is converted to an ester (—C(=O)$OR^{7a}$, wherein $R^{7a}$ is not hydrogen), thioester (—C(=O)$SR^{7a}$), or amide (—C(=O)$N(R^{7b})_2$) group. Converting a carboxylic acid group to an ester, thioester, or amide may employ methods known in the art, e.g., via chemical methods such as generating an activated carboxylic acid (e.g., such as generating an acyl chloride or using coupling agents) and treating the activated carboxylic acid with a nucleoptile, such as $HOR^{7a}$, $HSR^{7a}$, or $HN(R^{7b})_2$; or via enzymatic methods. See, e.g., Smith and March *March's Advanced Organic Chemistry*, $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, $3^{rd}$ Edition, Cambridge University Press, Cambridge, 1987, for examples of reaction conditions useful in these types of conversions.

In other embodiments, the C3 side chain group —C(=O)$OR^{7a}$ may be further synthetically manipulated, e.g., via one or more chemical and/or enzymatic steps, to provide a different C3 side chain, e.g., wherein $R^6$ is selected from the group consisting of optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, and optionally substituted heteroaryl. For example, in certain embodiments, the —C(=O)

$OR^{7a}$ may be reduced to an aldehyde group —CHO and optionally further reacted under, for example, Wittig conditions, to provide an optionally substituted alkenyl group, —CH=CH($R^{7a}$), wherein $R^{7a}$ is as defined herein, which may be further synthetically manipulated. In other embodiments, the aldehyde group —CHO may be further reacted with a primary amine $H_2NR^{7b}$ via reductive amination to provide an aminated group, —CH$_2$—NH($R^{7b}$), wherein $R^{7b}$ is as defined herein, which may be further synthetically manipulated. In still yet other embodiments, the —C(=O)$OR^{7a}$ may be reduced to an alcohol —CH$_2$OH, which may be converted to an activated alkyl group —CH$_2$X, wherein X is a leaving group, which may be further synthetically manipulated. It should be understood that the above are merely examples of the types of groups one skilled in the art could access using a combination of known chemical and/or enzymatic techniques. Various other functional groups encompassed by the definition of $R^6$ of Formula (I) may be accessed using known chemistry.

Other Embodiments of Compounds of Formula (I)

Exemplary compounds of Formula (I) which may be final products or intermediates may be prepared by the inventive cell-free system and methods. Various combinations of $R^1$, $R^2$, $R^3$, $R^4$, $R^5$, and $R^6$ are contemplated as would be appreciated by one of skill in the art, and the subgenera disclosed are not to be considered limiting.

For example, in certain embodiments of Formula (I), wherein $R^1$ and $R^4$ are hydrogen, the compound is of Formula (I-k):

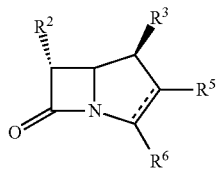

(I-k)

or salt thereof, wherein ----, $R^2$, $R^3$, $R^5$, and $R^6$ are as defined herein. In certain embodiments, $R^2$ is hydrogen, —CH$_3$, —CH$_2$CH$_3$, —CH$_2$OH, or CH(OH)CH$_3$. In certain embodiments, $R^3$ is hydrogen or —CH$_3$. In certain embodiments, $R^5$ is hydrogen, —OR$^{8'}$, —OR$^8$, or —SR$^8$. In certain embodiments, $R^8$ is optionally substituted alkyl, optionally substituted heteroalkyl, or optionally substituted heterocyclyl. In certain embodiments, $R^8$ is a group of Formula (a), (b), or (c). In certain embodiments, $R^6$ is —C(=O)$R^7$. In certain embodiments, $R^7$ is —OR$^{7a}$. In certain embodiments, ---- is a double bond.

In certain embodiments, wherein $R^5$ is —SR$^8$, provided is a compound of Formula (I-m):

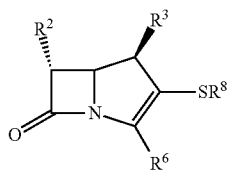

(I-m)

or salt thereof, wherein $R^2$, $R^3$, $R^6$, and $R^8$ are as defined herein. In certain embodiments, $R^2$ is selected from hydrogen, —CH$_3$, —CH$_2$OH, —CH$_2$CH$_3$, —CH(CH$_3$)$_2$, or —CH(OH)CH$_3$. In certain embodiments, $R^3$ is hydrogen or —CH$_3$. In certain embodiments, $R^8$ is optionally substituted alkyl, optionally substituted heteroalkyl, or optionally substituted heterocyclyl. In certain embodiments, $R^8$ is a group of Formula (a), (b), or (c). In certain embodiments, $R^6$ is —C(=O)$R^7$. In certain embodiments, $R^7$ is —OR$^{7a}$.

In certain embodiments of (I-m), wherein $R^3$ is —CH$_3$, provided is a compound of Formula (I-n):

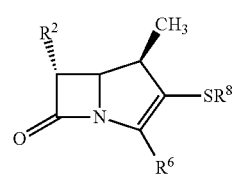

(I-n)

or salt thereof, wherein $R^2$, $R^6$, and $R^8$ are as defined herein. In certain embodiments, $R^2$ is selected from hydrogen, —CH$_3$, —CH$_2$OH, —CH$_2$CH$_3$, —CH(CH$_3$)$_2$, or —CH(OH)CH$_3$. In certain embodiments, $R^8$ is optionally substituted alkyl, optionally substituted heteroalkyl, or optionally substituted heterocyclyl. In certain embodiments, $R^8$ is a group of Formula (a), (b), or (c). In certain embodiments, $R^6$ is —C(=O)$R^7$. In certain embodiments, $R^7$ is —OR$^{7a}$.

In certain embodiments of (I-n), wherein $R^2$ is —CH$_2$CH$_3$, and $R^3$ is —CH$_3$, provided is a compound of Formula (I-o):

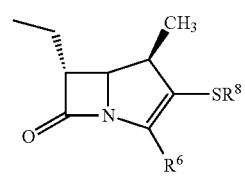

(I-o)

or salt thereof, wherein $R^6$ and $R^8$ are as defined herein. In certain embodiments, $R^8$ is optionally substituted alkyl, optionally substituted heteroalkyl, or optionally substituted heterocyclyl. In certain embodiments, $R^8$ is a group of Formula (a), (b), or (c). In certain embodiments, $R^6$ is —C(=O)$R^7$. In certain embodiments, $R^7$ is —OR$^{7a}$.

In certain embodiments of (I-n), wherein $R^2$ is —CH(OH)CH$_3$, and $R^3$ is —CH$_3$, provided is a compound of Formula (I-o):

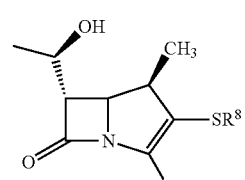

(I-p)

or salt thereof, wherein $R^6$ and $R^8$ are as defined herein. In certain embodiments, $R^8$ is optionally substituted alkyl, optionally substituted heteroalkyl, or optionally substituted heterocyclyl. In certain embodiments, $R^8$ is a group of Formula (a), (b), or (c). In certain embodiments, $R^6$ is —C(=O)$R^7$. In certain embodiments, $R^7$ is —OR$^{7a}$.

In certain embodiments of (I-m), wherein $R^3$ is hydrogen, provided is a compound of Formula (I-q):

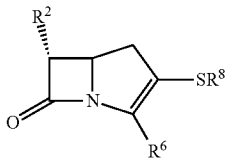

(I-q)

or salt thereof, wherein $R^2$, $R^6$, and $R^8$ are as defined herein. In certain embodiments, $R^2$ is selected from hydrogen, —$CH_3$, —$CH_2OH$, —$CH_2CH_3$, —$CH(CH_3)_2$, or —CH(OH)$CH_3$. In certain embodiments, $R^8$ is optionally substituted alkyl, optionally substituted heteroalkyl, or optionally substituted heterocyclyl. In certain embodiments, $R^8$ is a group of formula (a), (b), or (c). In certain embodiments, $R^6$ is —C(=O)$R^7$. In certain embodiments, $R^7$ is —$OR^{7a}$.

In certain embodiments of (I-q), wherein $R^2$ is —$CH_2CH_3$, and $R^3$ is —$CH_3$, provided is a compound of Formula (I-r):

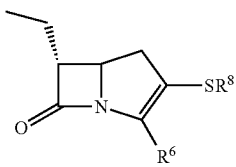

(I-r)

or salt thereof, wherein $R^6$ and $R^8$ are as defined herein. In certain embodiments, $R^8$ is optionally substituted alkyl, optionally substituted heteroalkyl, or optionally substituted heterocyclyl. In certain embodiments, $R^8$ is a group of Formula (a), (b), or (c). In certain embodiments, $R^6$ is —C(=O)$R^7$. In certain embodiments, $R^7$ is —$OR^{7a}$.

In certain embodiments of (I-q), wherein $R^2$ is —CH(OH)$CH_3$, and $R^3$ is hydrogen, provided is a compound of Formula (I-s):

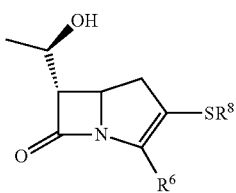

(I-s)

or salt thereof, wherein $R^6$ and $R^8$ are as defined herein. In certain embodiments, $R^8$ is optionally substituted alkyl, optionally substituted heteroalkyl, or optionally substituted heterocyclyl. In certain embodiments, $R^8$ is a group of Formula (a), (b), or (c). In certain embodiments, $R^6$ is —C(=O)$R^7$. In certain embodiments, $R^7$ is —$OR^{7a}$.

For example, in certain embodiments of Formula (I-s), wherein $R^2$ is —CH(OH)$CH_3$, $R^3$ is hydrogen, $R^6$ is —C(=O)$R^7$, and $R^8$ is a group of the Formula (b), provided is a compound of the Formula (I-t):

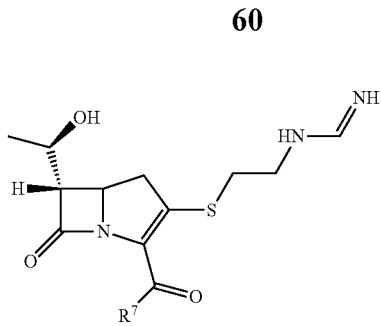

(I-t)

or a salt thereof. Compounds of Formula (I-t) are referred to herein as the compound imipenem (wherein $R^7$ is —OH) or an imipenem derivative (i.e., wherein $R^7$ is —$OR^{7a}$, —SH, —$SR^{7a}$, —$N(R^{7b})_2$, wherein $R^{7a}$ is not hydrogen). In certain embodiments, the imipenem derivative is a prodrug of imipenem.

Other exemplary compounds of Formula (I) are selected from the group consisting of:

ertapenem

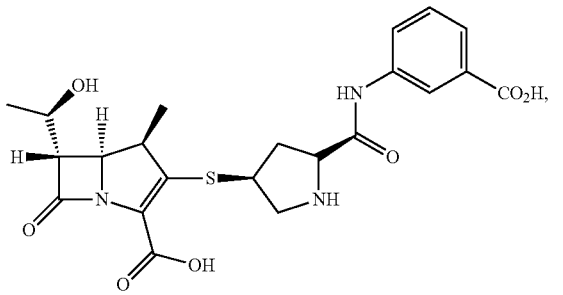

meropenem

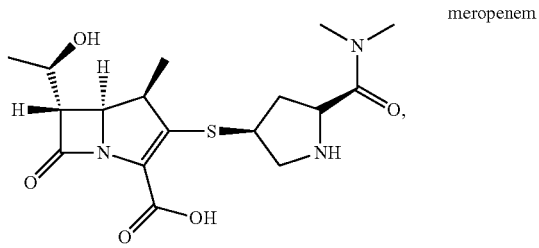

panipenem

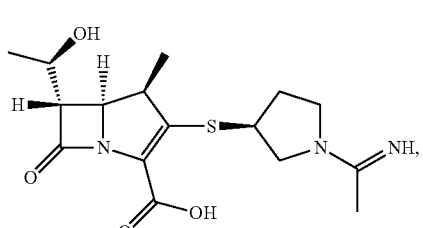

biapenem

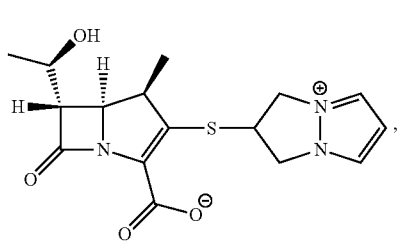

doripenem

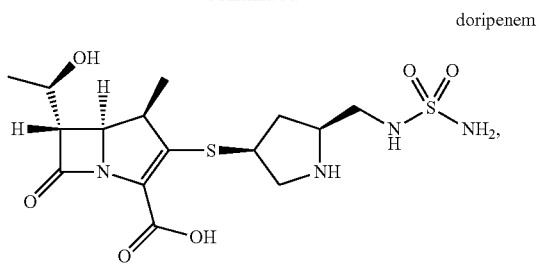

ER-35768

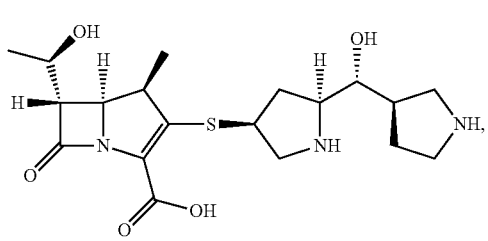

lenapenem

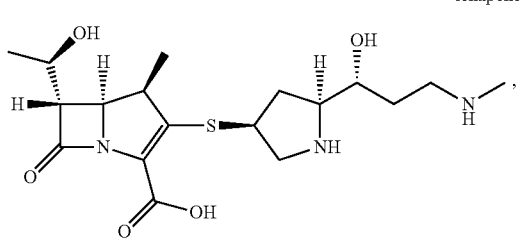

L-646591

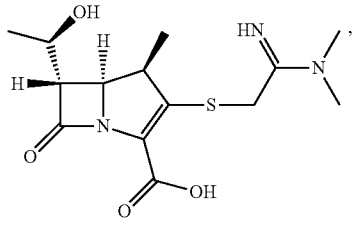

CL-191121

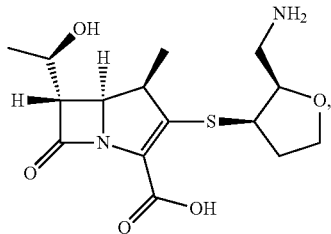

L-036

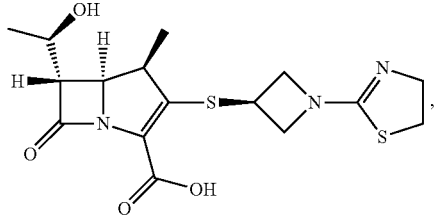

L-084

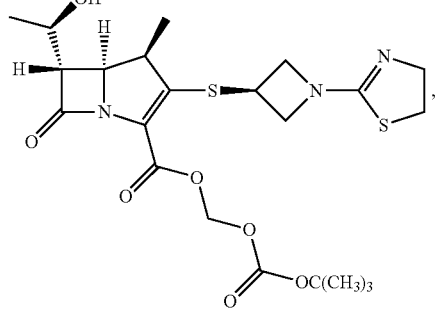

DU-6681

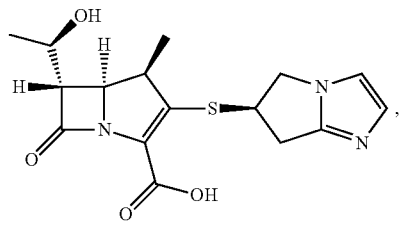

DZ-2640

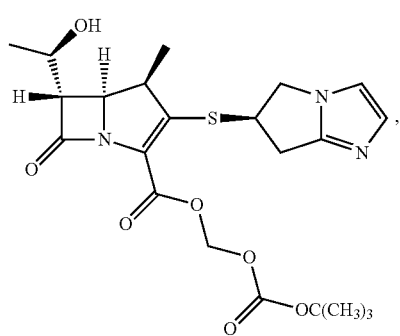

R-95867

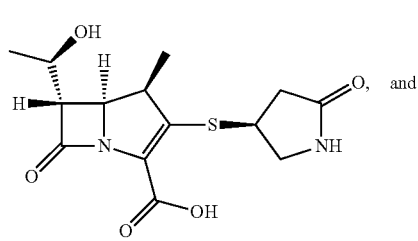

and

CS-834

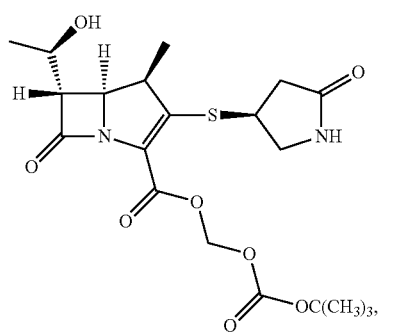

and salts thereof.

Recombinant Gene Expression and Cell Culture

The genes encoding enzymes associated with the invention can be obtained from a variety of sources. As one of ordinary skill in the art would be aware, homologous genes for these enzymes exist in many species and can be identified by homology searches, for example, through a protein BLAST search, available at the NCBI internet site (www.ncbi.nlm.nih.gov). Genes encoding for these enzymes can be amplified by PCR from DNA from any source which contains the given enzyme, for example, using degenerate primers, as would be understood by one of ordinary skill in the art. In some embodiments, the gene encoding for a given enzyme can be synthetic. Any means of obtaining the genes encoding for the enzymes discussed herein are compatible with aspects of the instant invention.

The expression of the molecules of the invention may be determined using routine methods known to those of ordinary skill in the art. These methods include, but are not limited to, direct RNA amplification, reverse transcription of RNA to cDNA, real-time RT-PCR, amplification of cDNA, hybridization, and immunologically based assay methods, which include, but are not limited to Western blotting, immunohistochemistry, antibody sandwich capture assay, ELISA, and enzyme-linked immunospot assay (EliSpot assay). For example, the determination of the presence of levels of nucleic acid molecules of the invention in a sample such as a tissue or cell lysate can be carried out via any standard nucleic acid determination assay, including the polymerase chain reaction, or assaying with labeled hybridization probes. Such hybridization methods include, but are not limited to, microarray techniques.

The invention thus involves in one aspect methods involving enzymes, genes encoding those enzymes, functional modifications and variants of the foregoing, as well as uses relating thereto. Homologs and alleles of the nucleic acids of the invention can be identified by conventional techniques. Also encompassed by the invention are methods involving nucleic acids that hybridize under stringent conditions to the nucleic acids described herein. The term "stringent conditions" as used herein refers to parameters with which one of skill in the art is familiar. Nucleic acid hybridization parameters may be found in references which compile such methods, e.g., *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrrolidone, 0.02% bovine serum albumin, 2.5 mM $NaH_2PO_4$ (pH 7), 0.5% SDS, 2 mM EDTA). SSC is 0.15 M sodium chloride/0.015 M sodium citrate, pH 7; SDS is sodium dodecyl sulphate; and EDTA is ethylenediaminetetracetic acid. After hybridization, the membrane upon which the DNA is transferred is washed, for example, in 2×SSC at room temperature and then at 0.1-0.5×SSC/0.1×SDS at temperatures up to 68° C.

There are other conditions, reagents, and so forth which can be used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of nucleic acids of the invention (e.g., by using lower stringency conditions). The skilled artisan also is familiar with the methodology for screening cells and libraries for expression of such molecules which then are routinely isolated, followed by isolation of the pertinent nucleic acid molecule and sequencing.

In general, homologs and alleles typically will share at least 75% nucleotide identity and/or at least 80% amino acid identity to the sequences of nucleic acids and polypeptides, respectively, in some instances will share at least 90% nucleotide identity and/or at least 90 or 95% amino acid identity and in still other instances will share at least 95% nucleotide identity and/or at least 99% amino acid identity. In some embodiments, homologs and alleles will share at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more than 99% nucleotide identity to the sequences of nucleic acids described herein and/or 80%, 81%, 82%, 83%, 84%, 85%, 86%, 87%, 88%, 89%, 90%, 91%, 92%, 93%, 94%, 95%, 96%, 97%, 98%, 99% or more than 99% identity to the sequences of polypeptides described herein.

The homology can be calculated using various, publicly available software tools developed by NCBI (Bethesda, Md.) that can be obtained through the NCBI internet site. Exemplary tools include the BLAST software, also available at the NCBI internet site (www.ncbi.nlm.nih.gov). Pairwise and ClustalW alignments (BLOSUM30 matrix setting) as well as Kyte-Doolittle hydropathic analysis can be obtained using the MacVector sequence analysis software (Oxford Molecular Group). Watson-Crick complements of the foregoing nucleic acids also are embraced by the invention.

In screening for and identifying genes, techniques known to those of ordinary skill in the art such as Southern blots, Northern blots and amplification protocols such as polymerase chain reaction using primers which hybridize to the sequences presented can be applied.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct protein synthesis apparatus, in vitro or in vivo, to incorporate a serine residue into an elongating polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code. The invention also embraces codon optimization to suit optimal codon usage of a host cell.

The invention also provides modified nucleic acid molecules which include additions, substitutions, and deletions of one or more nucleotides. In certain embodiments, these modified nucleic acid molecules and/or the polypeptides they encode retain at least one activity or function of the unmodified nucleic acid molecule and/or the polypeptides, such as the enzymatic activity. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in certain embodiments are sufficiently structurally related to the unmodified nucleic acid molecules so that the modified and unmodified nucleic acid molecules hybridize under stringent conditions.

For example, modified nucleic acid molecules which encode polypeptides having single amino acid changes can be prepared. Each of these nucleic acid molecules can have one, two, three, four, five, six, seven, eight, nine, ten, or more than nucleotide substitutions exclusive of nucleotide changes corresponding to the degeneracy of the genetic code as described herein. Likewise, modified nucleic acid molecules which encode polypeptides having two amino acid changes can be prepared which have, e.g., 2-6 nucleotide changes. Numerous modified nucleic acid molecules like these will be readily envisioned by one of skill in the art, including, for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of structural relation or activity to the nucleic acids and/or polypeptides disclosed herein.

The invention embraces variants of the polypeptides described herein. As used herein, a "variant" of a polypeptide is a polypeptide which contains one or more modifications to the primary amino acid sequence of the polypeptide. Modifications which create an enzyme variant can be made to an enzyme, for example, 1) to alter the cellular distribution of the enzyme; 2) to reduce or eliminate an activity of the enzyme; 3) to enhance or alter a property of an enzyme, protein stability in an expression system, or other property; 4) to provide a novel activity or property to an enzyme, such as addition of an antigenic epitope or addition of a detectable moiety; or 5) to provide equivalent or better binding between an enzyme and an enzymatic substrate.

Modifications to a polypeptide are typically made to the nucleic acid which encodes the polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins. One of skill in the art will be familiar with methods for predicting the effect on protein conformation of a change in protein sequence, and can thus "design" a variant polypeptide according to known methods. One example of such a method is described by Dahiyat and Mayo in *Science* 278:82-87, 1997, whereby proteins can be designed de novo. The method can be applied to a known protein to vary a only a portion of the polypeptide sequence. By applying the computational methods of Dahiyat and Mayo, specific variants of a polypeptide can be proposed and tested to determine whether the variant retains a desired conformation.

In general, variants include polypeptides which are modified specifically to alter a feature of the polypeptide unrelated to its desired physiological activity. For example, cysteine residues can be substituted or deleted to prevent unwanted disulfide linkages. Similarly, certain amino acids can be changed to enhance expression of a polypeptide by eliminating proteolysis by proteases in an expression system (e.g., dibasic amino acid residues in yeast expression systems in which KEX2 protease activity is present).

Mutations of a nucleic acid which encode a polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a gene or cDNA clone to enhance expression of the polypeptide. The activity of variants of polypeptides can be tested by cloning the gene encoding the variant polypeptide into a bacterial or mammalian expression vector, introducing the vector into an appropriate host cell, expressing the variant polypeptide, and testing for a functional capability of the polypeptides as disclosed herein.

The skilled artisan will also realize that conservative amino acid substitutions may be made in polypeptides to provide functionally equivalent variants of the foregoing polypeptides, i.e., the variants retain the functional capabilities of the polypeptides. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g., *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants of the polypeptides include conservative amino acid substitutions in the amino acid sequences of proteins disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In general, it is preferred that fewer than all of the amino acids are changed when preparing variant polypeptides. Where particular amino acid residues are known to confer function, such amino acids will not be replaced, or alternatively, will be replaced by conservative amino acid substitutions. Preferably, 1, 2, 3, 4, 5, 6, 7, 8, 9, 10, 11, 12, 13, 14, 15, 16, 17, 18, 19, residues can be changed when preparing variant polypeptides. It is generally preferred that the fewest number of substitutions is made. Thus, one method for generating variant polypeptides is to substitute all other amino acids for a particular single amino acid, then assay activity of the variant, then repeat the process with one or more of the polypeptides having the best activity.

Conservative amino-acid substitutions in the amino acid sequence of polypeptides to produce functionally equivalent variants of polypeptides typically are made by alteration of a nucleic acid encoding a polypeptide. Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488-492, 1985), or by chemical synthesis of a gene encoding a polypeptide.

Aspects of the invention relate to overexpression of one or more enzymes in a cell. In some embodiments, the cell expresses one or more genes encoding one or more of the enzymes endogenously. Expression of an endogenous gene can be increased by altering the promoter of the gene, such as by inserting a constitutive or inducible promoter. Expression of an endogenous gene can also be increased by expressing additional copies of the gene in a cell, for example, by inserting additional copies of the gene into the chromosome or by expressing one or more copies of the gene on a plasmid.

Aspects of the invention relate to recombinant expression of one or more genes encoding one or more enzymes. In some embodiments genes encoding for enzymes associated with the invention are expressed in recombinant expression vectors. As used herein, a "vector" may be any of a number of nucleic acids into which a desired sequence or sequences may be inserted by restriction and ligation for transport between different genetic environments or for expression in a host cell. Vectors are typically composed of DNA although RNA vectors are also available. Vectors include, but are not limited to: plasmids, fosmids, phagemids, virus genomes and artificial chromosomes.

A cloning vector is one which is able to replicate autonomously or integrated in the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

When the nucleic acid molecule that encodes any of the enzymes of the claimed invention is expressed in a cell, a variety of transcription control sequences (e.g., promoter/enhancer sequences) can be used to direct its expression. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (or RNA). That heterologous DNA (or RNA) is placed under operable control of transcriptional elements to permit the expression of the heterologous DNA in the host cell. In some embodiments two or more of the nucleic acids of the invention may be cloned into the same expression vector or plasmid.

A nucleic acid molecule or nucleic acid molecules that encode any of the enzymes associated with the invention can be introduced into a cell or cells using methods and techniques that are standard in the art. For example, nucleic acid molecules can be introduced by standard protocols such as transformation including chemical transformation and electroporation, transduction, particle bombardment, etc. Expressing a nucleic acid molecule(s) encoding an enzyme also may be accomplished by integrating the nucleic acid molecule into the genome. Nucleic acid molecule(s) can be integrated into a cell's genomic DNA using standard techniques well known in the art.

In some embodiments one or more genes associated with the invention is expressed recombinantly in a bacterial cell. Bacterial cells according to the invention can be cultured in media of any type (rich or minimal) and any composition. In some embodiments, the cells are cultured in LB media. As would be understood by one of ordinary skill in the art, routine optimization would allow for use of a variety of types of media. The selected medium can be supplemented with various additional components. Some non-limiting examples of supplemental components include glucose, antibiotics, IPTG, tetracycline or anhydro-tetracycline (aTc) for gene induction and ATCC Trace Mineral Supplement. Similarly, other aspects of the medium, and growth conditions of the cells of the invention may be optimized through routine experimentation. For example, pH and temperature are non-limiting examples of factors which can be optimized. In some embodiments the concentration and amount of a supplemental component may be optimized. In other embodiments, how often the media is supplemented with one or more supplemental components, and the amount of time that the media is cultured is optimized.

In some embodiments, the growth medium is adapted from Zawada and Swartz (2006) *Biotechnology and Bioengineering* 94(4):618 and comprises one or more of the following: deionized water, Swartz-Medium Stock, $MgSO_4$ Stock, Thiamine Stock, Trace Metals, Glucose, Vitamin stocks, Amino Acids Stock, BASF Industrol DF204 (antifoam), Chloramphenicol, Carbenicillin and preculture inoculum. Representative compositions of stock solutions are described further in the Examples section. Non-limiting examples of trace metals include: boric acid, cobalt chloride hexahydrate, cupric sulfate pentahydrate, manganese sulfate hydrate, sodium molybdate dihydrate, zinc sulfate heptahydrate and sulfuric acid.

Non-limiting examples of vitamins include: choline chloride, niacin (nicotinic acid), pyridoxine hydrochloride, riboflavin, panothenic acid hemicalcium salt, para-aminobenzoic acid (PABA), KOH, biotin, cyanocobalamin and folic acid dihydrate. Non-limiting examples of amino acids include: isoleucine, leucine, tryptophan and valine.

Cells associated with aspects of the invention can be cultured in a variety of devices, as would be understood by one of ordinary skill in the art. In some embodiments, cells are cultured in a bioreactor, such as a bioreactor provided by DASGIP AG, Julich Germany. In some embodiments, the bioreactor is a DASGIP AG bioreactor, Volume 4.0, May 2009, and bioreactor preparation is based on a DASGIP Control 4.0 User Manual. In some embodiments, a dissolved oxygen feeding strategy is followed, as described in the Examples section and as discussed further in Lee (1996) *Trends in Biotechnology,* 14(3):98-105.

In some embodiments, recombinant protein expression is under the control of the Lad promoter and is induced by addition of IPTG. It should be appreciated that other inducible promoters are also compatible with aspects of the invention. Cells can be harvested according to a variety of procedures, as would be familiar to one of ordinary skill in the art. For example, cells can be harvested by a peristaltic pump system, as described further in the Examples section.

According to aspects of the invention, a clarified lysate for cell-free production processes is generated. Cells can be lysed according to a variety of procedures, as would be familiar to one of ordinary skill in the art. In some embodiments, following harvesting, cells are lysed through a single pass homogenization at 20,000 psi using, for example, an Avestin EmulsiFlex-C3 High Pressure Homogenizer (Avestin, Inc., Ottawa, Ontario, Canada). In some embodiments, lysates are subjected to a second, and optionally further, homogenization passes. Whole cell lysates are then clarified through centrifugation, with clarified lysate being obtained in the harvest supernatant. In some embodiments, the cell-free reaction is initiated by the addition of substrates and cofactors to the clarified lysate. While representative procedures for cell culturing, harvest, and cell-free reactions are provided in the Examples section, it should be appreciated that optimization of such protocols can be achieved by one of ordinary skill in the art.

Pharmaceutical Compositions

The present invention also provides pharmaceutical compositions comprising a carbapenem, e.g., a compound of Formula (I), prepared by the above described cell-free system, and optionally a pharmaceutically acceptable excipient.

Pharmaceutically acceptable excipients include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in the formulation and/or manufacture of pharmaceutical compositions can be found, for example, in *Remington's Pharmaceutical Sciences*, Sixteenth Edition, E. W. Martin (Mack Publishing Co., Easton, Pa., 1980), and *Remington: The Science and Practice of Pharmacy,* $21^{st}$ Edition (Lippincott Williams & Wilkins, 2005).

Pharmaceutical compositions described herein can be prepared by any method known in the art of pharmacology. In general, such preparatory methods include the steps of bringing the compound of Formula (I) (the "active ingredient") into association with one or more excipients and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include, but are not limited to, antioxidants, chelating agents, antimicrobial preservatives, antifungal preservatives, alcohol preservatives, acidic preservatives, and other preservatives.

Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include, but are not limited to, ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include, but are not limited to, ethanol, polyethylene glycol, phenol, phenolic compounds, bisphenol, chlorobutanol, hydroxybenzoate, and phenylethyl alcohol.

Exemplary acidic preservatives include, but are not limited to, vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include pharmaceutically acceptable emulsions, microemulsions, solutions, suspensions, syrups and elixirs. In addition to the active ingredient, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments, for parenteral administration, the active ingredient is mixed with solubilizing agents such as Cremophor™ alcohols, oils, modified oils, glycols, polysorbates, cyclodextrins, polymers, and combinations thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Compositions for rectal or vaginal administration are typically suppositories which can be prepared by mixing the active ingredient with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert pharmaceutically acceptable excipient such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient only, or preferentially, in a certain part of the intestinal tract, optionally, in a delayed manner. Examples of embedding compositions which can be used include polymeric substances and waxes.

Dosage forms for topical and/or transdermal administration may include ointments, pastes, creams, lotions, gels, powders, solutions, sprays, inhalants and/or patches. Generally, the active ingredient is admixed under sterile conditions with a pharmaceutically acceptable excipient and/or any needed preservatives and/or buffers as can be required.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat.

Nos. 5,480,381; 5,599,302; 5,334,144; 5,993,412; 5,649, 912; 5,569,189; 5,704,911; 5,383,851; 5,893,397; 5,466, 220; 5,339,163; 5,312,335; 5,503,627; 5,064,413; 5,520, 639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

The formulations described herein as being useful for pulmonary delivery are also useful for intranasal delivery. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares. Formulations suitable for nasal administration may, for example, comprise from about as little as 0.1% (w/w) and as much as 100% (w/w) of the active ingredient, and may comprise one or more of the additional ingredients described herein.

A pharmaceutical composition of the invention can be prepared, packaged, and/or sold in a formulation suitable for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in *Remington: The Science and Practice of Pharmacy* 21$^{st}$ ed., Lippincott Williams & Wilkins, 2005.

Still further encompassed by the invention are pharmaceutical packs and/or kits. Pharmaceutical packs and/or kits provided may comprise a pharmaceutical composition and a container (e.g., a vial, ampoule, bottle, syringe, and/or dispenser package, or other suitable container). In some embodiments, the packs and/or kits may optionally further include a second container comprising a suitable pharmaceutical excipient for dilution or suspension of the pharmaceutical composition for preparation of administration to a subject. Optionally, instructions for use are additionally provided in such kits of the invention. Such instructions may provide, generally, for example, instructions for dosage and administration. In other embodiments, instructions may further provide additional detail relating to specialized instructions for particular containers and/or systems for administration. Still further, instructions may provide specialized instructions for use in conjunction and/or in combination with additional therapy.

Methods of Treatment and Administration

The present invention also provides a method of treating a bacterial infection comprising administering a therapeutically effective amount of a carbapenem, e.g., a compound of the Formula (I), prepared by the above described cell-free method, or a composition thereof, to a subject in need thereof.

A bacterial infection includes an infection from aerobic bacteria, anaerobic bacteria, Gram positive bacteria, well as Gram negative bacteria. Exemplary bacterial infections include, but are not limited to, an infection from Gram positive bacteria (e.g., a *Staphylococcus, Streptococcus, Clostridium, Listeria, Corynebacteria,* or *Bacillus* infection) or a Gram negative bacteria (e.g., an *E. coli, Salmonella, Shigella, Pseudomonas, Moraxella, Helicobacter, Stenotrophomonas, Bdellovibrio,* acetic acid bacteria, *Legionella, Wolbachia, Neisseria, Hemophilus,* or *Kelbsiella* infection). In certain embodiments, the bacterial infection is a *Pseudomonas* infection. In certain embodiments, the *Pseudomonas* infection is an infection from *Pseudomonas aeruginosa,* one of the leading agents of nosocomial infection.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, and/or turkeys.

As used herein, and unless otherwise specified, the terms "treat," "treating" and "treatment" contemplate an action that occurs while a subject is suffering from the infection, which reduces the severity of the infection, or retards or slows the progression of the infection.

As used herein, and unless otherwise specified, a "therapeutically effective amount" of a compound is an amount sufficient to provide a therapeutic benefit in the treatment or management of the infection, or to delay or minimize one or more symptoms associated with the infection. A therapeutically effective amount of a compound means an amount of therapeutic agent, alone or in combination with other therapies, which provides a therapeutic benefit in the treatment or management of the infection. The term "therapeutically effective amount" can encompass an amount that improves overall therapy, reduces or avoids symptoms or causes of the infection, or enhances the therapeutic efficacy of another therapeutic agent.

The compounds and compositions provided herein can be administered by any route, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, enteral, sublingual; by intratracheal instillation, bronchial instillation, and/or inhalation; and/or as an oral spray, nasal spray, and/or aerosol. Specifically contemplated routes are systemic intravenous injection, regional administration via blood and/or lymph supply, and/or oral administration. In general the most appropriate route of administration will depend upon a variety of factors including the nature of the agent (e.g., its stability in the environment of the gastrointestinal tract), the condition of the subject (e.g., whether the subject is able to tolerate oral administration), etc.

The compounds and compositions provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject will depend upon a variety of factors including the infection being treated and the severity of the infection; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, a therapeutically effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of an inventive compound per unit dosage form. It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

The compounds or compositions can be administered in combination with agents that improve their bioavailability, reduce and/or modify their metabolism, inhibit their excretion, and/or modify their distribution within the body. It will also be appreciated that therapy employed may achieve a desired effect for the same disorder (for example, a compound can be administered in combination with an anti-inflammatory, anti-anxiety and/or anti-depressive agent, etc.), and/or it may achieve different effects (e.g., control of adverse side-effects).

In one specific embodiment, a compound of Formula (I), e.g., imipenem, can be administered in combination with a dehydropeptidase inhibitor, such as cilastatin.

EXAMPLES

In order that the invention described herein may be more fully understood, the following examples are set forth. It should be understood that these examples are for illustrative purposes only and are not to be construed as limiting this invention in any manner.

Cell Free Synthesis of Carbapenems

The key enzymes required to catalyze an efficient bioconversion from economical substrates to the desired product are first expressed in a genetically engineered, rapidly-growing, strain of *E. coli* (see, e.g., enzymes listed in Tables 1 and 2). This aspect of the invention takes advantage of the compartmentalized structure of *E. coli* to produce most of the desired pathway enzymes in the cytoplasm, with the key entry enzyme (i.e., the first enzyme in the committed metabolic pathway required for the product) targeted for production in the periplasm. See, e.g., PCT publication WO 2010/074760; incorporated herein by reference. This ensures that the pathway is not activated (or is minimally activated) in the intact organism, maintaining robust growth and metabolic health. Cells are grown rapidly to relatively high cell density in a fermentor designed for high rates of oxygen delivery and heat removal. Prior to harvesting, the culture is induced to produce the overexpressed proteins targeted to both the cytoplasm and periplasm.

Exemplary Cell-Free Synthesis of Imipenem. Pathway steps a-f catalyze the formation of heterologous pathway substrates glutamate semialdehyde and ethylmalonyl-coenzyme A from glutamate and glucose and involve either native *E. coli* enzymes (steps a, b, c, and e), or enzymes that have been shown to be functional in *E. coli* (steps d, f). Steps a and b catalyze the formation glutamate semialdehyde from glutamate. Step c includes the glycolytic pathway and supplies acetyl-coenzyme A from glucose. Steps d-f are required for the production of ethyl malonyl-coenzyme A from acetyl-coenzyme A ($R^2$=—$CH_2CH_3$). An acetyl-coenzyme A acetyltransferase (step d) and Crotonyl-coenzyme A reductase (step f) from *Rhodobacter sphaeroides* were shown to catalyze the formation of acetoacetyl-coenzyme A and ethylmalonyl-coenzyme A, respectively, from acetyl-coenzyme A, Crotonyl-coenzyme A and $CO_2$ in *E. coli*. See, e.g., Sato et al., *J. Biosci. Bioeng.* (2007) 103:38-44; Erb et al., *Proc. Natl. Acad. Sci. USA* (2007) 104:10631-10636; Erb et al., *Proc. Natl. Acad. Sci. USA* (2009) 106:8871-8876. Additionally Crotonyl-coenzyme A can be produced in *E. coli* from acetoacetyl-coenzyme A (step e) using native *E. coli* FadB or other heterologous enzymes. See, e.g., Atsumi et al., *Metab. Eng.* (2008) 10:305-311. The pathway to imipenem from glutamate semialdehyde and ethylmalonyl coenzyme A (steps 1-5) combines enzymes from both thienamycin and carbapenem biosynthesis pathways. See, e.g., Williamson et al., *J Biol Chem* (1985) 260:4637-4647; Stapon et al., *J. Am. Chem. Soc.* (2003) 125:15746-15747; Rodriguez et al., *J Antibiot* (2010) 63:135-138; Rodriguez et al., *Mol Microbiol* (2008) 69:633-645; and references cited in Table 2.

Other carbapenem compounds are contemplated following the above description as a guide, see, e.g., FIGS. 9A-9H. One particular carbapenem intermediate contemplated may be provided from glucose and glycine (see the combination of FIGS. 3-5A and 9D). The key steps include production of 3-hydroxyglutamate from glycine and malonic semialdehyde using threonine aldolase and the formation of the carbapenem core from 3-hydroxyglutamate semialdehyde and ethylmalonyl-CoA. See, e.g., Riva et al., *Tetrahedron* (2008) 64:5079.

Attachment of the C2-Side Chain

In the *S. cattleya* pathway to thienamycin, the attachment of pantetheine to the carbapenem nucleus at the C-2 position is putatively catalyzed by ThnV. See, e.g., Nunez et al., *Chem. Biol.* (2003) 10:301-311. ThnV has been proposed to catalyze the condensation of a thiol-containing side chain at the C-2 position of the carbapenem nucleus based on sequence similarity to glutathione transferase. This hypothesis can be tested by expressing the thnV gene (codon-optimized for expression in *E. coli*) in *E. coli* and assessing the ability of the heterologous protein to conjugate pantetheine to the carbapenem nucleus ($R^2$=$CH_2CH_3$). The sequence of the gene encoding ThnV (obtained from EMBL accession number AJ421798) can be chemically synthesized and can be modified to include both a C-term and N-term 6×His tag for purification via immobilized metal affinity chromatography. The thnV gene can be codon optimized for expression in *E. coli* due to the high (>70%) GC content of the *S. cattleya* genome. Synthetic genes can be subcloned into expression vectors conferring C-term and N-term 6×His tags. The pDuet family of vectors could be used for T7-based expression of synthesized genes due to commercial availability (Novagen, Inc.), ease of subcloning, and tight control over gene expression. Expression level can be modified through use of varying levels of isopropyl β-D-1-thiogalactopyranoside (IPTG), as well as through use of copy number variation among different vectors (the pDuet vectors all share the same expression machinery, but vary in copy number over a range of approximately 10 to >100 copies/cell). The *E. coli* strain BL21(DE3) can be transformed with plasmids containing the subcloned genes, and transformants can be selected using appropriate antibiotics. The culture can be grown to intermediate optical density ($OD_{600}$ 0.5-1) in rich defined media prior to expression induction with 0.1-1 mM IPTG. Cells can then be harvested and concentrated prior to lysis using a high pressure homogenizer. The expression of full-length protein can be confirmed by denaturing protein gel electrophoresis with appropriate standards.

Figure 6B:
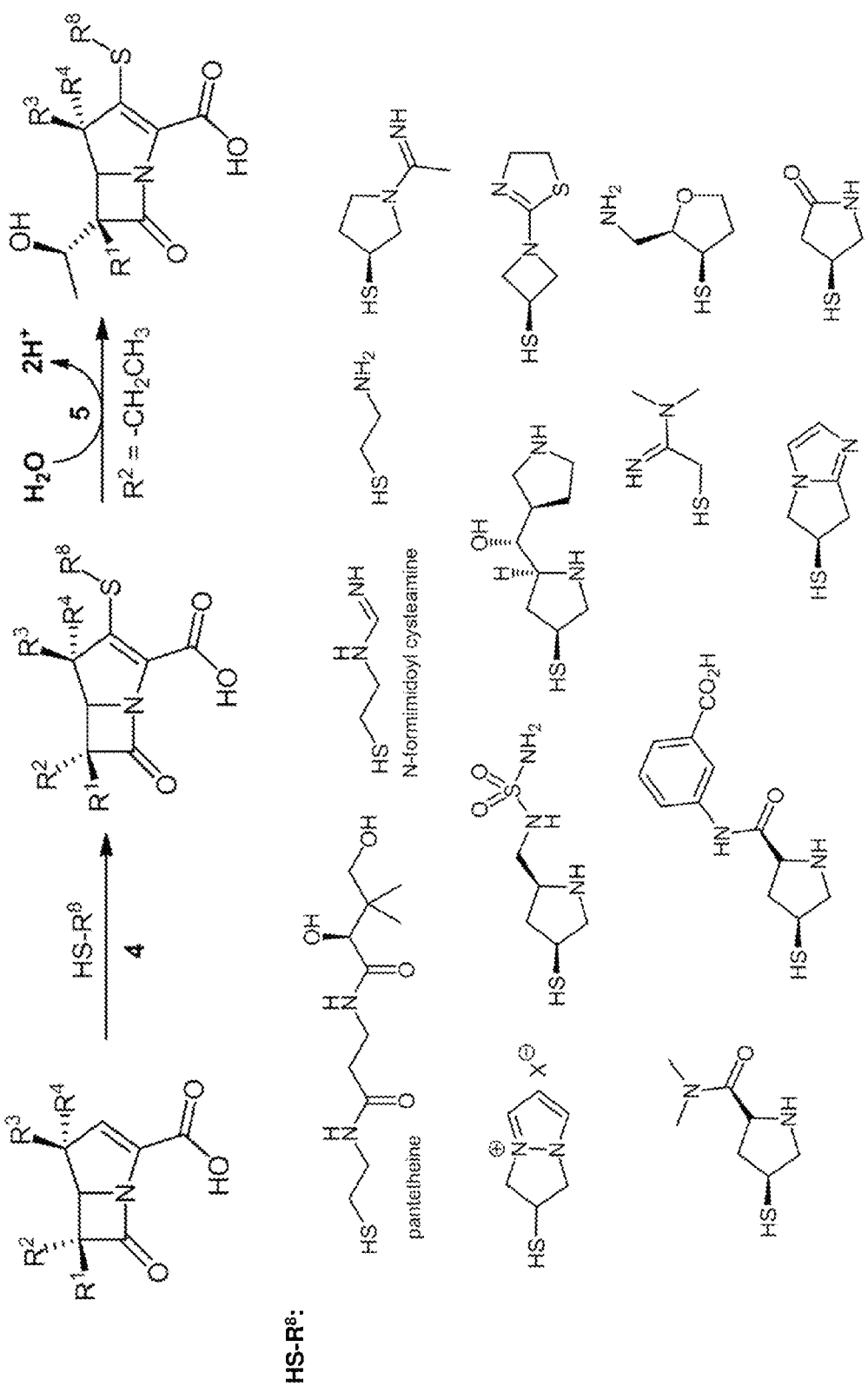
FIG. 6B depicts the enzymatic attachment of a C2 side chain, and subsequent optional enzymatic hydroxylation of the C6 ethyl group to provide an exemplary carbapenem (steps 4-5).
Figure 7:
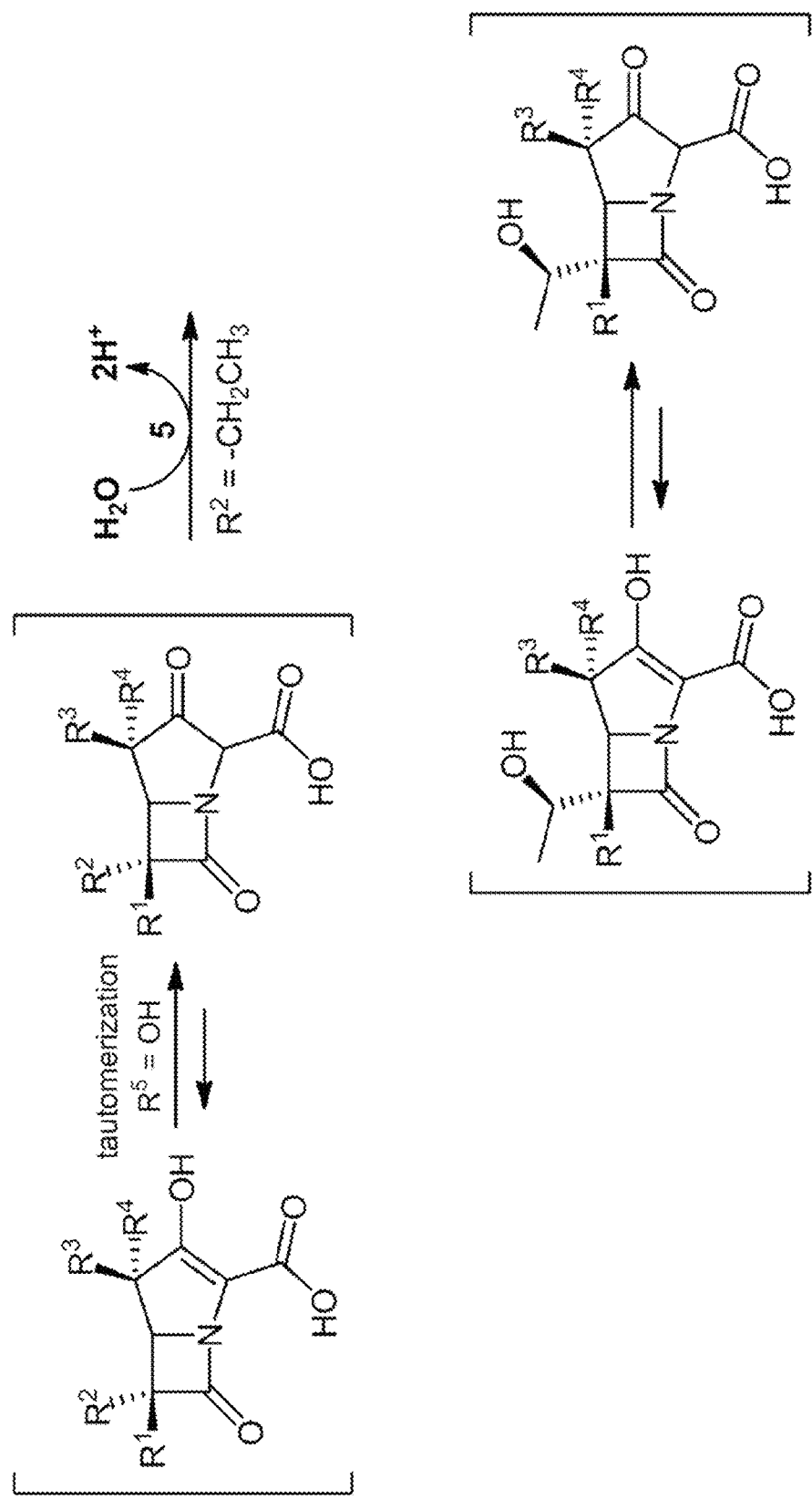
FIG. 7 depicts the enol-keto tautomeration of Formula (I) when $R^5$ is —OH, and subsequent optional enzymatic hydroxylation of the C6 ethyl group to provide an exemplary carbapenem (step 5).

A C2 group (e.g., an —$SR^8$ group) can be attached, either chemically or enzymatically, via Michael addition of the corresponding thiol. Exemplary C2 groups include, but are not limited to, pantetheine and N-formimidoyl cysteamine, as well as others described herein (see, e.g., FIG. 6). Pantetheine can be prepared as described in Mandel et al., *Org Lett* (2004) 6:4801-4803. N-formimidoyl cysteamine can be prepared as described in U.S. Pat. Nos. 4,292,436 and 4,329,481. The C2-C3 double bond can be reintroduced by oxidation in the presence of methylene dichloride (see Bateson supra). The C2 group can also be attached via trapping of the enol form, followed by Michael addition and subsequent elimination. See, e.g., Rabasseda et al., *Drugs Fut* (1994) 19:631 and US 20090312539.

Chemical Synthesis of Genes

Genes coding for enzymes listed in Table 3 can be chemically synthesized with codon-optimization for expression in *E. coli*. Genes can be synthesized with both C- and N-terminal 6×His tags for purification of expressed protein. Enzymes from *P. carotovorum* (CarB, CarA, CarC) and homologs from *S. cattleya* (ThnE, ThnM, ThnG) can be tested for each enzymatic step 1-3.

TABLE 3

List of enzymes expressed/purified from chemically-synthesized genes

| Step | Enzyme | Description | Organism | GenBank |
|---|---|---|---|---|
| 1 | CarB | carboxymethylproline synthase | *P. carotovorum* | AAD38230.1 |
| 1 | ThnE | carboxymethylproline synthase | *S. cattleya* | CAD18973.1 |
| 2 | CarA | carbapenam synthetase | *P. carotovorum* | AAD38229.1 |
| 2 | ThnM | b-lactam synthetase | *S. cattleya* | CAD18981.1 |
| 3 | CarC | carbapenem synthase | *P. carotovorum* | AAD38231.1 |
| 3 | ThnG | putative carbapenem synthase | *S. cattleya* | CAD18975.1 |

Chemical Synthesis of Substrates

Native carbapenem ($R^2$=H), 6-methyl carbapenem ($R^2$=$CH_3$), and 6-ethyl carbapenem ($R^2$=$CH_2CH_3$) substrates have been prepared from 4-allyl-azatidin-2one, 4-allyl-3-methylazatidin-2one and 4-allyl-3-ethylazatidin-2one, respectively. See, e.g., Bateson et al., *J. Chem. Soc. Perkin Trans.* 1 (1990) 1793-1801.

Table 4 lists compounds to be chemically synthesized for testing enzyme activity on non-native substrates. Other necessary substrates, including malonyl-coenzyme A, ATP, and 2-ketoglutarate, will be obtained from commercial suppliers.

TABLE 4

List of custom-synthesized compounds

| | Compound | Description | Structure |
|---|---|---|---|
| a | (S)-2-amino-5-oxopentanoic acid (glutamate semialdehyde) | Native substrate of CarB (Step 1) | 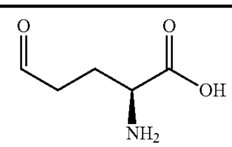 |
| b | (2S)-2-amino-3-hydroxy-5-oxopentanoic acid (3-hydroxy-glutamate semialdehyde) | Desired substrate of CarB/ThnE (Step 1) | 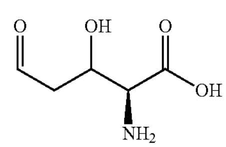 |
| c | Ethylmalonyl-coenzyme A | Desired substrate of CarB/ThnE (Step 1) | 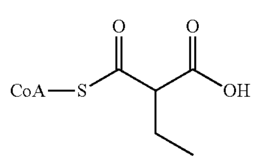 |
| d | (5R)-6-ethyl-3,7-dioxo-1-azabicyclo[3.2.0]-heptane-2-carboxylic acid | Desired product of CarC/ThnG (Step 3) with CarB/ThnE substrates b, c | 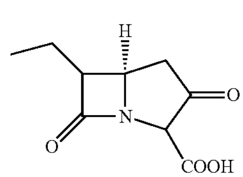 |

Upon receipt of d, initial tests will be performed to assess the antibiotic activity of the compound. Tests of antibiotic activity will consist of spotting varying concentrations of d on plates infused with a β-lactam sensitive strain of *E. coli* (e.g., SC12155, X580). Appearance of zones of growth inhibition will confirm antibiotic activity of d, enabling simple and rapid assay for production of d in coupled enzyme reactions initiated with desired substrates b and c. See, e.g., Sleeman and Schofield, *J. Biol. Chem.* (2004) 279:6730. If no antibiotic activity is observed, LC/MS analysis will be used to verify enzyme activities on non-native substrates.

Upon receipt of a and malonyl-CoA, native activity of purified CarB, CarA, and CarC will be demonstrated by assessing the antibiotic activity of the coupled CarB/CarA/CarC reaction. See, e.g., Sleeman and Schofield, *J. Biol. Chem.* (2004) 279:6730. Both N- and C-terminal 6×His versions of each protein will be tested together with Thn homologs of CarB, CarA, and CarC (ThnE, ThnM, ThnG).

Once the native activity of CarB, CarA, and CarC enzymes (and Thn homologs) has been demonstrated, the coupled CarB/CarA/CarC reaction will be tested with substrates b and c. Both antibiosis (if d possesses antibiotic activity) and LC/MS analysis will be used to verify production of d.

Testing of Transferase Enzymes on Chemical Substrates

Biochemical reactions will be prepared with both purified ThnV (using immobilized nickel affinity resin column) as well as high density ($OD_{600}$~100) crude lysate. Reactions will contain chemically synthesized pantetheine, N-formimidoyl cysteamine, and carbapenem substrates at concentrations ranging from 1-5 mM in 50 mM Tris-HCl, pH 7.5. The requirement of a metal cofactor for enzyme activity will be determined by addition of 1-5 mM divalent ($Mg^{2+}$, $Mn^{2+}$, $Cu^{2+}$, $Fe^{2+}$, $Zn^{2+}$, $Ca^{2+}$, and $Co^{2+}$) and monovalent ($K^+$, $Na^+$, and $Li^+$) metals. Reactions will be incubated at 37° C. for 3-15 minutes; e.g., 1 g/L-h imipenem productivity is equivalent to 0.05 mM imipenem/min requiring a reaction time of 10 mM for 50% substrate conversion. Incorporation of pantetheine or N-formimidoyl cysteamine to each carbapenem nucleus will be determined by the increase in the respective product peak in reverse phase high performance liquid chromatography (HPLC) with UV detection at 300 nm, the absorbance maximum of the common carbapenem chromophore. See, e.g., Bodner et al., *J. Am. Chem. Soc.* (2010) 132:12-13; Myers et al., *Antimicrob. Agents. Chemother.* (1984) 26:78-81. A 5% level of incorporation of the non-native N-formimidoyl cysteamine side chain indicates that protein evolution techniques can be employed to obtain higher yields of the desired product. Myers et al (supra) reports the minimum detection limit of carbapenem derivatives via HPLC is 1 µM, well below the minimum target of 5% of 1 mM, or 50 µM. The fraction corresponding to the product peak will be collected and further verified using electrospray ionization mass spectrometry (ESI-MS).

This project will yield a new, low-cost manufacturing platform that may also facilitate production of novel carbapenem antibiotics through use of heterologous enzymes as well as enzymes engineered to efficiently accept non-native substrates. See, e.g., Dietrich et al., *ACS Chem Biol* (2009) 4:261-267; Tracewell et al., *Curr Opin Chem Biol* (2009) 13:3-9.

Methods for Cell Growth

A seed culture is prepared by inoculating 100 ml of LB with the appropriate antibiotic(s) with 1 ml of a thawed working stock of the engineered strain. The seed culture is incubated 300 rpm, 37° C. for 7 h. The seed culture is used to inoculate 1 L of a defined growth medium (e.g., as described in Zawada and Swartz, Biotechnology and Bioengineering 94(4):618, 2006). Starting optical density (OD) is 0.03. A DO-based feed strategy is used as described in the table below; feed solution contains 500 mg/ml glucose, 0.15% (v/v) BASF Industrol DF204 antifoam, and 7.69 ml 1 M $MgSO_4$ per 200 ml feed. The DO-based feed strategy is based on the following reference: Lee, S Y, 1996. High cell-density culture of Escherichia coli. Trends in Biotechnology. 14, 3, 98-105. Protein expression is induced for 1 h by adding 0.8 mM IPTG when optical density reaches 10-20. Prior to cell harvest, the temperature of the culture is reduced from 37 to 10° C. over 0.25-0.5 h while maintaining agitation, aeration and feeding.

TABLE 5

Fermentation process parameters

| | |
|---|---|
| Temperature | 37° C. |
| DO setpoint | 30%; controller settings P = 0.20, Ti = 300 s |
| DO cascade | controller cascade 0-50%->500-1100 rpm; 50-100%->21-60% $O_2$ |
| pH setpoint | 7; autoreset Yi (unchecked) |
| Aeration | 60 L/h (1 vvm) |
| Agitation | 500-1100 rpm (cascade) |
| Pump B | $NH_4OH$ 15% (7.4M) |
| Pump C | Feed solution; DO-based feed strategy:Flow rate @ 40 ml/h to feed 6 ml shots; Trigger ON:DO >55%; Trigger OFF:DO <40% |

Methods for Preparation of Cell Lysate

Approximately 10° C. culture is harvested by centrifugation at 8000×g for 30-60 min at 4° C. Cell pellet is resuspended to optical density 100-250 in 10-50 mM potassium phosphate, pH 8.5.

When optimal levels of the induced enzymes have accumulated, the culture is concentrated and lysed, releasing the key periplasmically-expressed enzyme(s). An optimized chemical environment will activate respiration catalyzed by inner membrane vesicles formed during cell lysis. See, e.g., Jewett et al., Mol. Syst. Biol. (2008) 4:220. This will provide a plentiful supply of ATP for the synthetic pathway and will also remove excess reducing equivalents to recycle $NAD^+$ and/or $NADP^+$. Cells are lysed by two passes through a homogenizer (e.g., an Avestin EmulsiFlex-C3 High Pressure Homogenizer) at 20,000 psi. Lysate is collected in a sterile flask on wet ice. If necessary, lysate is clarified through centrifugation at 25,000×g for 30 min at 4° C. The supernatant retained as the clarified lysate.

Methods for Preparation of the Cell-Free Reaction

Cell-free reactions take place in a bioreactor using settings outlined in the table below. Lysate or clarified lysate is warmed to 37° C. in the reactor and dissolved oxygen levels are equilibrated. The cell-free reaction is initiated with addition of pathway substrates and key cofactors.

TABLE 6

Cell-free reaction process parameters

| | |
|---|---|
| Temperature | 37° C. |
| DO setpoint | 80%; controller settings P = 0.50, Ti = 300 s |
| DO cascade | controller cascade 1200 rpm; 0-100%->21-100% $O_2$ |
| pH setpoint | 7; autoreset Yi (checked); controller settings P = 10, Ti = 2400 s |
| Aeration | 10 L/h (2.2 vvm) |

TABLE 6-continued

Cell-free reaction process parameters

| | |
|---|---|
| Agitation | 1200 rpm (cascade) |
| Pump A | $H_2SO_4$, 5% (1.9N) |
| Pump B | KOH, 2N |
| Pump C | Substrate |
| Pump D | Substrate |

General Procedures for Examples 1 to 4

Several strains were created, each enabling the inducible over-expression of one, or more, of the following enzymes: ProB, ProA, CarB, CarA, CarC, and PutA. The carB/A/C genes of P. carotovorum were codon-optimized for expression in E. coli, while the proB/A and putA genes were amplified directly from the E. coli MG1655 genome. Strains were grown in to mid-log phase at 37° C., induced for 1-5 hours, pelleted, concentrated 10-20× upon resuspension, and lysed using a cell homogenizer. Lysate was clarified via centrifugation, to remove cell debris, and a single lysate, or mix of lysates, was used to provide the necessary activities. Reactions (0.1-1 mL) were maintained at 37° C. for 1-3 hours prior to ethanol quench. Modified diacids, CoA substrates, proline and other cofactors (ATP, NADPH, 2-ketoglutarate) were added to the reactions when required. LCMSMS was used for analysis of reaction intermediates and products.

Example 1

Production of Substituted Carboxy-Methylproline Molecules from Substituted Glutamate and Malonyl-CoA or Ethylmalonyl-CoA BL21(DE3) strain containing plasmids expressing ProB, ProA, and CarB was grown to high cell density, lysed, and cell debris were removed via centrifugation. Clarified lysate (30% final reaction volume, 3.9 mg/ml protein) was incubated with 5 mM of one of the following: glutamate, 4-hydroxy-glutamate, or 4-methyl-glutamate together with 1.6 mM ethylmalonyl-CoA, 3 mM ATP, 3 mM NADPH, and 2 mM $MgCl_2$ for 60 min at 37° C. Reactions without substrates were included as controls. Ethanol-quenched reactions were analyzed by LCMSMS using the method below:

| | |
|---|---|
| Column | Phenomenex Synergi Polar RP, 250 × 4.6 mm, 4 mm |
| Mobile Phase | A:10 mM ammonium acetate in water, pH 6.6<br>B:acetonitrile |
| Flow | 75/25 A/B, isocratic, 0.75 ml/min |
| Injection vol. | 0.02 ml of reaction mix |
| Detection | MS/MS, negative mode |

Figure 10:
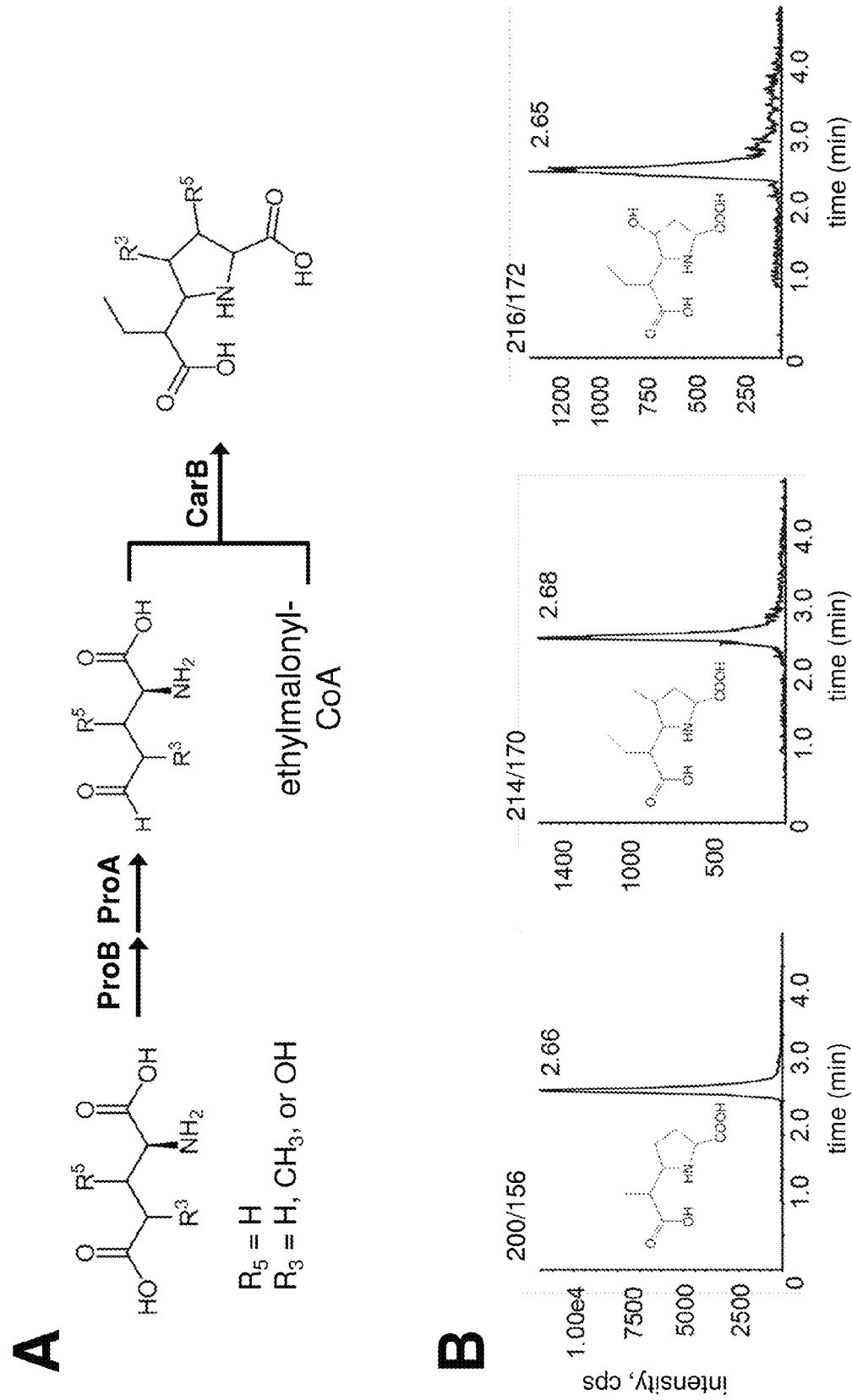
FIG. 10 depicts production of a substituted carboxymethyl proline (CMP) from a substituted glutamate and ethylmalonyl-CoA in lysate containing ProB, ProA, and CarB activities (A) and LC/MS/MS characterization (B).

Native carboxymethyl prolines and a number of substituted carboxymethyl prolines were identified by LCMSMS in the negative mode, through the loss of a carboxyl group (−44). Data are illustrated in FIG. 10.

| Substrates | MS/MS Transition (negative mode) |
|---|---|
| Glutamate + Malonyl CoA | 172/128 |
| 2S,4S 4-Methyl Glutamate + Malonyl CoA | 186/142 |
| 2S,4R 4-Methyl Glutamate + Malonyl CoA | 186/142 |
| 4-Hydroxy Glutamate + Malonyl CoA | 188/144 |
| 4-Hydroxy Glutamate + Ethyl Malonyl CoA | 216/172 |

-continued

| Substrates | MS/MS Transition (negative mode) |
|---|---|
| Glutamate + Ethyl Malonyl CoA | 200/156 |
| 2S,4R 4-Methyl Glutamate + Ethyl Malonyl CoA | 214/170 |
| 2S,3S-3-OH Glutamate (trans) + Malonyl CoA | 188/144 |

Example 2

Substituted Carbapenam Production from Substituted Glutamate and Malonyl-CoA in Lysate Containing ProB, ProA, CarB, and CarA Activities The reactions described in Example 1 were concentrated 4× and combined with 5 µM CarA protein, 6 mM ATP, 2 mM MgCl$_2$ in 10 mM Tris pH 9 at 37° C. for 60 min. Reactions without substrates were included as controls. Ethanol-quenched reactions were analyzed by LCMSMS using the method below:

| | |
|---|---|
| Column | Phenomenex Synergi Polar RP, 250 × 4.6 mm, 4 mm |
| Mobile Phase | 0.1% (v/v) formic acid in water |
| | 0.1% (v/v) formic acid in acetonitrile |
| Flow | 75/25 A/B, isocratic, 0.75 ml/min |
| Injection volume | 0.02 ml of reaction mix |
| Detection | MS/MS, negative mode |

Figure 11:
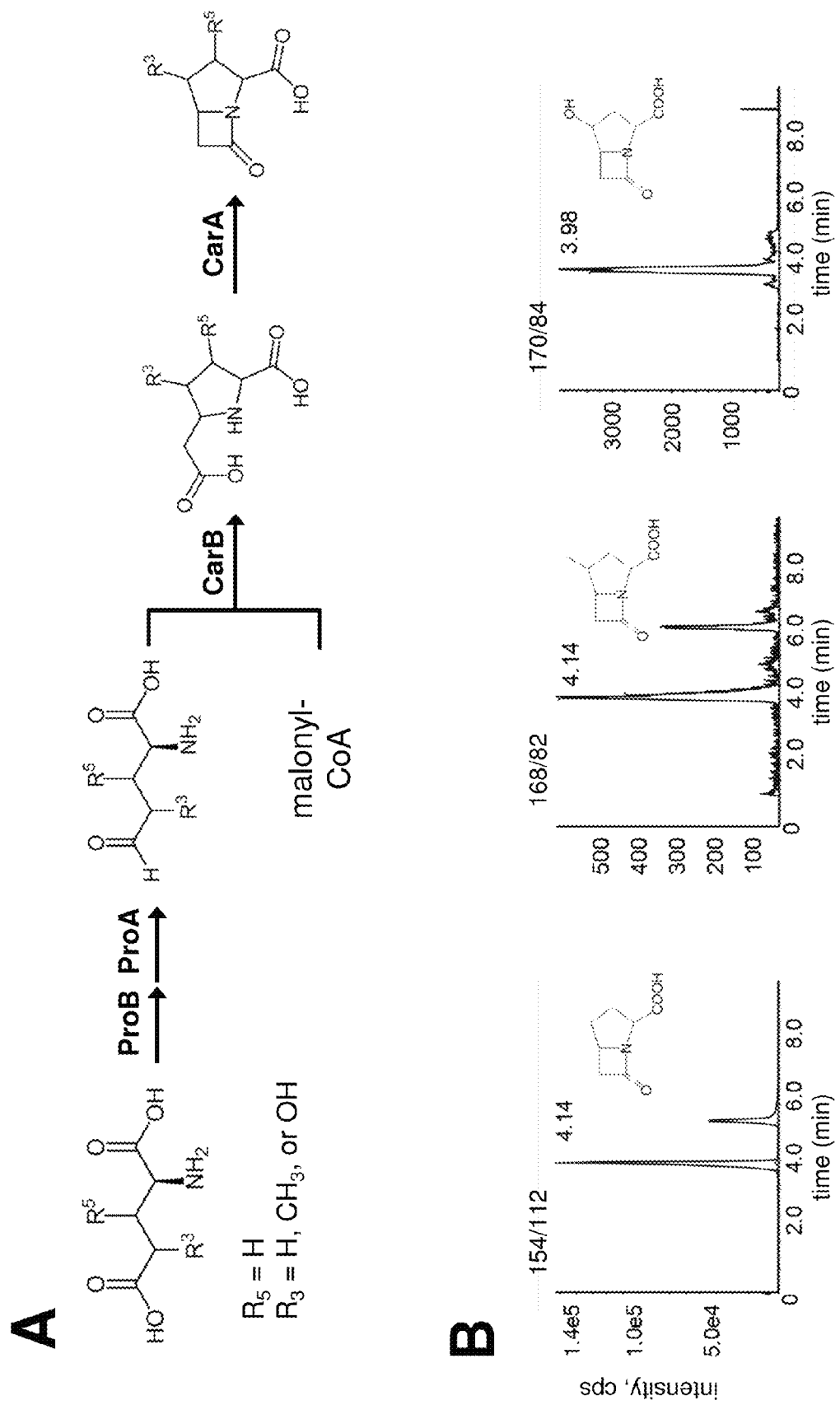
FIG. 11 depicts substituted carbapenam production from substituted glutamate and malonyl-CoA in a lysate containing ProB, ProA, CarB, and CarA activities (A) and LC/MS/MS characterization (B).

Carbapenams were identified by MS/MS transitions of 154/112 (native carbapenam) 168/82 (4-methyl carbapenam), and 170/84 (4-hydroxy carbapenam) with the product ion representing loss of ketene (−42) with or without decarboxylation (−44) of the five membered ring. Data are illustrated in FIG. 11.

Example 3

Figure 12:
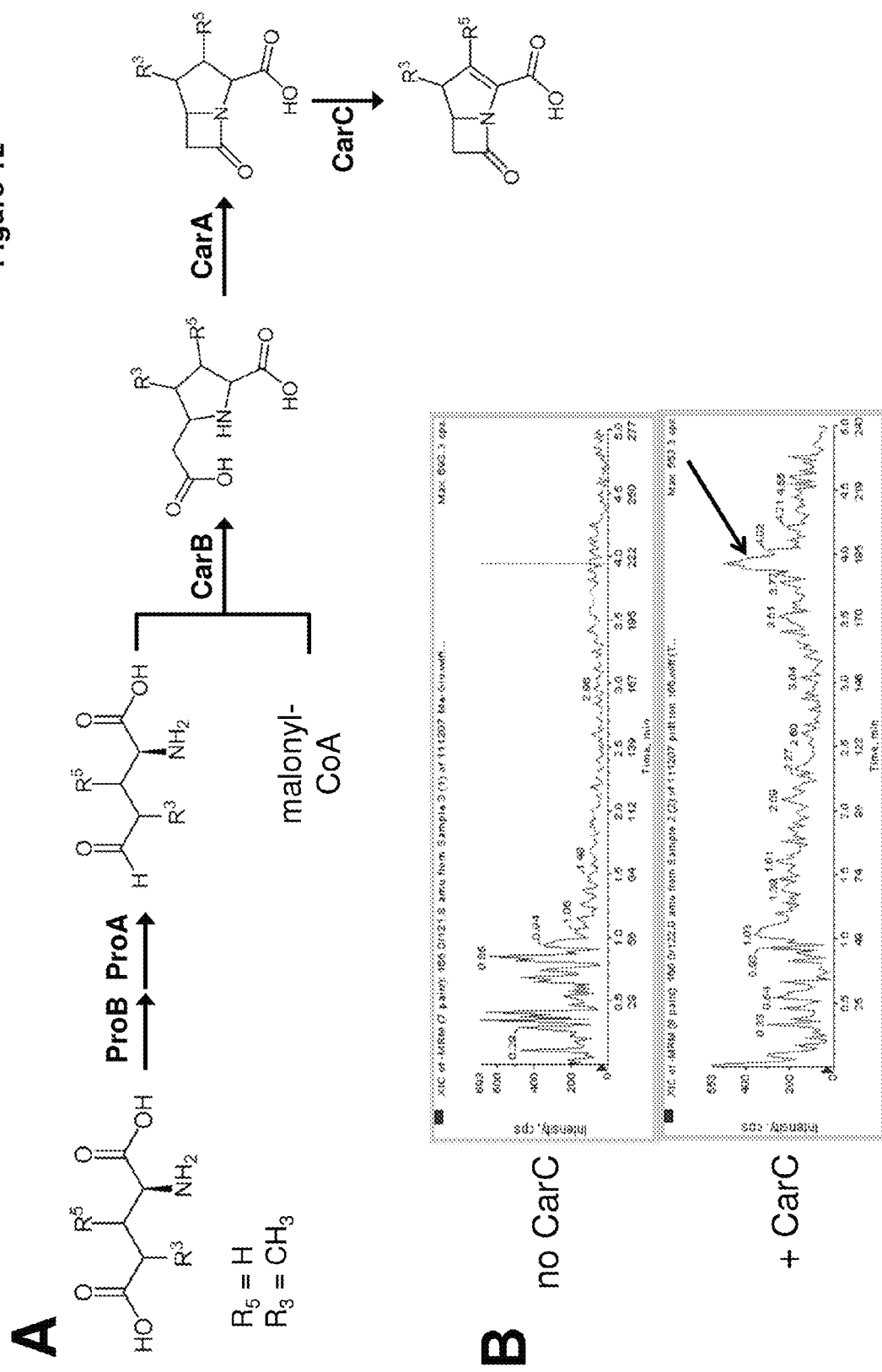
FIG. 12 depicts substituted carbapenem production from substituted glutamate and malonyl-CoA in a lysate containing ProB, ProA, CarB, CarA, and CarC activities (A) and LC/MS/MS characterization (B).
Figure 13A:
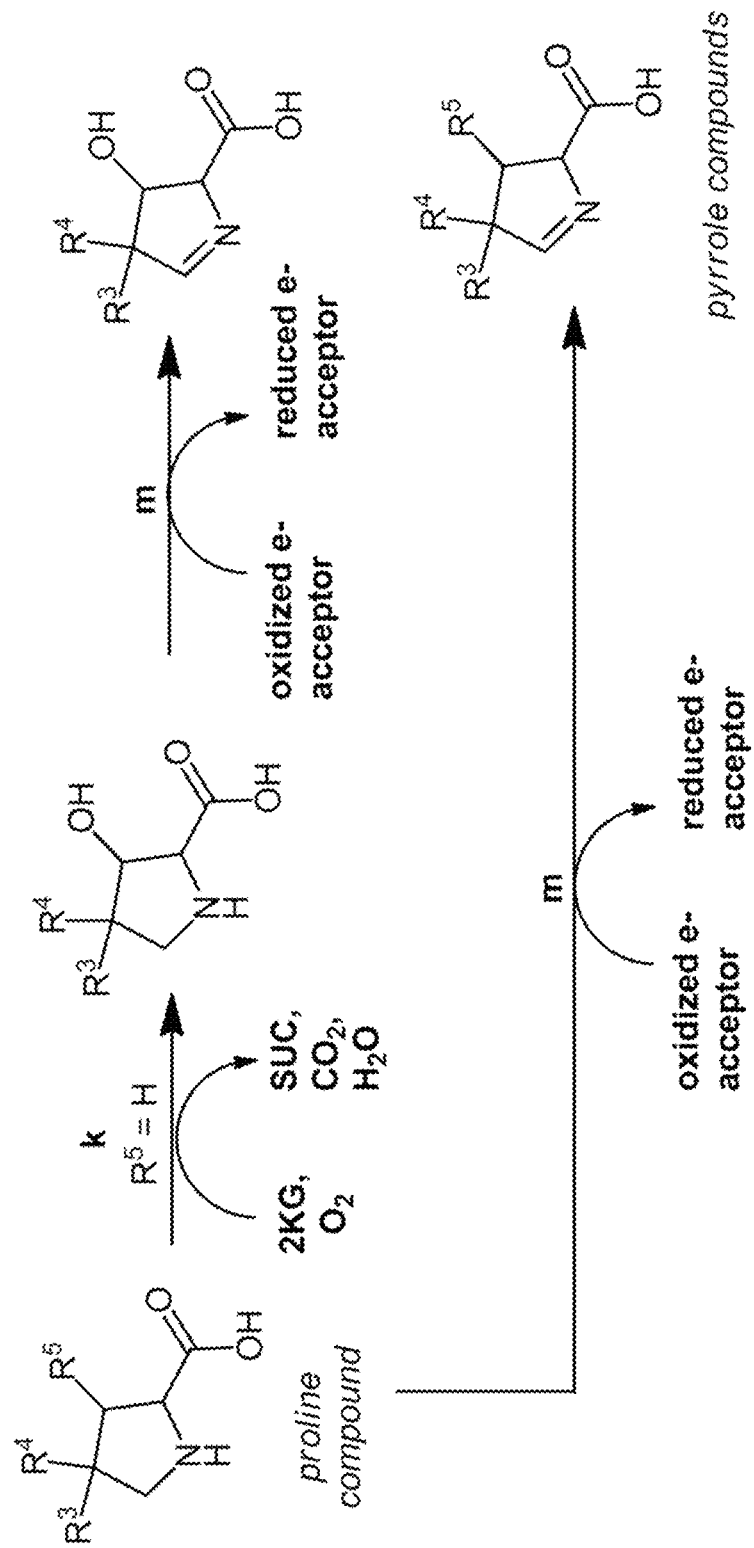
FIG. 13A depicts production of a pyrrole CarB substrate from a proline compound via contact with a proline 3-hydroxylase (step k) and/or a proline oxidase (step m).
Figure 13B:
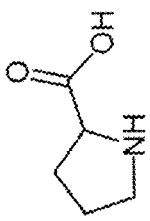
FIG. 13B depicts exemplary pyrrole compounds which may be produced from proline compounds following the method depicted in FIG. 13A.
Figure 13B:
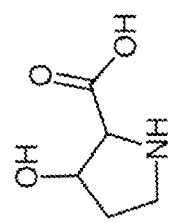
Figure 13B:
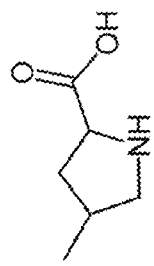
Figure 13B:
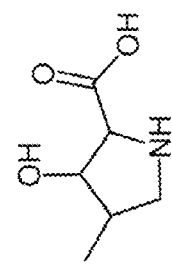
Figure 13B:
Figure 13B:
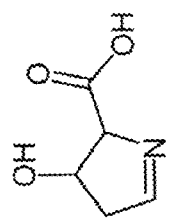
Figure 13B:
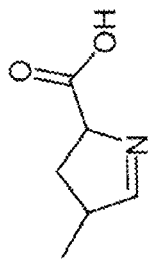
Figure 13B:
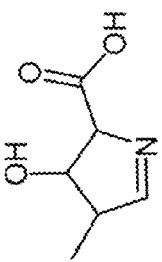
Figure 13C:
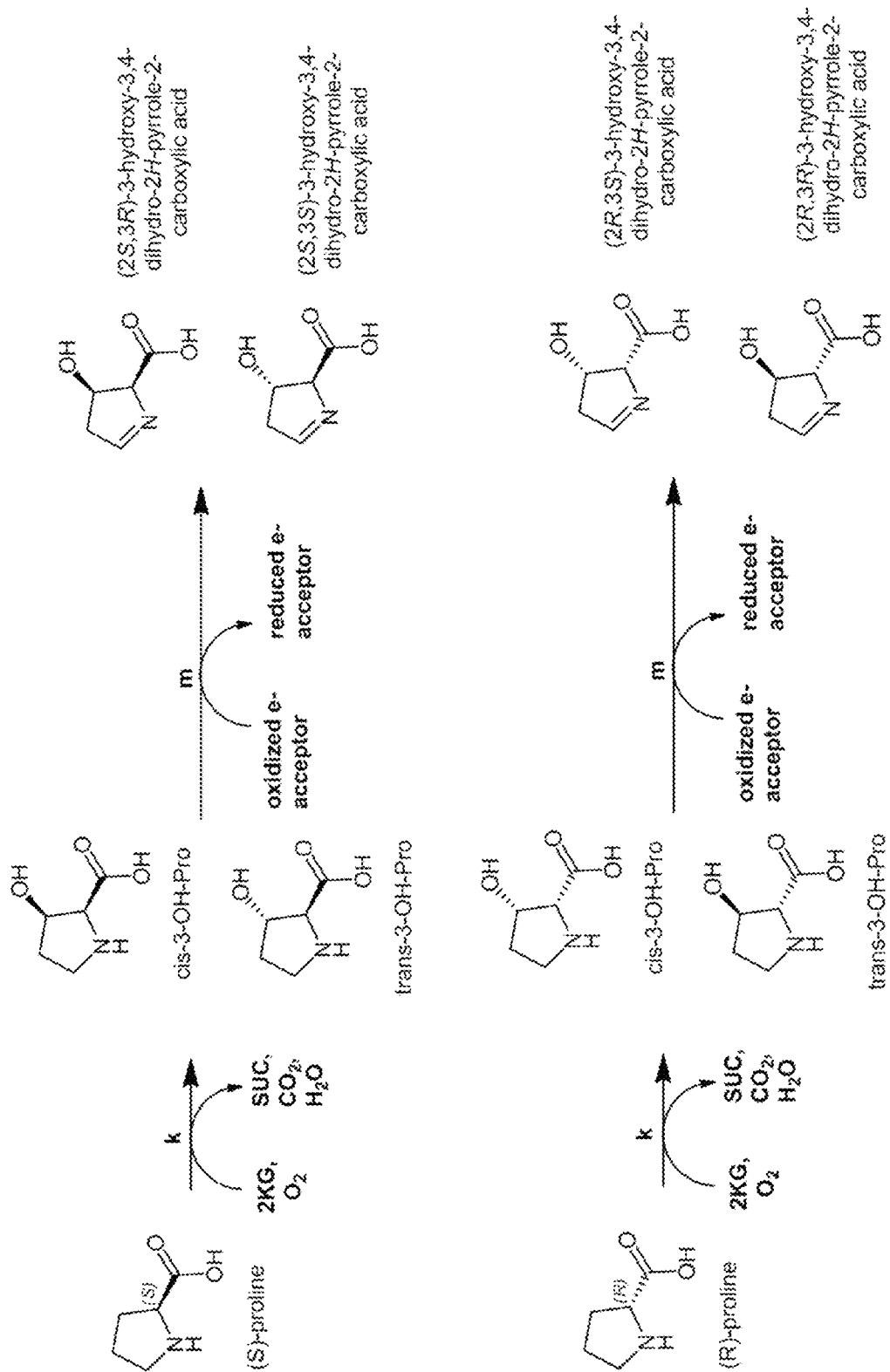
FIG. 13C depicts the enzymatic synthesis of cis and trans 3-hydroxy-3,4-dihydro-2H-pyrrole-2-carboxylic acid from (S)- and (R)-proline via contact with a proline 3-hydroxylase (step k) and a proline oxidase (step m).
Figure 13D:
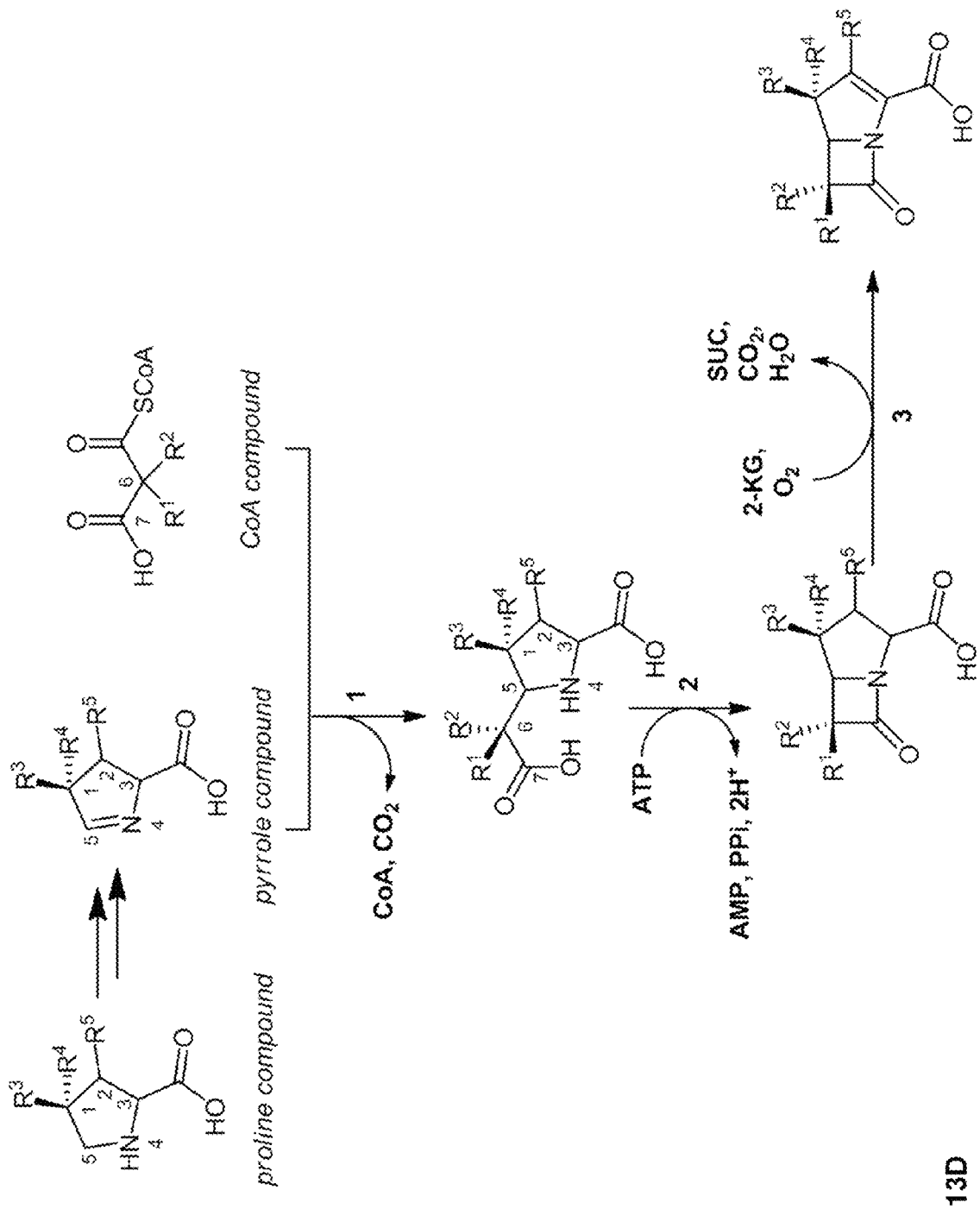
FIG. 13D depicts the enzymatic production of a carbapenem from a pyrrole compound and a coenzyme A compound. The process utilizes enzymes from both thienamycin and/or carbapenem biosynthetic pathways (steps 1-3). The *E. coli* may be engineered to produce the key-entry enzyme carboxymethyl-Pro synthase (CarB, ThnE, or isozyme thereof) in the periplasmic space of the *E. coli*.

Production of Substituted Carbapenem from Substituted Glutamate and Malonyl-CoA in Lysate Containing ProB, ProA, CarB, CarA, and CarC Activities 15 mM 4-methyl-glutamate and 8 mM malonyl CoA were added to a cell free extract from a strain expressing ProB, ProA, CarB and CarA in the presence of 2.5 mM NADPH, 10 mM ATP and 6.7 mM MgCl$_2$ in 50 mM Tris pH 8.5. The reaction was allowed to proceed for 2 hours at 37° C. to produce methylated carbapenam that was detected by LCMSMS (168/125.9). The carbapenam producing reaction was diluted two-fold in 8 mM alpha-ketoglutarate, 1 mM ascorbate, 1 mM ferrous ammonium sulfate and 1.6 mg/ml CarC. After 1 hour at 37° C. the reaction was quenched with an equal volume of ethanol and concentrated down to its original volume by speed vac centrifugation. The level of remaining methylated carbapenam and the appearance of methylated carbapenem were determined by LCMSMS. Methylated carbapenem was detected at 166/122 (decarboxylated) and 184/140 (hydrolyzed and then decarboxylated). Data are illustrated in FIG. 12.

Example 4

Figure 14:
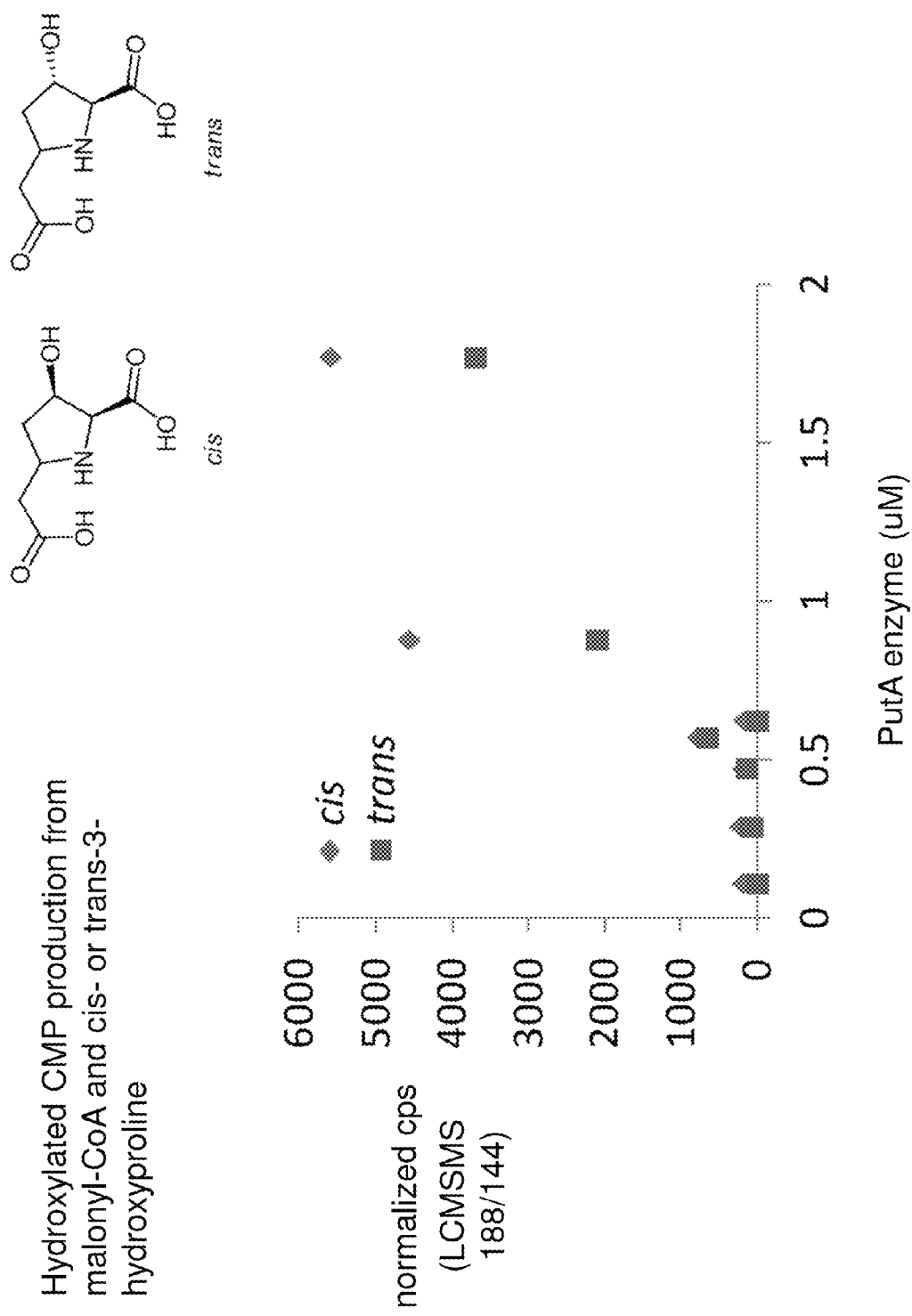
FIG. 14 depicts production of a hydroxlated carboxymethyl proline (CMP) compound from cis- or trans-3-hydroxy-proline and malonyl-CoA in lysate containing varying amounts of proline oxidase PutA (*E. coli*) and CarB (*P. carotovorum*).

Production of Substituted Carboxymethyl Proline from 3-Hydroxyproline and Malonyl-CoA in Lysate Containing PutA (E. coli Proline Oxidase) and CarB BL21(DE3) strain carrying a plasmid enabling IPTG-inducible expression of CarB was grown in 1 L LB to 0.5<OD<1 and induced (0.8 mM IPTG) for 1 h at 37° C. a BL21(DE3) strain carrying an empty vector was grown in 5 L of M9+10 g/L proline until reaching a max OD~0.4. Cells were harvested, washed in 100 mL resuspension medium (100 mM Tris-HCl, pH 8) and cell pellets were stored at −80° C. prior to lysate generation. Pellets were resuspended in 100 mM Tris-HCl, pH 8 and lysed using a homogenizer (2 passes at 15 k psi). Cell debris were removed by centrifugation at 21,000×g for 20 min at 4° C. Varying amounts of the lysate obtained from cells grown in proline (representing varying levels of PutA activity) were combined with lysate obtained from cells over-expressing CarB. Reactions also contained 8 mM MgCl$_2$, 7.5 mM FAD, 4 mM malonyl-CoA and 50 mM cis- or trans-3-hydroxy-proline. Ethanol-quenched reactions were analyzed by LCMSMS as described in Example 1. Data are illustrated in FIG. 14.

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of generating a compound of Formula (I-a):

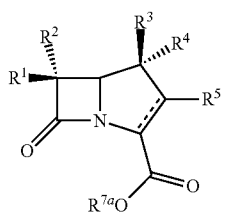

(I-a)

or a salt or tautomer thereof, or a combination thereof;
the method comprising:
(1) providing one or more cell lysates comprising:
   a. ProA and ProB, or γ-glutamyl kinase-GP-reductase multienzyme complex;
   b. Glk;
   c. Pgi;
   d. PfkA;
   e. Fba;
   f. TpiA;
   g. GapA;
   h. Pgk;
   i. GpmA;
   j. Eno;
   k. PykA;
   l. PykF;
   m. AceE;
   n. AceF;
   o. acetyl-CoA acetyltransferase;
   p. acetyl-CoA carboxylase and malonyl-CoA reductase, or beta-alanine transaminase;
   q. S-hydratase and 3-hydroxyacyl-CoA dehydrogenese, or beta-oxidation multienzyme;
   r. crotonyl-CoA reductase;
   s. threonine aldolase;
   t. carboxymethyl-Pro synthase;
   u. carbapenam synthetase or beta-lactam synthetase; and
   v. carbapenem synthase;
or isozymes thereof;
   wherein the one or more cell lysates are contacted with glucose and glycine, or salts thereof, to provide a compound of Formula (I-a) or a salt or tautomer thereof or a combination thereof, wherein $R^1$ is hydrogen, $R^2$ is —$CH_2CH_3$, $R^3$ is hydrogen, $R^4$ is hydrogen, and $R^5$ is —OH; or (2) providing one or more cell lysates comprising:
   a. ProA and ProB, or γ-glutamyl kinase-GP-reductase multienzyme complex;
   b. Glk;
   c. Pgi;
   d. PfkA;
   e. Fba;
   f. TpiA;
   g. GapA;
   h. Pgk;
   i. GpmA;
   j. Eno;
   k. PykA;
   l. PykF;
   m. AceE;
   n. AceF;
   o. acetyl-CoA carboxylase and malonyl-CoA reductase, or beta-alanine transaminase;
   p. threonine aldolase;
   q. carboxymethyl-Pro synthase;
   r. carbapenam synthetase or beta-lactam synthetase; and
   s. carbapenem synthase;
or isozymes thereof;
   wherein the one or more cell lysates are contacted with glucose and glycine, or salts thereof, to provide a compound of Formula (I-a) or a salt or tautomer thereof or a combination thereof, wherein $R^1$ is hydrogen, $R^2$ is hydrogen, $R^3$ is hydrogen, $R^4$ is hydrogen, and $R^5$ is —OH; or (3) providing one or more cell lysates comprising:
   a. ProA and ProB, or γ-glutamyl kinase-GP-reductase multienzyme complex;
   b. Glk;
   c. Pgi;
   d. PfkA;
   e. Fba;
   f. TpiA;
   g. GapA;
   h. Pgk;
   i. GpmA;
   j. Eno;
   k. PykA;
   l. PykF;
   m. AceE;
   n. AceF;
   o. acetyl-CoA acetyltransferase;
   p. S-hydratase and 3-hydroxyacyl-CoA dehydrogenese, or beta-oxidation multienzyme;
   q. crotonyl-CoA reductase;
   r. carboxymethyl-Pro synthase;
   s. carbapenam synthetase or beta-lactam synthetase; and
   t. carbapenem synthase;
or isozymes thereof;
   wherein the one or more cell lysates are contacted with glucose and an optionally substituted glutamate of the formula (i):

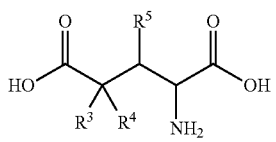

(i)

or salts thereof, to provide a compound of Formula (I-a) or a salt or tautomer thereof or a combination thereof, wherein $R^1$ is hydrogen and $R^2$ is —$CH_2CH_3$; or (4) providing one or more cell lysates comprising:
a. ProA and ProB, or γ-glutamyl kinase-GP-reductase multienzyme complex;
b. Glk;
c. Pgi;
d. PfkA;
e. Fba;
f. TpiA;
g. GapA;
h. Pgk;
i. GpmA;
j. Eno;
k. PykA;
l. PykF;
m. AceE;
n. AceF;
o. acetyl-CoA carboxylase;
p. carboxymethyl-Pro synthase;
q. carbapenam synthetase or beta-lactam synthetase; and
r. carbapenem synthase;
or isozymes thereof;
wherein the one or more cell lysates are contacted with glucose and an optionally substituted glutamate of the formula (i):

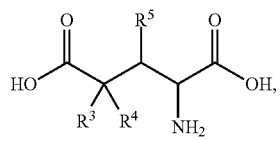

or salts thereof, to provide a compound of Formula (I-a) or a salt or tautomer thereof or a combination thereof, wherein $R^1$ is hydrogen and $R^2$ is hydrogen; or (5) providing one or more cell lysates comprising:
a. Glk;
b. Pgi;
c. PfkA;
d. Fba;
e. TpiA;
f. GapA;
g. Pgk;
h. GpmA;
i. Eno;
j. PykA;
k. PykF;
l. AceE;
m. AceF;
n. acetyl-CoA acetyltransferase;
o. S-hydratase and 3-hydroxyacyl-CoA dehyrogenase, beta-oxidation multienzyme;
p. crotonyl-CoA reductase,
q. proline 3-hydroxylase;
r. proline oxidase;
s. carboxymethyl-Pro synthase;
t. carbapenam synthetase or beta-lactam synthetase; and
u. carbapenem synthase;
or isozymes thereof;

wherein the one or more cell lysates are contacted with glucose and a proline compound of formula (iv):

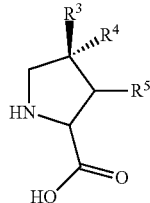

or salts thereof, wherein $R^5$ is hydrogen, to provide a compound of Formula (I-a) or a salt or tautomer thereof or a combination thereof, wherein $R^1$ is hydrogen, $R^2$ is —$CH_2CH_3$, and $R^5$ is —OH; or (6) providing one or more cell lysates comprising:
a. Glk;
b. Pgi;
c. PfkA;
d. Fba;
e. TpiA;
f. GapA;
g. Pgk;
h. GpmA;
i. Eno;
j. PykA;
k. PykF;
l. AceE;
m. AceF;
n. acetyl-CoA carboxylase;
o. proline 3-hydroxylase;
p. proline oxidase;
q. carboxymethyl-Pro synthase;
r. carbapenam synthetase or beta-lactam synthetase; and
s. carbapenem synthase;
or isozymes thereof;
wherein the one or more cell lysates are contacted with glucose and a proline compound of formula (iv):

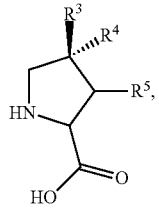

or salts thereof, wherein $R^5$ is hydrogen, to provide a compound of Formula (I-a) or a salt or tautomer thereof or a combination thereof, wherein $R^1$ is hydrogen, $R^2$ is hydrogen, and $R^5$ is —OH; or (7) providing one or more cell lysates comprising:
a. Glk;
b. Pgi;
c. PfkA;
d. Fba;
e. TpiA;
f. GapA;
g. Pgk;
h. GpmA;

i. Eno;
j. PykA;
k. PykF;
l. AceE;
m. AceF;
n. acetyl-CoA acetyltransferase;
o. S-hydratase and 3-hydroxyacyl-CoA dehydrogenase, or beta-oxidation multienzyme;
p. crotonyl-CoA reductase,
q. proline oxidase;
r. carboxymethyl-Pro synthase;
s. carbapenam synthetase or beta-lactam synthetase; and
t. carbapenem synthase;
or isozymes thereof;
wherein the one or more cell lysates are contacted with glucose and a proline compound of formula (iv):

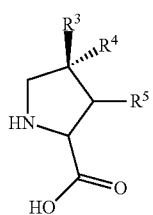

(iv)

or salts thereof, to provide a compound of Formula (I-a) or a salt or tautomer thereof or a combination thereof, wherein $R^1$ is hydrogen and $R^2$ is —$CH_2CH_3$; or (8) providing one or more cell lysates comprising:
a. Glk;
b. Pgi;
c. PfkA;
d. Fba;
e. TpiA;
f. GapA;
g. Pgk;
h. GpmA;
i. Eno;
j. PykA;
k. PykF;
l. AceE;
m. AceF;
n. acetyl-CoA carboxylase;
o. proline oxidase;
p. carboxymethyl-Pro synthase;
q. carbapenam synthetase or beta-lactam synthetase; and
r. carbapenem synthase;
or isozymes thereof;
wherein the one or more cell lysates are contacted with glucose and a proline compound of formula (iv):

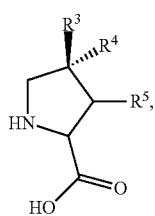

(iv)

or salts thereof, to provide a compound of Formula (I-a) or a salt or tautomer thereof or a combination thereof, wherein $R^1$ is hydrogen and $R^2$ is hydrogen;

wherein:
the dashed line ---- represents a double bond;
each instance of $R^3$ and $R^4$ is independently selected from the group consisting of hydrogen, optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, and optionally substituted heteroaryl;
$R^5$ is hydrogen or —$OR^8$;
each instance of $R^8$ is independently selected from the group consisting of hydrogen, optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, optionally substituted heteroaryl, —$C(=O)R^{8a}$, —$C(=O)OR^{8a}$, —$C(=O)SR^{8a}$, —$C(=O)N(R^{8b})_2$, —$C(=NR^{8b})R^{8a}$, —$C(=NR^{8b})OR^{8a}$, —$C(=NR^{8b})SR^{8a}$, —$C(=NR^{8b})N(R^{8b})_2$, —$C(=S)R^{8a}$, —$C(=S)OR^{8a}$, —$C(=S)SR^{8a}$, —$C(=S)N(R^{8b})_2$, —$C(=O)NR^{8b}SO_2R^{8a}$, —$S(=O)R^{8a}$, —$SO_2R^{8a}$, —$SO_2N(R^{8a})_2$, —$Si(R^{8a})_3$, —$P(=O)(R^{8a})_2$, —$P(=O)(OR^{8a})_2$, —$P(=O)(R^{8a})(OR^{8a})$, —$P(=O)(R^{8a})(N(R^{8b})_2)$, —$P(=O)(N(R^{8b})_2)_2$, —$P(=O)_2R^{8a}$, —$P(=O)_2OR^{8a}$, —$P(=O)_2N(R^{8b})_2$, —$B(R^{8a})_2$, —$B(OR^{8a})_2$, and —$BR^{8a}(OR^{8a})$, wherein $R^{8a}$ is selected from the group consisting of optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, optionally substituted heteroaryl, if attached to an oxygen atom an oxygen protecting group, and if attached to a sulfur atom a sulfur protecting group, or two $R^{8a}$ groups or an $R^{8a}$ and $R^{8b}$ group are joined to form an optionally substituted heterocyclic ring; and each instance of $R^{8b}$ is independently selected from the group consisting of hydrogen, optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, optionally substituted heteroaryl, and a nitrogen protecting group, or two $R^{8b}$ are joined to form an optionally substituted heterocyclic ring; and
$R^{7a}$ is hydrogen;
wherein one or more enzymes selected from the group consisting of carboxymethyl-Pro synthase, carbapenam synthetase, beta-lactam synthetase, carbapenem synthase, and isozymes thereof, is sequestered in the periplasmic space of the cell prior to lysing; and
wherein the one or more cell lysates are bacterial cell lysates.

2. The method of claim 1, wherein $R^3$ is hydrogen or —$CH_3$.

3. The method of claim 1, wherein $R^4$ is hydrogen.

4. The method of claim 1, wherein one or more enzymes selected from the group consisting of ProA, ProB, γ-glutamyl kinase-GP-reductase multienzyme complex, Glk, Pgi, PfkA, Fba, TpiA, GapA, Pgk, GpmA, Eno, PykA, PykF, AceE, Ace, acetyl-CoA acetyltransferase, beta-oxidation multienzyme, S-hydratase, 3-hydroxyacyl-CoA dehydrogenase, crotonyl CoA reductase, acetyl-CoA carboxylase, malonyl-CoA reductase, threonine aldolase, beta-alanine transaminase, proline 3-hydroxylase, proline oxidase, and isozymes thereof, were present in the cell cytoplasm prior to lysing.

5. The method of claim 1, wherein the cell lysate is a lysate of an *E. coli* organism engineered to overexpress the group of enzymes.

6. The method of claim 1, wherein $R^5$ is hydrogen or —OH, and the proline compound of formula (iv):

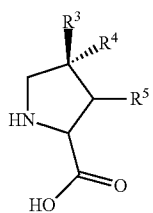

(iv)

or salt thereof, is enzymatically converted to a compound of formula:

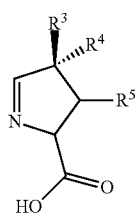

(v)

or salt thereof; upon contact with proline oxidase; and wherein glucose or salt thereof is enzymatically converted to an optionally substituted CoA compound of formula (iii):

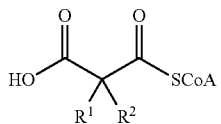

(iii)

or salt thereof; wherein —SCoA is Coenzyme A monoradical.

7. The method of claim 1, wherein the proline compound of formula (iv):

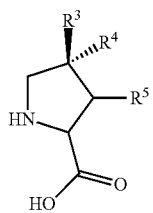

(iv)

or salt thereof, wherein $R^5$ is hydrogen, is enzymatically converted to a 3-hydroxylated proline compound of formula:

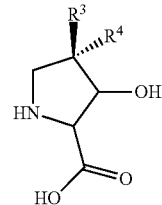

(iv-a)

or salt thereof; upon contact with proline-3-hydroxylase, and the 3-hydroxylated proline compound of formula (iv-a) or salt thereof, is enzymatically converted to a 3-hydroxylated compound of formula:

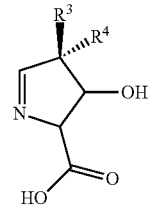

(v-a)

upon contact with proline oxidase.

8. The method of claim 1, wherein $R^5$ is —OH, and the glucose and glycine or salts thereof are enzymatically converted to an optionally substituted glutamate semialdehyde of formula (ii):

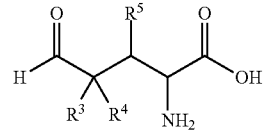

(ii)

or salt thereof, upon contact with ProA and ProB, or γ-glutamyl kinase-GP-reductase multienzyme complex; acetyl-CoA carboxylase and malonyl-CoA reductase, or a beta-alanine transaminase; Glk; Pgi; PfkA; Fba; TpiA; GapA; Pgk; GpmA; Eno; PykA; PykF; AceE; AceF; and threonine aldolase; or isozymes thereof; and wherein glucose or salt thereof is enzymatically converted to an optionally substituted CoA compound of formula (iii):

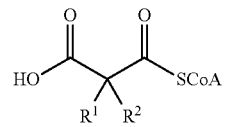

(iii)

or salt thereof; wherein —SCoA is Coenzyme A monoradical.

9. The method of claim 1, wherein $R^5$ is hydrogen or —OH, and the optionally substituted glutamate of formula (i) or salt thereof is enzymatically converted to an optionally substituted glutamate semialdehyde compound of formula (ii):

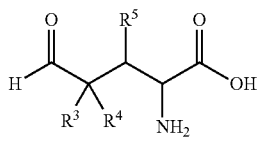

(ii)

or salt thereof; upon contact with ProA and ProB, or γ-glutamyl kinase-GP-reductase multienzyme complex; and wherein glucose or salt thereof is enzymatically converted to an optionally substituted CoA compound of formula (iii):

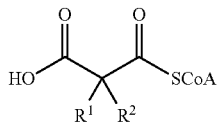

(iii)

or salt thereof; wherein —SCoA is Coenzyme A monoradical.

10. The method of claim 1, wherein the optionally substituted glutamate of formula (i):

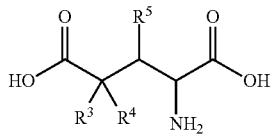

(i)

or salt thereof, is enzymatically converted to a compound of formula (v):

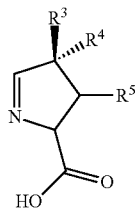

(v)

or salt thereof; upon contact with ProA and ProB, or γ-glutamyl kinase-GP-reductase multienzyme complex.

11. A method of generating a compound of Formula (I-a):

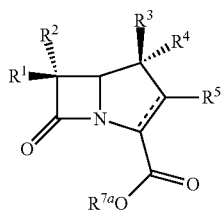

(I-a)

or a salt or tautomer thereof, or a combination thereof, the method comprising:

(1) providing one or more cell lysates comprising:
   a. ProA and ProB, or γ-glutamyl kinase-GP-reductase multienzyme complex;
   b. Glk;
   c. Pgi;
   d. PfkA;
   e. Fba;
   f. TpiA;
   g. GapA;
   h. Pgk;
   i. GpmA;
   j. Eno;
   k. PykA;
   l. PykF;
   m. AceE;
   n. AceF;
   o. acetyl-CoA acetyltransferase;
   p. acetyl-CoA carboxylase and malonyl-CoA reductase, or beta-alanine transaminase;
   q. S-hydratase and 3-hydroxyacyl-CoA dehydrogenase, or beta-oxidation multienzyme;
   r. crotonyl-CoA reductase;
   s. threonine aldolase;
   t. carboxymethyl-Pro synthase;
   u. carbapenam synthetase or beta-lactam synthetase; and
   v. carbapenem synthase;

or isozymes thereof;
   wherein the one or more cell lysates are contacted with glucose and glycine, or salts thereof, to provide a compound of Formula (I-a) or a salt or tautomer thereof or a combination thereof, wherein $R^1$ is hydrogen, $R^2$ is —$CH_2CH_3$, $R^3$ is hydrogen, $R^4$ is hydrogen, and $R^5$ is —OH; or (2) providing one or more cell lysates comprising:
   a. ProA and ProB, or γ-glutamyl kinase-GP-reductase multienzyme complex;
   b. Glk;
   c. Pgi;
   d. PfkA;
   e. Fba;
   f. TpiA;
   g. GapA;
   h. Pgk;
   i. GpmA;
   j. Eno;
   k. PykA;
   l. PykF;
   m. AceE;
   n. AceF;
   o. acetyl-CoA carboxylase and malonyl-CoA reductase, or beta-alanine transaminase;
   p. threonine aldolase;
   q. carboxymethyl-Pro synthase;
   r. carbapenam synthetase or beta-lactam synthetase; and
   s. carbapenem synthase;

or isozymes thereof;
   wherein the one or more cell lysates are contacted with glucose and glycine, or salts thereof, to provide a compound of Formula (I-a) or a salt or tautomer thereof or a combination thereof, wherein $R^1$ is hydrogen, $R^2$ is hydrogen, $R^3$ is hydrogen, $R^4$ is hydrogen, and $R^5$ is —OH; or (3) providing one or more cell lysates comprising:
  a. ProA and ProB, or γ-glutamyl kinase-GP-reductase multienzyme complex;
  b. Glk;
  c. Pgi;
  d. PfkA;
  e. Fba;
  f. TpiA;
  g. GapA;
  h. Pgk;
  i. GpmA;
  j. Eno;
  k. PykA;
  l. PykF;
  m. AceE;
  n. AceF;
  o. acetyl-CoA acetyltransferase;
  p. S-hydratase and 3-hydroxyacyl-CoA dehydrogenese, or beta-oxidation multienzyme;
  q. crotonyl-CoA reductase,
  r. carboxymethyl-Pro synthase;
  s. carbapenam synthetase or beta-lactam synthetase; and
  t. carbapenem synthase;
or isozymes thereof;
  wherein the one or more cell lysates are contacted with glucose and an optionally substituted glutamate of the formula (i):

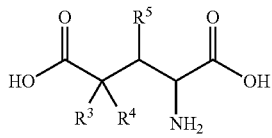

(i)

or salts thereof, wherein $R^5$ is —OH, to provide a compound of Formula (I-a) or a salt or tautomer thereof or a combination thereof, wherein $R^1$ is hydrogen, $R^2$ is —$CH_2CH_3$, and $R^5$ is —OH; or (4) providing one or more cell lysates comprising:
  a. ProA and ProB, or γ-glutamyl kinase-GP-reductase multienzyme complex;
  b. Glk;
  c. Pgi;
  d. PfkA;
  e. Fba;
  f. TpiA;
  g. GapA;
  h. Pgk;
  i. GpmA;
  j. Eno;
  k. PykA;
  l. PykF;
  m. AceE;
  n. AceF;
  o. acetyl-CoA carboxylase;
  p. carboxymethyl-Pro synthase;
  q. carbapenam synthetase or beta-lactam synthetase; and
  r. carbapenem synthase;
or isozymes thereof;
  wherein the one or more cell lysates are contacted with glucose and an optionally substituted glutamate of the formula (i):

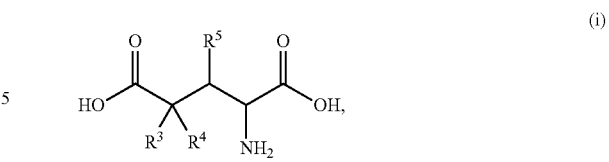

(i)

or salts thereof, wherein $R^5$ is —OH, to provide a compound of Formula (I-a) or a salt or tautomer thereof or a combination thereof, wherein $R^1$ is hydrogen, $R^2$ is hydrogen, and $R^5$ is —OH; or (5) providing one or more cell lysates comprising:
  a. Glk;
  b. Pgi;
  c. PfkA;
  d. Fba;
  e. TpiA;
  f. GapA;
  g. Pgk;
  h. GpmA;
  i. Eno;
  j. PykA;
  k. PykF;
  l. AceE;
  m. AceF;
  n. acetyl-CoA acetyltransferase;
  o. S-hydratase and 3-hydroxyacyl-CoA dehydrogenese, or beta-oxidation multienzyme;
  p. crotonyl-CoA reductase,
  q. proline 3-hydroxylase;
  r. proline oxidase;
  s. carboxymethyl-Pro synthase;
  t. carbapenam synthetase or beta-lactam synthetase; and
  u. carbapenem synthase;
or isozymes thereof;
  wherein the one or more cell lysates are contacted with glucose and a proline compound of formula (iv):

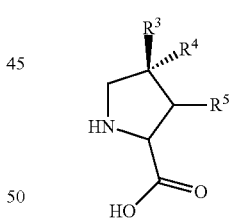

(iv)

or salts thereof, wherein $R^5$ is hydrogen, to provide a compound of Formula (I-a) or a salt or tautomer thereof or a combination thereof, wherein $R^1$ is hydrogen, $R^2$ is —$CH_2CH_3$, and $R^5$ is —OH; or (6) providing one or more cell lysates comprising:
  a. Glk;
  b. Pgi;
  c. PfkA;
  d. Fba;
  e. TpiA;
  f. GapA;
  g. Pgk;
  h. GpmA;
  i. Eno;
  j. PykA;

k. PykF;
l. AceE;
m. AceF;
n. acetyl-CoA carboxylase;
o. proline 3-hydroxylase;
p. proline oxidase;
q. carboxymethyl-Pro synthase;
r. carbapenam synthetase or beta-lactam synthetase; and
s. carbapenem synthase;
or isozymes thereof;
   wherein the one or more cell lysates are contacted with glucose and a proline compound of formula (iv):

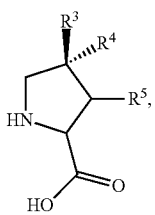

(iv)

or salts thereof, wherein R⁵ is hydrogen, to provide a compound of Formula (I-a) or a salt or tautomer thereof or a combination thereof, wherein R¹ is hydrogen, R² is hydrogen, and R⁵ is —OH; or (7) providing one or more cell lysates comprising:
a. Glk;
b. Pgi;
c. PfkA;
d. Fba;
e. TpiA;
f. GapA;
g. Pgk;
h. GpmA;
i. Eno;
j. PykA;
k. PykF;
l. AceE;
m. AceF;
n. acetyl-CoA acetyltransferase;
o. S-hydratase and 3-hydroxyacyl-CoA dehydrogenese, or beta-oxidation multienzyme;
p. crotonyl-CoA reductase,
q. proline oxidase;
r. carboxymethyl-Pro synthase;
s. carbapenam synthetase or beta-lactam synthetase; and
t. carbapenem synthase;
or isozymes thereof;
   wherein the one or more cell lysates are contacted with glucose and a proline compound of formula (iv):

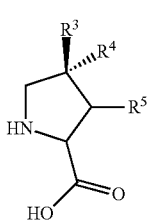

(iv)

or salts thereof, wherein R⁵ is —OH, to provide a compound of Formula (I-a) or a salt or tautomer thereof or a combination thereof, wherein R¹ is hydrogen, R² is —CH₂CH₃, and R⁵ is —OH; or (8) providing one or more cell lysates comprising:
a. Glk;
b. Pgi;
c. PfkA;
d. Fba;
e. TpiA;
f. GapA;
g. Pgk;
h. GpmA;
i. Eno;
j. PykA;
k. PykF;
l. AceE;
m. AceF;
n. acetyl-CoA carboxylase;
o. proline oxidase;
p. carboxymethyl-Pro synthase;
q. carbapenam synthetase or beta-lactam synthetase; and
r. carbapenem synthase;
or isozymes thereof;
   wherein the one or more cell lysates are contacted with glucose and a proline compound of formula (iv):

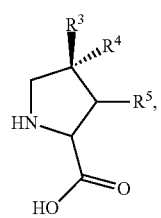

(iv)

or salts thereof, wherein R⁵ is —OH, to provide a compound of Formula (I-a) or a salt or tautomer thereof or a combination thereof, wherein R¹ is hydrogen, R² is hydrogen, and R⁵ is —OH;
wherein:
   the dashed line ---- represents a double bond;
   each instance of R³ and R⁴ is independently selected from the group consisting of hydrogen, optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, and optionally substituted heteroaryl;
   R⁷ᵃ is hydrogen; and
   wherein the one or more cell lysates are bacterial cell lysates;
   wherein the combination of glucose and glycine, or salts thereof, or the combination of glucose and an optionally substituted glutamate of the formula (i), or salts thereof, is enzymatically converted to an optionally substituted CoA compound of formula (iii), or salt thereof, and an optionally substituted glutamate semialdehyde of formula (ii), or salt thereof:

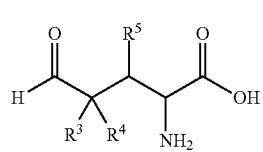

(ii)

-continued

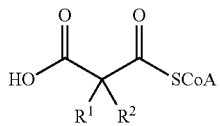
(iii)

wherein —SCoA is Coenzyme A monoradical; and
wherein the optionally substituted glutamate semialdehyde of formula (ii) or salt thereof and the optionally substituted CoA compound of formula (iii) or salt thereof are enzymatically converted to a pyrrolidinyl compound of Formula (II-a):

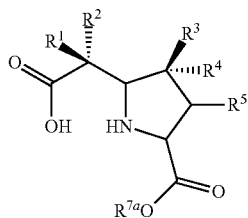
(II-a)

or salt thereof, upon contact with carboxymethylPro synthase or an isozyme thereof;
further wherein the pyrrolidinyl compound (II-a) or salt thereof is enzymatically converted to a β-lactam compound of Formula (III-a):

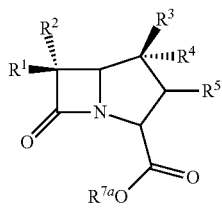
(III-a)

or salt thereof, upon contact with carbapenam synthetase or beta-lactam synthetase, or an isozyme thereof; and
further wherein the β-lactam compound of Formula (III-a) or salt thereof generates a compound of Formula (I-a):

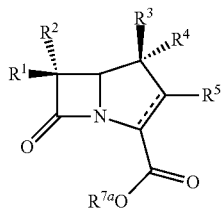
(I-a)

or salt thereof, wherein ---- represents a double bond, upon contact with carbapenem synthase or isozyme thereof.

12. The method of claim 1, wherein $R^5$ is hydrogen or —OH, and the combination of glucose or salt thereof and the proline compound of formula (iv) or salt thereof is enzymatically converted to an optionally substituted CoA compound of formula (iii), or salt thereof, and a compound of formula (v), or salt thereof:

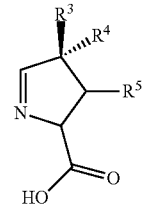
(v)

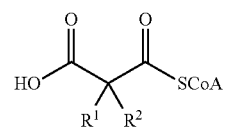
(iii)

wherein —SCoA is Coenzyme A monoradical; and
wherein the optionally substituted CoA compound of formula (iii), or salt thereof, and the compound of formula (v), or salt thereof are enzymatically converted to a pyrrolidinyl compound of Formula (II-a):

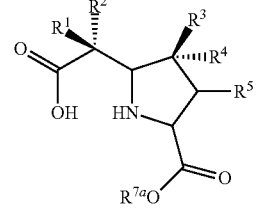
(II-a)

or salt thereof, upon contact with carboxymethylPro synthase or an isozyme thereof.

13. The method of claim 11, wherein the compound of Formula (I-a):

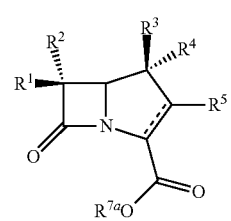
(I-a)

or a salt or tautomer thereof, or a combination thereof, wherein ---- represents a double bond;
is contacted with a compound of the formula:

$$R^{8'}—X$$

wherein:
X is a leaving group; and
$R^{8'}$ is selected from the group consisting of —C(=O)$R^{8a}$, —C(=O)O$R^{8a}$, —C(=O)S$R^{8a}$, —C(=O)N($R^{8b}$)$_2$, —C(=N$R^{8b}$)$R^{8a}$, —C(=N$R^{8b}$)O$R^{8a}$, —C(=N$R^{8b}$)S$R^{8a}$, —C(=N$R^{8b}$)N($R^{8b}$)$_2$, —C(=S)$R^{8a}$, —C(=S)O$R^{8a}$, —C(=S)S$R^{8a}$, —C(=S)N($R^{8b}$)$_2$, —C(=O)N$R^{8b}$SO$_2$$R^{8a}$, —S(=O)$R^{8a}$, —SO$_2$$R^{8a}$, —SO$_2$N($R^{8a}$)$_2$, —Si($R^{8a}$)$_3$, —P(=O)($R^{8a}$)$_2$, —P(=O)(O$R^{8a}$)$_2$, —P(=O)($R^{8a}$)(O$R^{8a}$), —P(=O)($R^{8a}$)(N($R^{8b}$)$_2$), —P(=O)(N($R^{8b}$)$_2$)$_2$, —P(=O)$_2$$R^{8a}$, —P(=O)$_2$O$R^{8a}$, —P(=O)$_2$N($R^{8b}$)$_2$, —B($R^{8a}$)$_2$, —B(OR$^{8a}$)$_2$, and —BR$^{8a}$(OR$^{8a}$), wherein R$^{8a}$ is selected from the group consisting of optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, optionally substituted heteroaryl, if attached to an oxygen atom an oxygen protecting group, and if attached to a sulfur atom a sulfur protecting group, or two R$^{8a}$ groups or an R$^{8a}$ and R$^{8b}$ group are joined to form an optionally substituted heterocyclic ring; and each instance of R$^{8b}$ is independently selected from the group consisting of hydrogen, optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, optionally substituted heteroaryl, and a nitrogen protecting group, or two R$^{8b}$ are joined to form an optionally substituted heterocyclic ring;

to provide a compound of Formula (I-e):

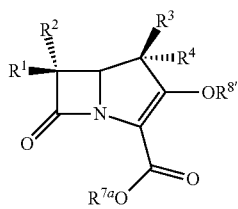

(I-e)

or salt thereof.

14. The method of claim 13, wherein the compound of Formula (I-e) is contacted with a compound of the formula HS—R$^8$, wherein R$^8$ is selected from the group consisting of optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, and optionally substituted heteroaryl;

to provide a thiol-containing compound of Formula (I-c):

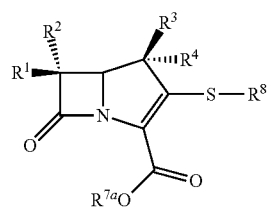

(I-c)

or salt thereof.

15. The method of claim 11, wherein R$^2$ is —CH$_2$CH$_3$.

16. The method of claim 15, further comprising contacting the compound with an oxygenase enzyme to provide a hydroxylated compound wherein R$^2$ is —CH(OH)CH$_3$.

17. The method of claim 11, wherein R$^1$ and R$^2$ are both hydrogen.

18. The method of claim 17, further comprising contacting the compound with a methyltransferase enzyme to provide a compound wherein R$^1$ is hydrogen and R$^2$ is —CH$_3$ or —CH$_2$CH$_3$.

19. The method of claim 18, further comprising contacting the compound wherein R$^2$ is —CH$_2$CH$_3$ with an oxygenase enzyme to provide a hydroxylated compound wherein R$^2$ is —CH(OH)CH$_3$.

20. The method of claim 14, wherein R$^8$ is an optionally substituted alkyl, optionally substituted heteroalkyl, or optionally substituted heterocyclyl.

21. The method of claim 20, wherein R$^8$ is selected from the group consisting of:

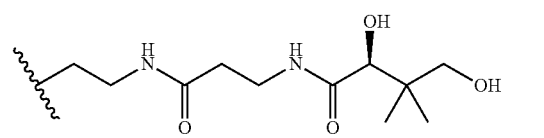

(a)

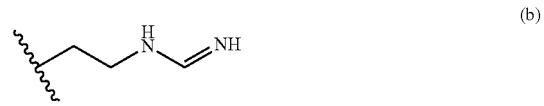

(b)

(c)

(d)

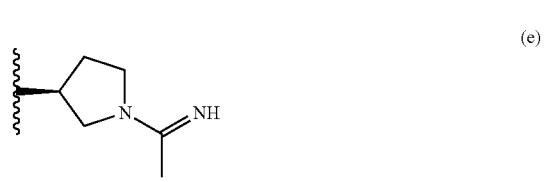

(e)

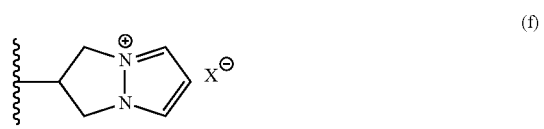

(f)

(g)

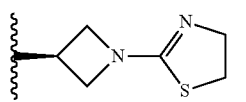
(h)
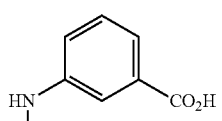
(l)
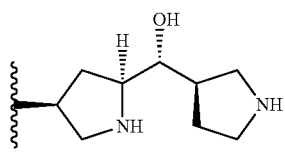
(i)
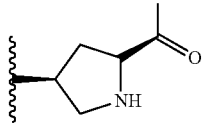
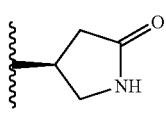
(m)
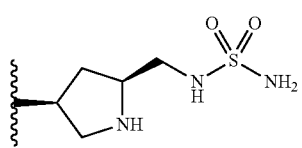
(j)
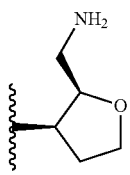
(n)
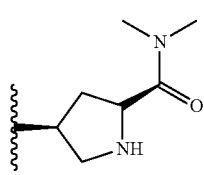
(k)
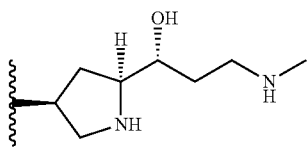
(o)
wherein X$^-$ is a counterion.
* * * * *